US011708350B2

(12) United States Patent
O'Malley et al.

(10) Patent No.: US 11,708,350 B2
(45) Date of Patent: Jul. 25, 2023

(54) SMALL MOLECULE STIMULATORS OF STEROID RECEPTOR COACTIVATOR-3 AND METHODS OF THEIR USE AS CARDIOPROTECTIVE AND/OR VASCULAR REGENERATIVE AGENTS

(71) Applicant: BAYLOR COLLEGE OF MEDICINE, Houston, TX (US)

(72) Inventors: Bert W. O'Malley, Houston, TX (US); David Michael Lonard, Pearland, TX (US); Yongcheng Song, Pearland, TX (US)

(73) Assignee: Baylor College of Medicine, Houston, TX (US)

( * ) Notice: Subject to any disclaimer, the term of this patent is extended or adjusted under 35 U.S.C. 154(b) by 287 days.

(21) Appl. No.: 17/030,924

(22) Filed: Sep. 24, 2020

(65) Prior Publication Data

US 2021/0115017 A1    Apr. 22, 2021

Related U.S. Application Data

(63) Continuation of application No. 16/554,733, filed on Aug. 29, 2019, now Pat. No. 10,875,841.

(60) Provisional application No. 62/825,358, filed on Mar. 28, 2019, provisional application No. 62/724,281, filed on Aug. 29, 2018.

(51) Int. Cl.
*C07D 401/14* (2006.01)
*A61P 9/10* (2006.01)
*C07D 401/08* (2006.01)

(52) U.S. Cl.
CPC .............. *C07D 401/14* (2013.01); *A61P 9/10* (2018.01); *C07D 401/08* (2013.01)

(58) Field of Classification Search
CPC ................................ C07D 401/14; A61P 9/10
USPC ......................................................... 514/336
See application file for complete search history.

(56) References Cited

U.S. PATENT DOCUMENTS

| 6,664,272 | B2 | 12/2003 | Snyder et al. |
| 8,785,490 | B2 | 7/2014 | Trent et al. |
| 2007/0010488 | A1 | 1/2007 | Youssef et al. |
| 2010/0093611 | A1 | 4/2010 | Horrigan et al. |
| 2011/0059157 | A1 | 3/2011 | Awasthi et al. |

FOREIGN PATENT DOCUMENTS

| CN | 102381951 | 3/2012 |
| CN | 102153508 | 1/2013 |
| CN | 106083704 | * 11/2016 |
| CN | 102153508 | * 8/2017 |
| CN | 106083704 | 7/2018 |
| EP | 2303328 | 4/2011 |
| EP | 2927208 | 10/2015 |
| WO | 9518606 | 7/1995 |
| WO | 0140188 | 6/2001 |
| WO | 0146110 | 6/2001 |
| WO | 2008144011 | 11/2008 |
| WO | 2008150899 | 12/2008 |
| WO | 2009073050 | 6/2009 |
| WO | 2011029359 | 3/2011 |
| WO | 2012021692 | 2/2012 |
| WO | 2014082581 | 6/2014 |
| WO | 2014111268 | 7/2014 |
| WO | 2019097080 | 5/2019 |

OTHER PUBLICATIONS

Albert et al., Revistade Chimie (Bucharest, Romania) (1975), 26(11), 902-4.*
Liu et al., Zhongguo Yaowu Huaxue Zazhi (2011), 21(4), 262-266.*
U.S. Appl. No. 16/554,733, Supplemental Notice of Allowability, dated Nov. 18, 2020, 2 pages.
(3E,5E)-3,5-Bis(Pyridine-3-Ylmethylidene)Oxan-4-One Lnchi Key: CCSROPREUQUEHY_BGPOSVGRSA_N, Chemical- SureChem, Available Online at: https://open.surechem.com/en/chemical?struct, Mar. 27, 2014, 3 pages.
4-Ethyl-2,6-Bis-Pyridin-3-Ylmethylene-Cyclohexanone, Pubchem Bioassay, CID 217594 7—Compound BioActivity, Available Online at: http://pubchem.ncbi.nlm.nih.gov/assay/assay.cgi, Aug. 12, 2014, 25 pages.
Counterscreen for Inhibitors of the Steroid Receptor Coactivator 3 (SRC3; NCOA3): Luminescence-Based Cell-Based High Throughput Assay to Identify Inhibitors of the Herpes Virus Virion Protein 16 (VP16), Pubchem Bioassay, Available Online at: http:l/pubchem.ncbi.nlm.nih.gov/bioassay/588794, Nov. 16, 2011, 17 pages.
Luminescence-Based Cell-Based Primary High Throughput Screening Assay to Identify Inhibitors of the Steroid Receptor Coactivator 2 (SRC2; NCOA2), Pubchem Bioassay, Available Online at: http://pubchem.ncbi.nlm.nih.gov/assay/assay.cgi?aid=651957, Mar. 27, 2014, 16 pages.
Pubchem Cid Nos. 13306030 (3E,5E)-3,5-Bis[(2-Methoxyphenyl)Methylidene]-1-Methylpiperidin-4-One; 20416720 (3E,5E)-1-Ethyl-3,5-Bis[(2Methoxyphenyl)Methylidene]Piperidin-4-One; 20416721 (3E,5E)-3,5-Bis[(2-Methoxyphenyl)Methylidene]-1-Propylpiperidin-4-One, Available Online at: https://pubchem.ncbi.nlm.nih.gov/search/index.html, Mar. 27, 2014, 3 pages.
Pubchem Cid Nos. 1587345 (2E,6E)-4-Methyl-2,6-Bis(Pyridine-3-Ylmethylidene)Cyclohexan-1-One; 1587342 (2Z,6E)-4-Methyl-2,6-Bis(Pyridin-3-Ylmethylid En E)Cycloh Exan-1-One; 706760 4-Methyl-2 ,6-Bis(Pyridine-3-Ylmethylidene )Cyclohexan-1-One; 217594 7 (2E,, Available Online at: https://pubchem.ncbi.nlm.nih.gov/search/index.html, Mar. 27, 2014, 10 pages.

(Continued)

*Primary Examiner* — Niloofar Rahmani
(74) *Attorney, Agent, or Firm* — Kilpatrick Townsend & Stockton LLP

(57) ABSTRACT

Small molecule stimulators of steroid receptor coactivator-3 (SRC-3) and methods of their use as cardioprotective agents are provided. The small molecule stimulators are useful for promoting cardiac protection and repair and vascular regeneration after myocardial infarction. The compounds are also useful in preventing cardiac hypertrophy and collagen deposition and improving cardiac post-infarction function.

15 Claims, 26 Drawing Sheets

(56) References Cited

OTHER PUBLICATIONS

Pubchem Cid Nos. 2265240 (3Z,5E)-1-Methyl-3,5-Bis(Pyridine-3-Ylmethylidene)Piperidin-4-One; 2265242 (3E,5E)-1-Methyl-3,5-Bis(Pyridine-3-Ylmethylidene)Piperidin-4-One; 702066 1-Methyl-3,5-Bis(Pyridine-3-Ylmethylidene)Piperidin-4-One; 52446215 (3Z,5E)-1-E, Available Online at: https://pubchem.ncbi.nlm.nih.gov/search/index.html, Mar. 27, 2014, 6 pages.
Pubchem Cid Nos. 3491436 2,6-Bis[(3-Methoxyphenyl)Methylidene]-4-Methylcyclohexan-1-One; 6938059 (2E)-2,6-Bis[(3-Methoxyphenyl)Methylidene ]-4-Methylcyclohexan-1-One; 234 754 7 (2E,6E)-2,6-Bis[(3- Methoxyphenyl) Methylidene ]-4-Methylcyclohexan-1-On E; 23, Available Online at: https://pubchem.ncbi.nlm.nih.gov/search/index.html, Mar. 27, 2014, 7 pages.
Pubchem Cid Nos. 4114212 (2,6-Bis[(3-Methoxyphenyl)Methylidene]Cyclohexan-1-One; 1741341 ((2E,6E)-2,6-Bis[(3-Methoxylphenyl)Methylidene]Cyclohexan-1-One); 17 41339 (2E,6Z)-2,6-Bis[(3- Methoxyphenyl)Methylidene]Cyclohexan-1-One; 3491436 2,6-Bis[(3-Methoxy, Available Online at: https://pubchem.ncbi.nlm.nih.gov/search/index.html, Mar. 27, 2014, 8 pages.
Pubchem Cid Nos. 5070709 3,5-Bis[(3,4-Dichlorophenyl)Methylidene]-1-Ethylpiperidin-4-One; 2390410 (3Z,5E)-3,5-Bis[(3,4-Dichlorophenyl)Methylidene ]-1-Ethylpiperidin-4-One; 2390412 (3E,5E)-3, 5-Bis[(3,4- D Ichloroph Enyl)Methylid En E ]-1-Ethylpiperid In-4, Available Online at: https://pubchem.ncbi.nlm.nih.gov/search/index.html, Mar. 27, 2014, 6 pages.
Pubchem Cid Nos. 5182696 3,5-Bis[3,4-Dichlorophenyl)Methylidene]-1-Propan-2-Ylpiperidin-4-One; 6535788(3E,5E)-3,5-Bis[(3,4-Dichlorophenyl)Methylidene]-1-Propan-2-Ylpiperidin-4-One, Available Online at: https://pubchem.ncbi.nlm.nih.gov/search/index.html, Mar. 27, 2014, 3 pages.
Pubchem Cid Nos. 60165427 (3E,5E)-3,5-Bis(Pyridine-2-Ylmethylidene)Oxan-4-One; 72670476 3,5-Bis(Pyridine-2 Ylmethylidene)Oxan-4-One;, Available Online at: https://pubchem.ncbi.nlm.nih.gov/search/index.html, Mar. 27, 2014, 3 pages.
Pubchem Cid Nos. 6086459 (3E,5E)-3,5-Bis[(4-Bromophenyl)Methylidene]-1-Butylpiperidin-4-One; 5502561 (3E,5E)-3,5-Bis[(4-Bromophenyl)Methylidene ]-1-Methylpiperidin-4-One; 1283565 3, 5-Bis[(4- Bromophynyl)Methylidene]-1-Methylpiperidin-4-One; 1283573 3,5-B, Available Online at: https://pubchem.ncbi.nlm.nih.gov/search/index.html, Mar. 27, 2014, 11 pages.
Pubchem Cid Nos. 6518906 (2E,6E)-2,6-Bis(Pyridine-2-Ylmethylidene)Cyclohexan-1-One; 3839298 2,6-Bis(Pyridine-2-Ylmethylidene)Cyclohexan-1-One; 26788142 (6E)-2,6-Bis(Pyridine-2-Ylmethylidene )Cyclohexan-1-One; 39842650 (2E,6Z)-2,6-Bis(Pyridine-2-Ylmethylid, Available Online at: https://pubchem.ncbi.nlm.nih.gov/search/index.html, Mar. 27, 2014, 4 pages.
Summary of the Probe Development Efforts to Identify Inhibitors of the Steroid Receptor Coactivator 1 (SRC1;NCOA1), Pubchem Bioassay, Available Online at: http:l/pubchem.ncbi.nlm.nih.gov/bioassay/588362, Nov. 21, 2012, 11 pages.
Summary of the Probe Development Efforts to Identify Inhibitors of the Steroid Receptor Coactivator 2 (SRC2;NCOA2), Pubchem Bioassay, Available Online at: l/pubchem.ncbi.nlm.nih.gov/bioassay/651960, Feb. 4, 2013, 10 pages.
Summary of the Probe Development Efforts to Identify Inhibitors of the Steroid Receptor Coactivator 3 (SRC3;NCOA3), Pubchem Bioassay, Available Online at: http:l/pubchem.ncbi.nlm.nih.gov/bioassay/588357, Mar. 4, 2013, 11 pages.
U.S. Appl. No. 15/540,386, Advisory Action dated Nov. 7, 2019, 3 pages.
U.S. Appl. No. 15/540,386, Final Office Action dated Aug. 10, 2020, 11 pages.
U.S. Appl. No. 15/540,386, Final Office Action dated Aug. 30, 2019, 7 pages.
U.S. Appl. No. 15/540,386, Non-Final Office Action dated Mar. 17, 2020, 12 pages.
U.S. Appl. No. 15/540,386, Non-Final Office Action dated Feb. 6, 2019, 53 pages.
U.S. Appl. No. 16/554,733, Notice of Allowance dated Jul. 15, 2020, 12 pages.
Abraham et al., A Morphologically Conserved Nonapoptotic Program Promotes Linker Cell Death in Caenorhabditis Elegans, Developmental Cell, vol. 12, No. 1, Jan. 2007, pp. 73-86.
Adams et al., Discovery of Small-Molecule Enhancers of Reactive Oxygen Species that are Nontoxic or Cause Genotype-selective Cell Death, American Chemical Society, vol. 8, No. 5, May 17, 2013, pp. 923-929.
Adams et al., Synthesis, Cellular Evaluation, and Mechanism of Action of Piperlongumine Analogs, Proceedings of the National Academy of Sciences, vol. 109, No. 38, Sep. 18, 2012, pp. 15115-15120.
Anzick et al., AIB1, a Steroid Receptor Coactivator Amplified in Breast and Ovarian Cancer, Science, vol. 277, No. 5328, 1997, pp. 965-968.
Bautista et al., In Breast Cancer, Amplification of the Steroid Receptor Coactivator Gene AIB1 is Correlated with Estrogen and Progesterone Receptor Positivity, Clinical Cancer Research, vol. 4, No. 12, Dec. 1998, pp. 2925-2929.
Bouras et al., Overexpression of the Steroid Receptor Coactivator AIB1 in Breast Cancer Correlates with the Absence of Estrogen and Progesterone Receptors and Positivity for P53 and Her2/neu, Cancer Research, vol. 61, No. 3, Feb. 2001, pp. 903-907.
Cai et al., Steroid Receptor Coactivator-3 Expression in Lung Cancer and its Role in the Regulation of Cancer Cell Survival and Proliferation, Cancer Research, vol. 70, No. 16, 2010, pp. 6477-6485.
Chen et al., Living T9 Glioma Cells Expressing Membrane Macrophage Colony-Stimulating Factor Produce Immediate Tumor Destruction by Polymorphonuclear Leukocytes and Macrophages via a "Paraptosis"-Induced Pathway that Promotes Systemic Immunity Against Intracranial T9 G, Blood, vol. 100, No. 4, Aug. 15, 2002, pp. 1373-1380.
Chen et al., Nuclear Receptor Coactivator ACTR is a Novel Histone Acetyltransferase and Forms a Multimeric Activation Complex with P/CAF and CBP/p300, Cell, vol. 90, No. 3, Aug. 8, 1997, pp. 569-580.
Chen et al., Regulation of Transcription by a Protein Methyltransferase, Science, vol. 284, No. 5423, Jun. 25, 1999, pp. 2174-2177.
Chi et al., Oncogenic Ras Triggers Cell Suicide Through the Activation of a Caspase-Independent Cell Death Program in Human Cancer Cells, Oncogene, vol. 18, No. 13, Apr. 1, 1999, pp. 2281-2290.
Chin et al., Essential Role for Oncogenic Ras in Tumour Maintenance, Nature, vol. 400, No. 6743, Jul. 29, 1999, pp. 468-472.
Clarke, Developmental Cell Death: Morphological Diversity and Multiple Mechanisms, Anatomy and Embryology, vol. 181, No. 3, Mar. 1990, pp. 195-213.
De Jong et al., Tyrosine 207 in CRKL is the BCR/ABL Phosphorylation Site, Oncogene, vol. 14, Feb. 6, 1997, pp. 507-513.
Dengler et al., Oncogenic Stress Induced by Acute Hyper-Activation of Bcr-Abl Leads to Cell Death upon Induction of Excessive Aerobic Glycolysis, PloS one, vol. 6, No. 9, Sep. 20, 2011, pp. 1-13.
Denoyelle et al., Anti-Oncogenic Role of the Endoplasmic Reticulum Differentially Activated by Mutations in the MAPK Pathway, Nature Cell Biology, vol. 8, No. 10, 2006, 11 pages.
Ding et al., Absence of Bax Switched MG132-Induced Apoptosis to Non-Apoptotic Cell Death that Could be Suppressed by Transcriptional or Translational Inhibition, Apoptosis, vol. 12, No. 12, Dec. 2007, pp. 2233-2244.
Enyedi et al., Redox State of the Endoplasmic Reticulum is Controlled by Ero1L-Alpha and Intraluminal Calcium, Antioxidants & Redox Signaling, vol. 13, No. 6, Sep. 15, 2010, pp. 721-729.
Epps et al., Determination of the Affinity of Drugs Toward Serum Albumin by Measurement of the Quenching of the Intrinsic Tryptophan Fluorescence of the Protein, The Journal of Pharmacy and Pharmacology, vol. 51, No. 1, Jan. 1999, pp. 41-48.
Felsher et al., Reversible Tumorigenesis by MYC in Hematopoietic Lineages, Molecular cell, vol. 4, 1999, pp. 199-207.

(56) References Cited

OTHER PUBLICATIONS

Fereshteh et al., The Nuclear Receptor Coactivator Amplified in Breast Cancer-1 is Required for Neu KErbb2/Her2) Activation, Signaling, and Mammary Tumorigenesis in Mice, Cancer Research, vol. 68, 2008, 19 pages.

Fleming et al., Expression of SRC-1, AIB1, and PEA3 in HER2 Mediated Endocrine Resistant Breast Cancer; a Predictive Role for SRC-1, Journal of Clinical Pathology, vol. 57, No. 10, Oct. 2004, pp. 1069-1074.

Foulds et al., Proteomic Analysis of Coregulators Bound to ERα on DNA and Nucleosomes Reveals Coregulator Dynamics, Mol Cell, vol. 51, No. 2, Jul. 25, 2013, pp. 185-199.

Glaeser et al., Gene Amplification and Expression of the Steroid Receptor Coactivator SRC3 (AIB1) in Sporadic Breast and Endometrial Carcinomas, Hormone and Metabolic Research, vol. 33, No. 3, Mar. 2001, pp. 121-126.

Gnanapragasam et al., Expression of RAC 3, a Steroid Hormone Receptor Co-Activator in Prostate Cancer, British Journal of Cancer, vol. 85, No. 12, Dec. 2001, pp. 1928-1936.

Grek et al., Redox Metabolism and Malignancy, Current Opinion in Pharmacology, vol. 10, No. 4, 2010, pp. 362-368.

Greuber et al., Role of ABL Family Kinases in Cancer: From Leukaemia to Solid Tumours, Nature Reviews Cancer, vol. 13, No. 8, 2013, 27 pages.

Han et al., Er-Stress-Induced Transcriptional Regulation Increases Protein Synthesis Leading to Cell Death, Nature Cell Biology, vol. 15, No. 5, 2013, 24 pages.

Henke et al., Overexpression of the Nuclear Receptor Coactivator AIB1 (SRC-3) During Progression of Pancreatic Adenocarcinoma, Clinical Cancer Research, vol. 10, Sep. 15, 2004, pp. 6134-6142.

Huang et al., Design, Synthesis, and Evaluation of NDGA Analogues as Potential Anti-Ischemic Stroke Agents, European Journal of Medicinal Chemistry, vol. 143, Jan. 2018, pp. 1165-1173.

Hudelist et al., Expression of Sex Steroid Receptors and their Co-Factors in Normal and Malignant Breast Tissue AIB1 is a Carcinoma-Specific Co-Activator, Breast Cancer Research and Treatment, vol. 78, No. 2, Mar. 2003, pp. 193-204.

Huettner et al., Reversibility of Acute B-Cell Leukaemia Induced by BCR-ABL1, Nature Genetics, vol. 24, No. 1, Jan. 2000, pp. 57-60.

Jain et al., Sustained Loss of a Neoplastic Phenotype by Brief Inactivation of MYC, Science, vol. 297, No. 5578, Jul. 5, 2002, pp. 102-104.

Jambrina et al., Calcium Influx Through Receptor-Operated Channel Induces Mitochondria-Triggered Paraptotic Cell Death, The Journal of Biological Chemistry, vol. 278, No. 16, 2003, pp. 14134-14145.

Jana et al., Curcumin Delays Endometriosis Development by Inhibiting MMP-2 Activity, Indian Journal Biochemistry Biophysics, vol. 49, No. 5, Oct. 2012, pp. 342-348.

Kar et al., A Novel Role for MAP1 LC3 in Non-Autophagic Cytoplasmic Vacuolation Death of Cancer Cells, Oncogene, vol. 28, No. 28, 2009, pp. 2556-2568.

Kershah et al., Expression of Estrogen Receptor Coregulators in Normal and Malignant Human Endometrium, Gynecologic Oncology, vol. 92, No. 1, Jan. 2004, pp. 304-313.

Kinoshita et al., Recognition of Phosphate Monoester Dianion by an Alkoxide-Bridged Dinuclear Zinc(II) Complex, Dalton Transactions, vol. 8, No. 8, 2004, pp. 1189-1193.

Kumar et al., Curcumin-Loaded Lipid Nanocarrier for Improving Bioavailability, Stability and Cytotoxicity Against Malignant Glioma Cells, Drug Delivery, vol. 23, No. 1, May 14, 2014, pp. 214-229.

Le et al., Inhibition of Lactate Dehydrogenase a Induces Oxidative Stress and Inhibits Tumor Progression, Proceedings of the National Academy of Sciences of the United States of America, vol. 107, No. 5, 2010, pp. 2037-2042.

Leung et al., Identification of Cyclohexanone Derivatives that Act as Catalytic Inhibitors of Topoisomerase I: Effects on Tamoxifen-Resistant MCF-7 Cancer Cells, Invest New Drugs, vol. 30, 2012, pp. 2103-2112.

List et al., Ribozyme Targeting Demonstrates that the Nuclear Receptor Coactivator AIB1 is a Rate-Limiting Factor for Estrogen-Dependent Growth of Human MCF-7 Breast Cancer Cells, Journal of Biological Chemistry, vol. 276, No. 26, 2001, pp. 23763-23768.

Liu et al., Synthesis of 3, 5-Dibenzylidene-4-Piperidinone Analogs and Their Antitumor Activities in Vitro, Zhongguo Yaowu Huaxue Zazhi, vol. 19, No. 5, 2010, pp. 105-109.

Lonard et al., Nuclear Receptor Coregulators: Judges, Juries, and Executioners of Cellular Regulation, Molecular Cell, vol. 27, No. 5, 2007, pp. 691-700.

Lonard et al., The 26S Proteasome is Required for Estrogen Receptor-α and Coactivator Turnover and for Efficient Estrogen Receptor-α Transactivation, Molecular Cell, vol. 5, No. 6, Jun. 2000, pp. 939-948.

Louet et al., The Coactivator SRC-1 Is an Essential Coordinator of Hepatic Glucose Production, Cell Metabolism, vol. 12, No. 6, Dec. 1, 2010, 22 pages.

Meyer et al., Reflecting on 25 Years with MYC, Nature Reviews Cancer, vol. 8, No. 12, Dec. 2008, pp. 976-990.

Mimnaugh et al., Endoplasmic Reticulum Vacuolization and Valosin-Containing Protein Relocalization Result from Simultaneous Hsp90 Inhibition by Geldanamycin and Proteasome Inhibition by Velcade, Molecular Cancer Research, vol. 4, No. 9, Sep. 2006, pp. 667-681.

Myers et al., Inverse Relationship Between Er-Beta and Src-1 Predicts Outcome in Endocrine-Resistant Breast Cancer, British Journal of Cancer, vol. 91, No. 9, 2004, pp. 1687-1693.

Noguchi et al., ATPase Activity of p97/Valosin-Containing Protein is Regulated by Oxidative Odification of the Evolutionally Conserved Cysteine 522 Residue in Walker a Motif, The Journal of Biological Chemistry, vol. 280, No. 50, 2005, pp. 41332-41341.

Oh et al., Tyrosine Phosphorylation of the Nuclear Receptor Coactivator AIB1/SRC-3 is Enhanced by AbI Kinase and is Required for its Activity in Cancer Cells, Molecular and Cellular Biology, vol. 28, No. 21, 2008, pp. 6580-6593.

O'Malley, Development of Coactivator-Dependent, First-in-Class Therapies for Breast Cancer, Available Online at: www.dtic.miljcgi-binjGetTRDocAD=ADA614113, Sep. 2014, pp. 7-9.

International Application No. PCT/US2015/067770, International Preliminary Report on Patentability dated Jul. 13, 2017, 14 pages.

International Application No. PCT/US2015/067770, International Search Report and Written Opinion dated May 24, 2016, 19 pages.

International Application No. PCT/US2015/067770, Invitation to Pay Additional Fees and Where Applicable Protest Fee dated Mar. 11, 2016, 10 pages.

International Application No. PCT/US2019/048703, International Search Report and Written Opinion dated Jan. 29, 2020, 17 pages.

International Application No. PCT/US2019/048703, Invitation to Pay Additional Fees and Where Applicable Protest Fee dated Dec. 6, 2019, 10 pages.

Pilar et al., Ultrastructural Differences During Embryonic Cell Death in Normal and Peripherally Deprived Ciliary Ganglia, The Journal of Cell Biology, vol. 68, No. 2, Feb. 1976, pp. 339-356.

Qin et al., The Steroid Receptor Coactivator-1 Regulates Twist Expression and Promotes Breast Cancer Metastasis, Cancer Research, vol. 69, No. 9, 2009, 18 pages.

Raj et al., Selective Killing of Cancer Cells by a Small Molecule Targeting the Stress Response to ROS, Nature, vol. 475, No. 7355, 2011, 10 pages.

Ray et al., Reactive Oxygen Species (ROS) Homeostasis and Redox Regulation in Cellular Signaling, Cellular Signalling, vol. 24, No. 5, 2012, 25 pages.

Sakakura et al., Amplification and Over-Expression of the AIB1 Nuclear Receptor Co-activator Gene in Primary Gastric Cancers, International Journal of Cancer, vol. 89, No. 3, 2000, pp. 217-223.

Somers-Edgar et al., Mechanisms for the Activity of Heterocyclic Cyclohexanone Curcumin Derivatives in Estrogen Receptor Negative Human Breast Cancer Cell Lines, Investigational New Drugs, vol. 29, No. 1, 2011, pp. 87-97.

Sperandio et al., An Alternative, Nonapoptotic Form of Programmed Cell Death, Proceedings of the National Academy of Sciences of the United States of America, vol. 97, No. 26, Dec. 19, 2000, pp. 14376-14381.

(56) References Cited

OTHER PUBLICATIONS

Stashi et al., Steroid Receptor Coactivators: Servants and Masters for Control of Systems Metabolism, Trends in Endocrinology and Metabolism, vol. 25, No. 7, 2014, 26 pages.
Sun et al., Activation of the Cytoplasmic c-Abl Tyrosine Kinase by Reactive Oxygen Species, The Journal of Biological Chemistry, vol. 275, No. 23, Jun. 9, 2000, pp. 17237-17240.
Tardito et al., The Thioxotriazole Copper(II) Complex A0 Induces Endoplasmic Reticulum Stress and Paraptotic Death in Human Cancer Cells, The Journal of Biological Chemistry, vol. 284, No. 36, 2009, pp. 24306-24319.
Taylor et al., Integrative Genomic Profiling of Human Prostate Cancer, Cancer Cell, vol. 18, No. 1, 2010, 23 pages.
Thayyullathil et al., ROS-Dependent Prostate Apoptosis Response-4 (Par-4) Up-Regulation and Ceramide Generation are the Prime Signaling Events Associated with Curcumin-Induced Autophagic Cell Death in Human Malignant Glioma, Federation of European Biochemical Societies Open Bio, vol. 4, Aug. 30, 2014, pp. 763-776.
Thuerauf et al., Effects of the Isoform-specific Characteristics of ATF6 Alpha and ATF6 Beta on Endoplasmic Reticulum Stress Response Gene Expression and Cell Viability, The Journal of Biological Chemistry, vol. 282, 2007, pp. 22865-22878.
Thuerauf et al., Opposing Roles for ATF6alpha and ATF6beta in Endoplasmic Reticulum Stress Response Gene Induction, The Journal of Biological Chemistry, vol. 279, No. 20, 2004, pp. 21078-21084.
Torres-Arzayus et al., High Tumor Incidence and Activation of the PI3K/AKT Pathway in Transgenic Mice Define AIB1 as an Oncogene, Cancer cell, vol. 6, No. 3, 2004, pp. 263-274.
Torres-Arzayus et al., Targeting the AIB1 Oncogene Through Mammalian Target of Rapamycin Inhibition in the Mammary Gland, Cancer Research, vol. 66, No. 23, 2006, pp. 11381-11388.
Ustundag et al., Proteasome Inhibition-induces Endoplasmic Reticulum Dysfunction and Cell Death of Human Cholangiocarcinoma Cells, World Journal of Gastroenterology, vol. 13, No. 6, Feb. 14, 2007, pp. 851-857.
Wang et al., Bufalin is a Potent Small Molecule Inhibitor of the Steroid Receptor Coactivators SRC-3 and SRC-1, Cancer Research, vol. 74, No. 5, Mar. 1, 2014, 21 pages.
Wang et al., Characterization of a Steroid Receptor Coactivator Small Molecule Stimulator that Overstimulates Cancer Cells and Leads to Cell Stress and Death, Cancer Cell, vol. 28, No. 2, Aug. 10, 2015, pp. 240-252.
Wang et al., Disruption of the SRC-1 Gene in Mice Suppresses Breast Cancer Metastasis Without Affecting Primary Tumor Formation, Proceedings of the National Academy of Sciences of the United States of America, vol. 106, No. 1, 2009, pp. 151-156.
Wang et al., Prognostic Significance of c-myc and AIB1 Amplification in Hepatocellular Carcinoma: a Broad Survey Using High-Throughput Tissue Microarray, Cancer, vol. 95, No. 11, Dec. 1, 2002, pp. 2346-2352.
Wang et al., Small Molecule Inhibition of the Steroid Receptor Coactivators, SRC-3 and SRC-1, Molecular Endocrinology, vol. 25, No. 12, Dec. 2011, 13 pages.
Wang et al., The Impact of the Unfolded Protein Response on Human Disease, The Journal of cell biology, vol. 197, No. 7, Jun. 25, 2012, pp. 857-867.
Wu et al., Selective Phosphorylations of the SRC-3/AIB1 Coactivator Integrate Genomic Reponses to Multiple Cellular Signaling Pathways, Molecular Cell, vol. 15, No. 6, 2004, pp. 937-949.
Xie et al., Correlation of AIB1 Overexpression with Advanced Clinical Stage of Human Colorectal Carcinoma, Human pathology, vol. 36, No. 7, 2005, pp. 777-783.
Xu et al., Normal and Cancer-Related Functions of the p160 Steroid Receptor Co-Activator (SRC) Family, Nature Reviews Cancer, vol. 9, No. 9, Sep. 2009, 32 pages.
Yan et al., Identification of Verrucarin A as a Potent and Selective Steroid Receptor Coactivator-3 Small Molecule Inhibitor, PLoS One, vol. 9, No. 4, Apr. 17, 2014, pp. 1-9.
Yan et al., Steroid Receptor Coactivator-3/AIB1 Promotes Cell Migration and Invasiveness Through Focal Adhesion Turnover and Matrix Metalloproteinase Expression, Cancer Research, vol. 68, No. 13, 2008, 19 pages.
Yi et al., SRC-3 Coactivator Regulates Cell Resistance to Cytotoxic Stress via TRAF4-Mediated p53 Destabilization, Genes & Development, vol. 27, No. 3, 2013, pp. 274-287.
Yoon et al., Simultaneous Mitochondrial Ca(2+) Overload and Proteasomal Inhibition are Responsible for the Induction of Paraptosis in Malignant Breast Cancer Cells, Cancer Letters, vol. 324, No. 2, 2012, pp. 197-209.
Yoon et al., Superoxide Anion and Proteasomal Dysfunction Contribute to Curcumin-induced Paraptosis of Malignant Breast Cancer Cells, Free Radical Biology & Medicine, vol. 48, No. 5, 2010, pp. 1-46.
York et al., Steroid Receptor Coactivator (SRC) Family: Masters of Systems Biology, Journal of Biological Chemistry, vol. 285, No. 50, Dec. 10, 2010, pp. 38743-38750.
Zhang et al., Curcumin Inhibits Endometriosis Endometrial Cells by Reducing Estradiol Production, Iranian Journal of Reproductive Medicine, vol. 11, No. 5, May 2013, pp. 415-422.
Zhao et al., Elevated Expression Levels of NCOA3, TOP1, and TFAP2C in Breast Tumors as Predictors of Poor Prognosis, Cancer, vol. 98, No. 1, Jul. 1, 2003, pp. 18-23.

\* cited by examiner

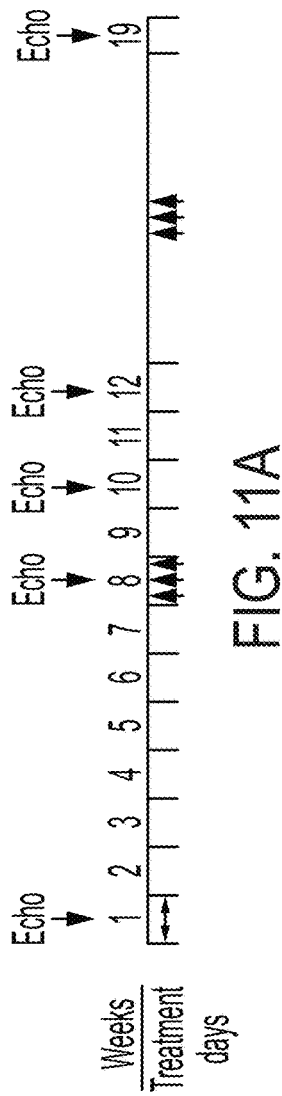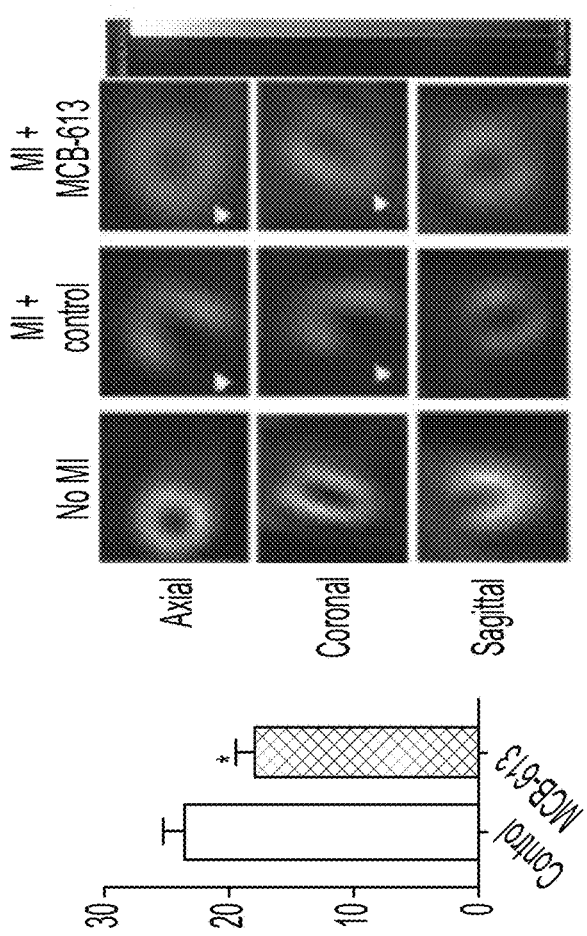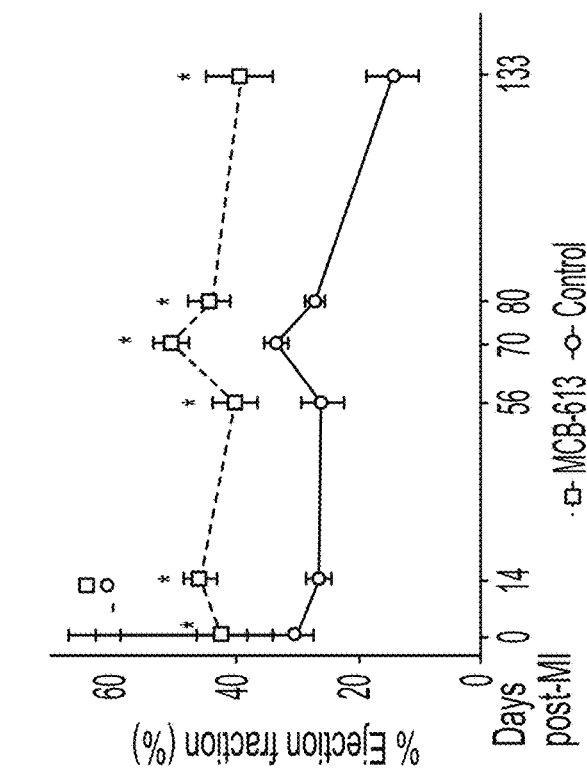
FIG. 11A
FIG. 11B
FIG. 11C
FIG. 11D

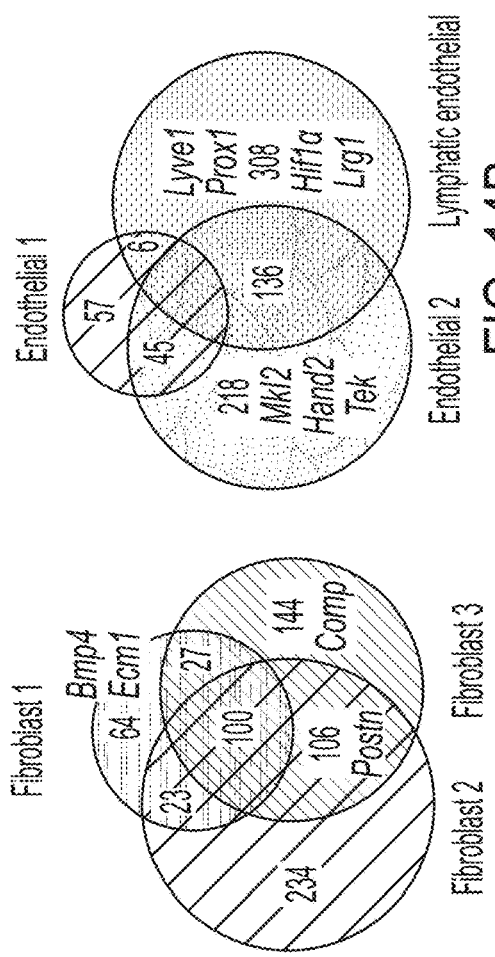
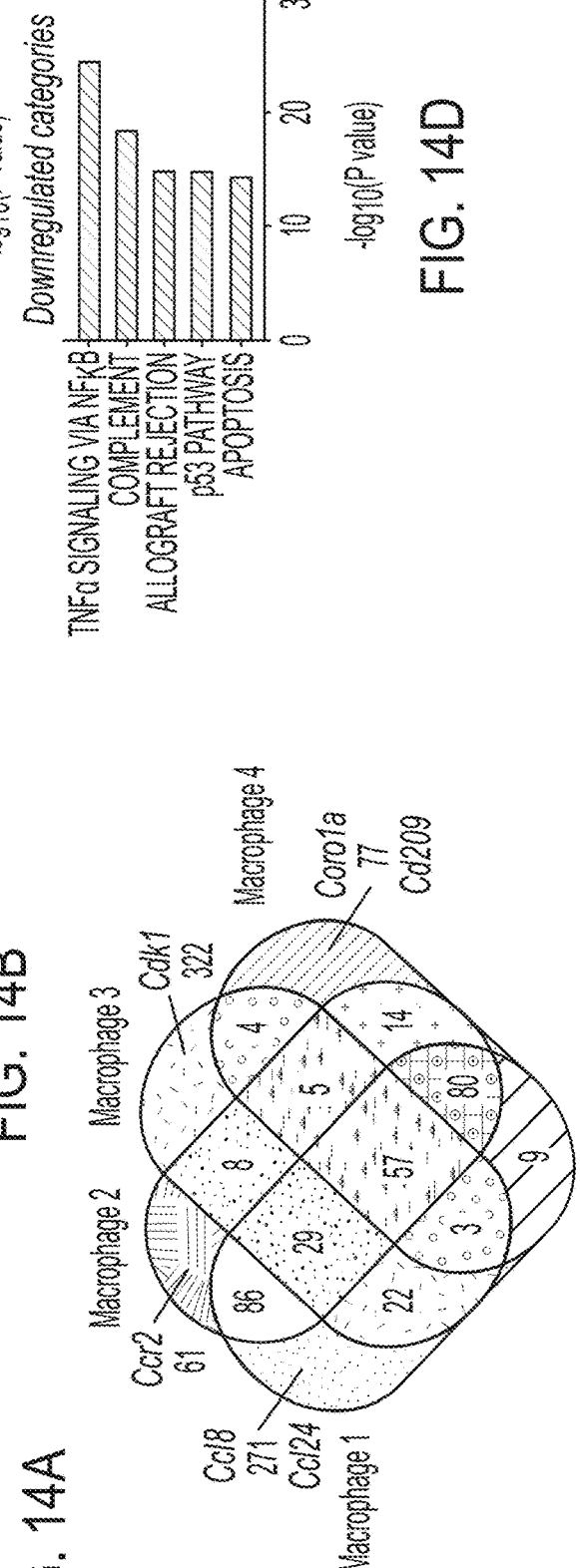
FIG. 14A
FIG. 14B
FIG. 14C
FIG. 14D

SMALL MOLECULE STIMULATORS OF STEROID RECEPTOR COACTIVATOR-3 AND METHODS OF THEIR USE AS CARDIOPROTECTIVE AND/OR VASCULAR REGENERATIVE AGENTS

CROSS-REFERENCE TO RELATED APPLICATIONS

This application is a continuation of U.S. patent application Ser. No. 16/554,733, filed Aug. 29, 2019, which claims priority to U.S. Provisional Application Nos. 62/724,281, filed Aug. 29, 2018, and 62/825,358, filed Mar. 28, 2019, which are incorporated herein by reference in their entireties.

BACKGROUND

A determinant of myocardial infarction (MI)-induced heart failure is a progressive remodeling of cardiac tissue that is associated with loss of myocytes, inflammation, fibrosis, and a major depression of cardiac ejection fraction. One promising therapeutic approach to improving cardiac function is prevention of detrimental remodeling of cardiac tissue in situ by directly preserving functional myocardium. A major hurdle to maintaining cardiac function after infarction includes the tissue destruction and the adult heart's limited and restricted regenerative potential, which poses a barrier to therapies designed to promote tissue reprogramming and repair.

SUMMARY

Described herein are small molecule stimulators of steroid receptor coactivator-3 (SRC-3) and methods of their use as cardioprotective and/or vascular regenerative agents. The compounds described herein are useful for promoting cardiac protection and repair and vascular regeneration after myocardial infarction. The methods include administering to a subject a compound as described herein.

Small molecule SRC-3 stimulators include compounds of the following formula:

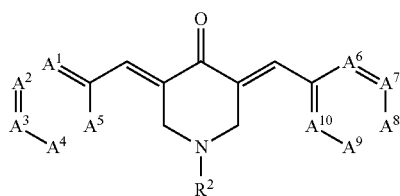

and pharmaceutically acceptable salts or prodrugs thereof. In these compounds, $A^1$, $A^2$, $A^3$, $A^4$, $A^5$, $A^6$, $A^7$, $A^8$, $A^9$, and $A^{10}$ are each independently selected from $CR^1$ and N, wherein each $R^1$ is hydrogen, halogen, alkoxy, cyano, trifluoromethyl, or substituted or unsubstituted $C_{1-6}$ alkyl; and $R^2$ is substituted or unsubstituted cycloalkyl or substituted or unsubstituted heterocycloalkyl. Optionally, the compound has the following formula:

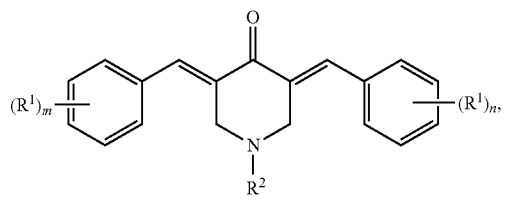

wherein m and n are each independently 1, 2, 3, 4, or 5.

Optionally, the compound has the following formula:

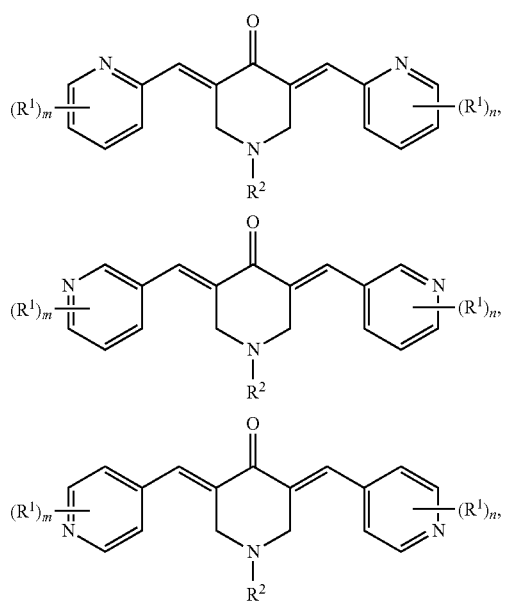

wherein m and n are each independently 1, 2, 3, or 4.

In the compounds described herein, $R^2$ is optionally selected from the group consisting of cyclopropyl, cyclobutyl, cyclopentyl, cyclohexyl, cycloheptyl, and cyclooctyl. Optionally, the compound is selected from the group consisting of:

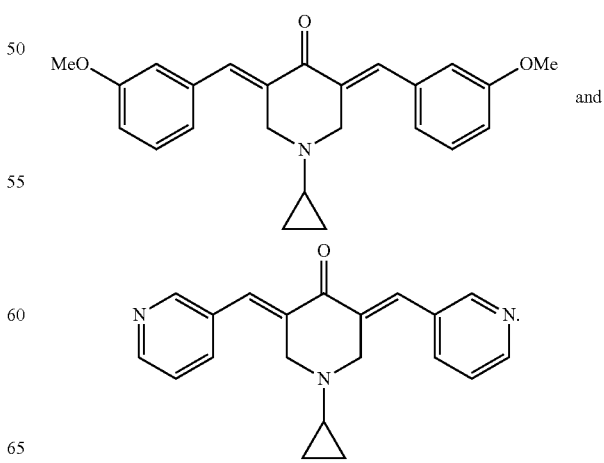

Optionally, the compound is selected from the group consisting of:

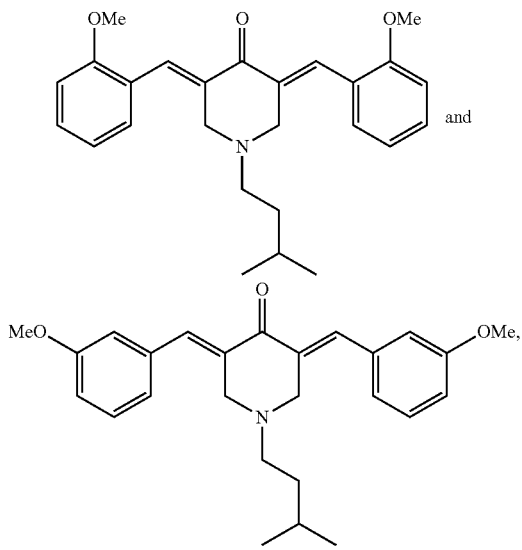

and or a pharmaceutically acceptable salt or prodrug thereof.

Also described herein are methods for treating an ischemic injury (e.g., a myocardial infarction or a stroke) in a subject, comprising administering to the subject an effective amount of a compound of the following formula:

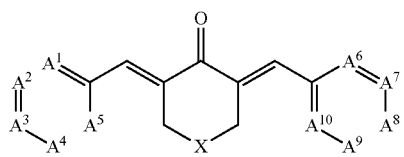

or a pharmaceutically acceptable salt or prodrug thereof. In the compounds for use in this method, $A^1$, $A^2$, $A^3$, $A^4$, $A^5$, $A^6$, $A^7$, $A^8$, $A^9$, and $A^{10}$ are each independently selected from $CR^1$ and N, wherein each $R^1$ is hydrogen, halogen, alkoxy, cyano, trifluoromethyl, or substituted or unsubstituted $C_{1-6}$ alkyl; and X is $NR^2$, $CR^3R^4$, or O, wherein $R^2$, $R^3$, and $R^4$ are each independently selected from the group consisting of hydrogen, substituted or unsubstituted $C_{1-6}$ alkyl, substituted or unsubstituted cycloalkyl, and substituted or unsubstituted heterocycloalkyl. Optionally, the compound is selected from the group consisting of:

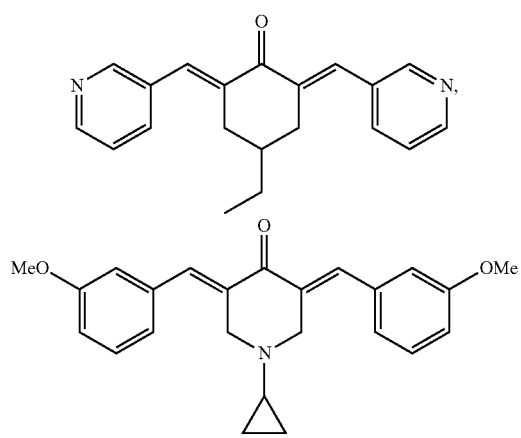

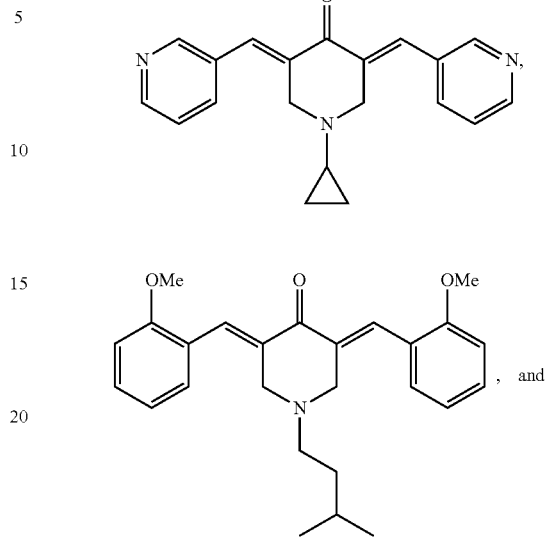

, and

Optionally, the method can further comprise selecting a subject who has suffered a myocardial infarction or who has suffered a stroke or other vascular impairments to the central nervous system.

Further described herein are methods of reducing a myocardial infarct size in a subject who has suffered a myocardial infarction. The method can comprise administering to the subject an effective amount of a compound of the following formula:

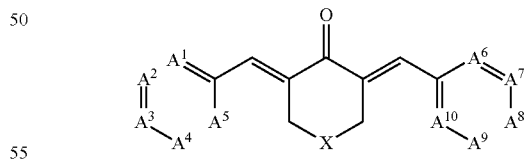

or a pharmaceutically acceptable salt or prodrug thereof. In the compounds for use in the methods described herein, $A^1$, $A^2$, $A^3$, $A^4$, $A^5$, $A^6$, $A^7$, $A^8$, $A^9$, and $A^{10}$ are each independently selected from $CR^1$ and N, wherein each $R^1$ is hydrogen, halogen, alkoxy, cyano, trifluoromethyl, or substituted or unsubstituted $C_{1-6}$ alkyl; and X is $NR^2$, $CR^3R^4$, or O, wherein $R^2$, $R^3$, and $R^4$ are each independently selected from the group consisting of hydrogen, substituted or unsubstituted $C_{1-6}$ alkyl, substituted or unsubstituted cycloalkyl, and substituted or unsubstituted heterocycloalkyl. Optionally, the compound is selected from the group consisting of:

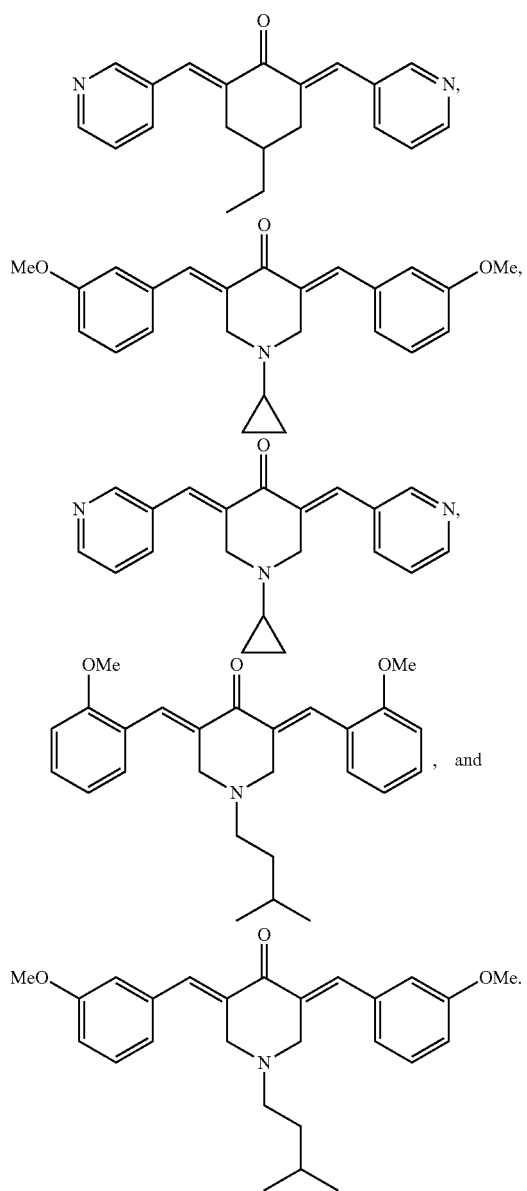

Optionally, the myocardial infarct size is reduced by at least 5% (e.g., by at least 15%) as compared to a myocardial infarct size in an untreated subject who has suffered a myocardial infarction.

Also described herein are methods of preventing or reducing cardiomyocyte loss, improving cardiac vascular perfusion, and/or improving central nervous system vascular perfusion in a subject who has suffered a myocardial infarction or stroke, comprising administering to the subject an effective amount of a compound of the following formula:

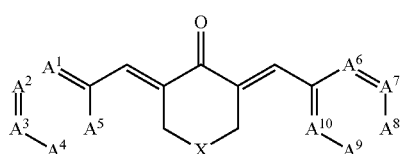

or a pharmaceutically acceptable salt or prodrug thereof. In the compounds for use in this method, $A^1$, $A^2$, $A^3$, $A^4$, $A^5$, $A^6$, $A^7$, $A^8$, $A^9$, and $A^{10}$ are each independently selected from $CR^1$ and N, wherein each $R^1$ is hydrogen, halogen, alkoxy, cyano, trifluoromethyl, or substituted or unsubstituted $C_{1-6}$ alkyl; and X is $NR^2$, $CR^3R^4$, or O, wherein $R^2$, $R^3$, and $R^4$ are each independently selected from the group consisting of hydrogen, substituted or unsubstituted $C_{1-6}$ alkyl, substituted or unsubstituted cycloalkyl, and substituted or unsubstituted heterocycloalkyl. Optionally, the compound is selected from the group consisting of:

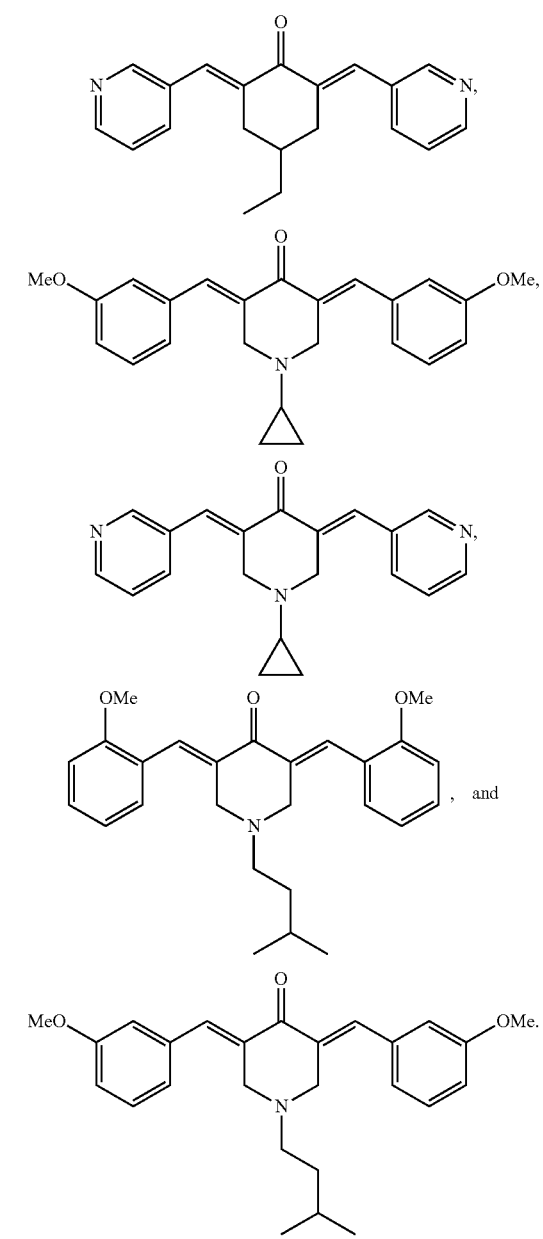

Also described herein are methods for improving cardiovascular function and/or central nervous system vascular function in a subject, comprising administering to the subject an effective amount of a compound of the following formula:

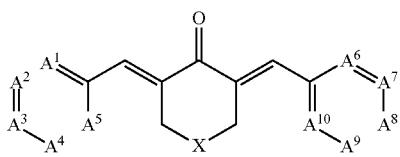

or a pharmaceutically acceptable salt or prodrug thereof. In the compounds for use in this method, A, $A^2$, $A^3$, $A^4$, $A^5$, $A^6$, $A^7$, $A^8$, $A^9$, and $A^{10}$ are each independently selected from $CR^1$ and N, wherein each $R^1$ is hydrogen, halogen, alkoxy, cyano, trifluoromethyl, or substituted or unsubstituted $C_{1-6}$ alkyl; and X is $NR^2$, $CR^3R^4$, or O, wherein $R^2$, $R^3$, and $R^4$ are each independently selected from the group consisting of hydrogen, substituted or unsubstituted $C_{1-6}$ alkyl, substituted or unsubstituted cycloalkyl, and substituted or unsubstituted heterocycloalkyl. Optionally, the compound is selected from the group consisting of:

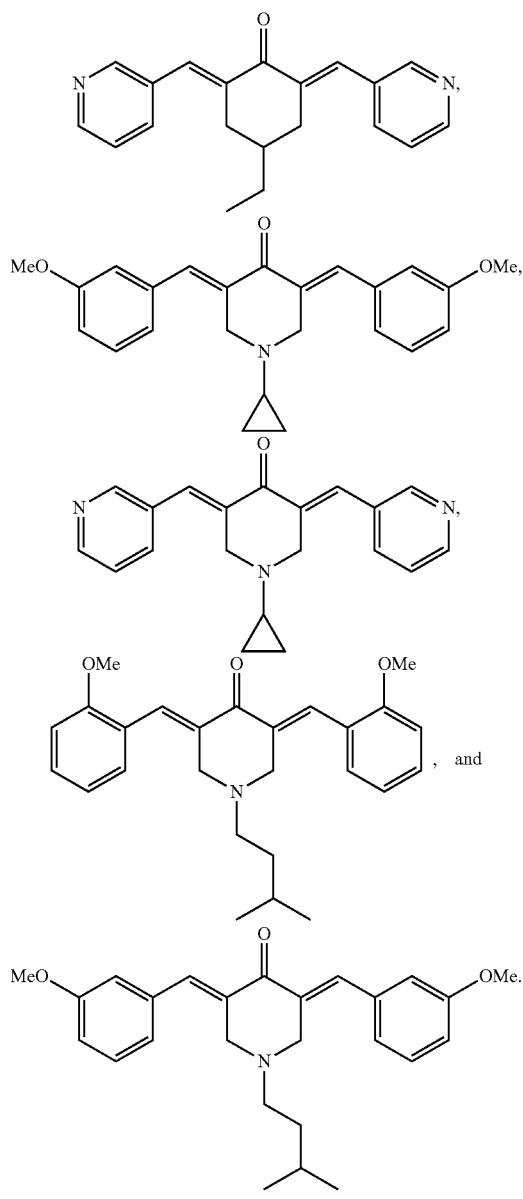

Optionally, the subject has suffered an ischemic injury (e.g., a myocardial infarction or stroke). Optionally, the subject is an elderly subject.

Also described herein are methods for promoting wound healing in a subject, comprising administering to the subject an effective amount of a compound of the following formula:

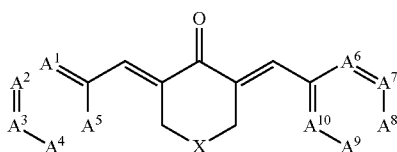

or a pharmaceutically acceptable salt or prodrug thereof. In the compounds for use in this method, $A^1$, $A^2$, $A^3$, $A^4$, $A^5$, $A^6$, $A^7$, $A^8$, $A^9$, and $A^{10}$ are each independently selected from $CR^1$ and N, wherein each $R^1$ is hydrogen, halogen, alkoxy, cyano, trifluoromethyl, or substituted or unsubstituted $C_{1-6}$ alkyl; and X is $NR^2$, $CR^3R^4$, or O, wherein $R^2$, $R^3$, and $R^4$ are each independently selected from the group consisting of hydrogen, substituted or unsubstituted $C_{1-6}$ alkyl, substituted or unsubstituted cycloalkyl, and substituted or unsubstituted heterocycloalkyl. Optionally, the compound is selected from the group consisting of:

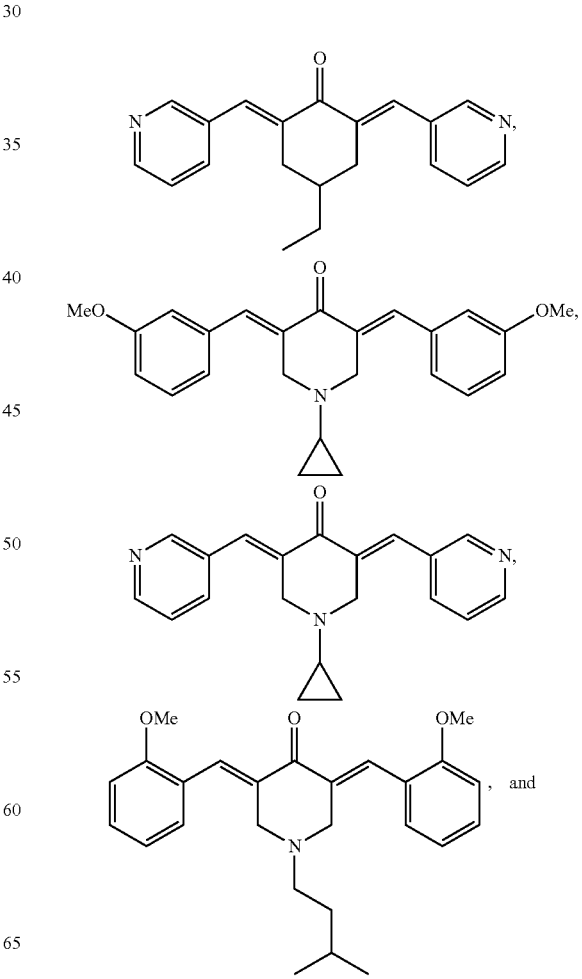

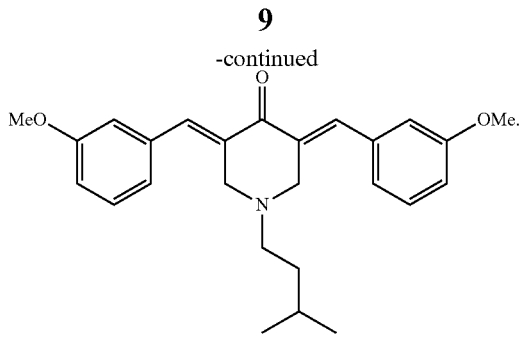

Optionally, the subject has suffered an ischemic injury (e.g., a myocardial infarction or stroke). Optionally, the subject is an elderly subject.

Further described herein are methods for treating or preventing hypertrophic cardiomyopathy in a subject, comprising administering to the subject an effective amount of a compound of the following formula:

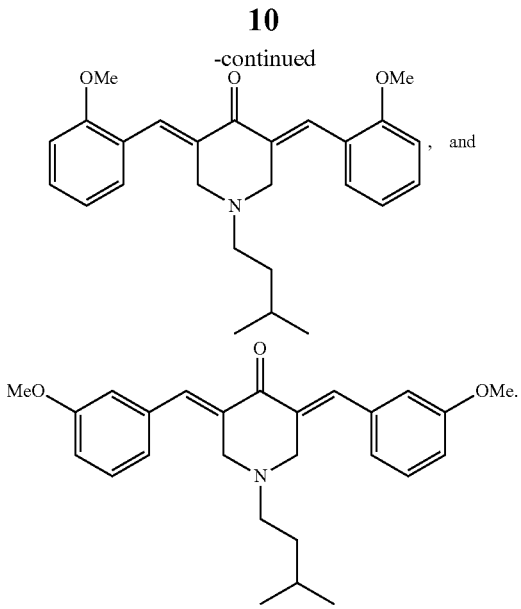

or a pharmaceutically acceptable salt or prodrug thereof. In the compounds for use in this method, $A^1$, $A^2$, $A^3$, $A^4$, $A^5$, $A^6$, $A^7$, $A^8$, $A^9$, and $A^{10}$ are each independently selected from CR and N, wherein each $R^1$ is hydrogen, halogen, alkoxy, cyano, trifluoromethyl, or substituted or unsubstituted $C_{1-6}$ alkyl; and X is $NR^2$, $CR^3R^4$, or O, wherein $R^2$, $R^3$, and $R^4$ are each independently selected from the group consisting of hydrogen, substituted or unsubstituted $C_{1-6}$ alkyl, substituted or unsubstituted cycloalkyl, and substituted or unsubstituted heterocycloalkyl. Optionally, the compound is selected from the group consisting of:

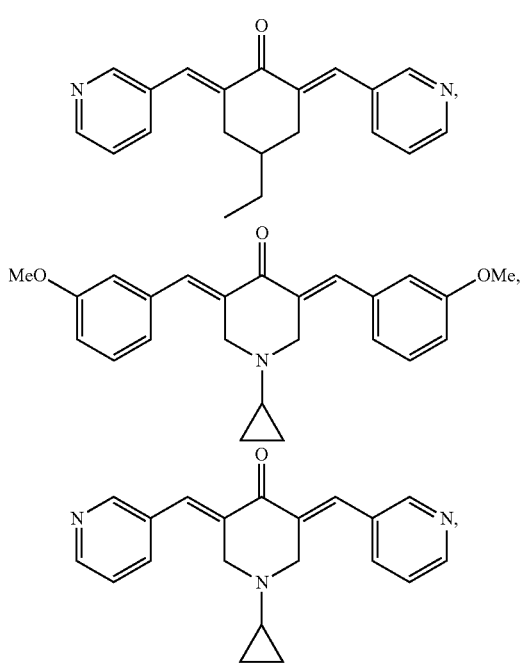

Optionally, the subject has suffered an ischemic injury (e.g., a myocardial infarction or stroke).

The details of one or more embodiments are set forth in the drawings and the description below. Other features, objects, and advantages will be apparent from the description and drawings, and from the claims.

DESCRIPTION OF DRAWINGS

FIG. 7, middle panel shows that Compound 10-1 selectively stimulates the intrinsic transcriptional activity of SRCs. FIG. 7, bottom panel shows that Compound 10-2 selectively stimulates the intrinsic transcriptional activity of SRCs.

FIG. 10E shows representative images of infarct border zones from three control mice and three mice treated with MCB-613. FIG. 10E also contains a bar graph showing the quantification CD31 immuno-stain density per area of tissue for two fields per border zone *P<0.05.

FIGS. 11A-11G show that MCB-613 improves cardiac function following myocardial infarction. FIG. 11A is a schematic representation of experimental procedures. Mice were treated with MCB-613 or control two hours after permanent ligation of the left anterior descending coronary artery and for six additional days and at weeks eight and 16 as indicated. For FIG. 11, ejection fraction was measured by echocardiography at the indicated times and hearts were harvested at 24 hours and 12 weeks. *P<0.05. For FIG. 11C, heart weights were compared to tibia length 12 weeks post-MI. FIG. 11D shows a representative image of a center slice of a mouse heart in axial (short axis), coronal (long axis), and sagittal views showing differences in morphology and $^{18}$F-FDG uptake between control (no MI), MI, and MI plus MCB-613 at two weeks post-MI. The arrow indicates the infarct zone. n=6 control no MI, n=6 MI plus vehicle control, n=4 MI plus MCB-613. For FIG. 11E, MCB-613-treated hearts (n=2; infarct sizes 44% and 31%) and MCB-613-treated hearts at 12 weeks (n=4; infarct sizes 22%, 3%, 20% and 14%) were fixed and stained with Picrosirus red. FIG. 11E also contains a bar graph showing the quantification of percent fibrosis at the border zones of each heart. Scale bars: 2000 μm and 20 μm. FIG. 11F shows representative electron micrographs of border area 72 hours post-MI. My=myofibrils. Mi=mitochondria. Scale bar=1 μm. FIG. 11G, shows representative TUNEL staining from control and MCB-613 treated hearts 24 hours post-MI. n=4 hearts per group. Scale bars: 2000 μm and 20 μm.

FIG. 13A is a schematic representation of isolation procedures to obtain cardiomyocytes for total RNA-sequencing and non-cardiomyocytes for single-cell RNA-seq analysis from control treated and MCB-613 treated mice 12 weeks post-MI. n=2 hearts/group. FIG. 13B is a heat map analysis of genes identified by RNA-seq and differentially expressed in cardiomyocytes from two mice treated with MCB-613 versus two mice treated with saline 10 weeks post-MI. FIG. 13C is a gene set enrichment analysis of upregulated and downregulated genes in cardiomyocytes of MCB-613 versus control treated hearts. FIG. 13D depicts cell populations identified by unsupervised clustering. Each dot indicates a single cell. FIG. 13E is a heat map that indicates established cell type markers used to specifically identify each cluster. FIG. 13F shows representative TUNEL staining from control and MCB-613 treated hearts 24 hours post-MI. n=4 hearts per group. Scale bars: 2000 μm and 20 μm.

FIG. 14A is a Venn analysis of fibroblasts cluster gene expression. FIG. 14B is a Venn analysis of endothelial cluster gene expression. FIG. 14C is a Venn analysis of macrophage gene expression. FIG. 14D is a gene set enrichment analysis of upregulated and downregulated genes in granulocytes of MCB-613 over control-treated hearts.

FIG. 15A shows the number of up- and down-regulated genes in non-myocyte cells from control mice compared to MCB-613 treated mice. FIG. 15B contains a receptor-ligand analysis of intercellular communication between cardiac cell types excluding cardiomyocytes. The lines indicate communication between the two cell types. The directionality of the ligand-receptor pairing begins at the node and ends at the cognate receptor as illustrated in the figure legend. The thickness of the line reflects the number of ligand-receptor pairings. The loops represent autocrine signaling circuits. FIG. 15C is a heat map of ligand-receptor pairings between granulocytes, fibroblast clusters and macrophage $C_4$. FIG. 15D is a heat map showing top 50 up and down-regulated drug-responsive genes for 277 and 310 granulocytes from control and MCB-613-treated hearts, respectively.

FIG. 16A shows the quantification of cardiac immune cells by fluorescence-activated cell sorting (FACS) immune phenotyping analysis 24 hours post-MI from control and MCB-613 treated mice. FIG. 16B shows mRNA expression in granulocytes and neutrophils isolated from bone marrow 24 hours post MI and MCB 613 treatment. Total RNA was isolated from neutrophil enriched and neutrophil depleted fractions of bone marrow and converted to cDNA. Gene expression changes in S100a9, Tlr7 and Lcn2 were measured by qPCR and 18s RNA expression was used as a control. N=6 each group *P<0.05. FIG. 16C shows representative LYZ staining from control and MCB-613 treated hearts 24 hours after MI. The top panels of FIG. 16C show a low magnification from endocardium to epicardium and the bottom panels show a high magnification of sub-endocardial regions. The arrows indicate LYZ+ cells. The bar graph in FIG. 16C shows the quantification of LV density of LYZ+ cells. n=3 hearts/group, >10 mm² imaged/heart, 24 hours after MI surgery *P<0.039.

DETAILED DESCRIPTION

Figure 1:
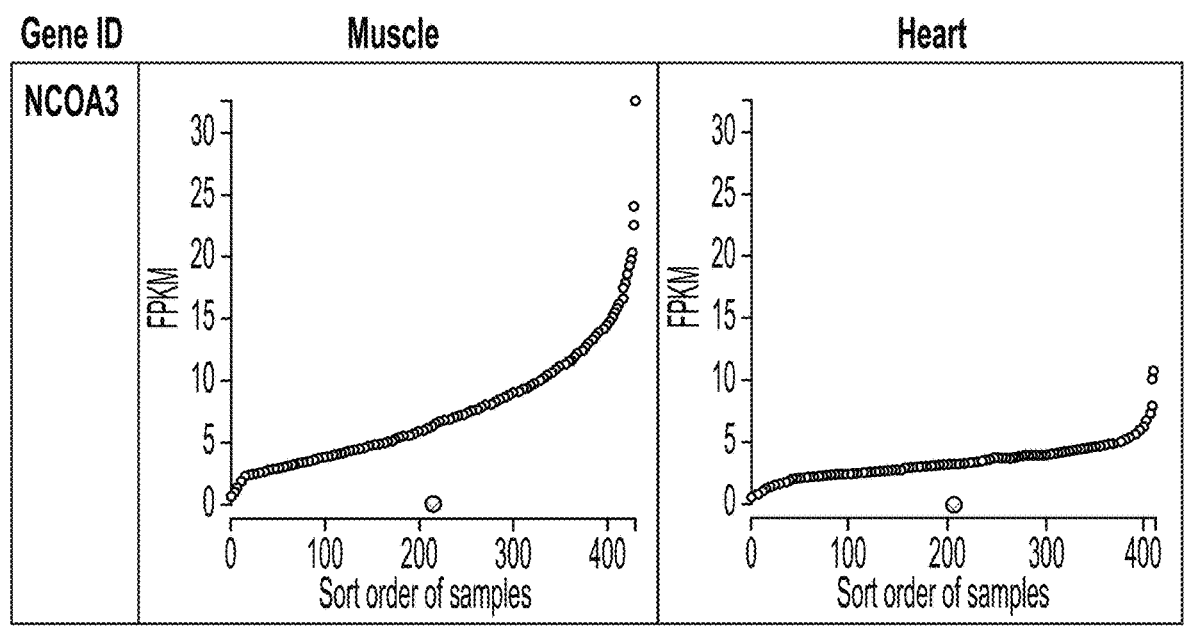
FIG. 1 contains graphs showing the expression of NCOA3 in normal human hearts (left panel) and in muscle tissues (right panel).

Described herein are stimulators of steroid receptor coactivator (SRC) proteins and methods for their use. Steroid receptor coactivators are members of the p160 family of nuclear receptor coactivators and include SRC-1, SRC-2 (TIF2/GRIP1), and SRC-3 (AIB1/RAC3/ACTR/pCIP). The small molecules described herein are stimulators of SRC-3 and are useful as cardioprotective and/or vascular regenerative agents. In particular, the compounds are useful for promoting cardiac protection and repair and vascular regeneration after myocardial infarction or stroke. The compounds are also useful in preventing cardiac hypertrophy and collagen deposition and improving cardiac post-infarction function. The compounds have been demonstrated to increase angiogenesis, increase vascular perfusion in the heart and central nervous system, and promote cardiac beta oxidation. Administration of the compounds described herein also significantly decreases the presence of methylglutaryl carnitine, a metabolite associated with dilated cardiomyopathy.

I. Compounds

A class of SRC stimulators described herein is represented by Formula I

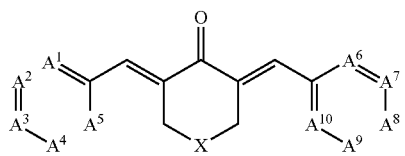

and pharmaceutically acceptable salts or prodrugs thereof.

In Formula I, $A^1$, $A^2$, $A^3$, $A^4$, $A^5$, $A^6$, $A^7$, $A^8$, $A^9$, and $A^{10}$ are each independently selected from $CR^1$ and N. Each $R^1$ group present in Formula I is independently selected from hydrogen, halogen, alkoxy, cyano, trifluoromethyl, and substituted or unsubstituted $C_{1-6}$ alkyl.

Also, in Formula I, X is $NR^2$, $CR^3R^4$, or O, wherein $R^2$, $R^3$, and $R^4$ are each independently selected from the group consisting of hydrogen, substituted or unsubstituted $C_{1-6}$ alkyl, substituted or unsubstituted cycloalkyl, and substituted or unsubstituted heterocycloalkyl.

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_3$-$C_{20}$ cycloalkenyl, and $C_3$-$C_{20}$ cycloalkynyl. Additional ranges of these groups useful with the compounds and methods described herein include $C_5$-$C_{12}$ cycloalkyl, $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{20}$ heterocycloalkyl, $C_3$-$C_{20}$ heterocycloalkenyl, and $C_3$-$C_{20}$ heterocycloalkynyl. Additional ranges of these groups useful with the compounds and methods described herein include $C_5$-$C_{12}$ heterocycloalkyl, $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline. The aryl and heteroaryl molecules can be attached at any position on the ring, unless otherwise noted.

The term alkoxy as used herein is an alkyl group bound through a single, terminal ether linkage. Likewise, the term aryloxy as used herein is an aryl group bound through a single, terminal ether linkage.

The term hydroxyl as used herein is represented by the formula —OH.

The terms amine or amino as used herein are represented by the formula —$NZ^1Z^2$, where $Z^1$ and $Z^2$ can each be a substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The alkoxy, aryloxy, amino, alkyl, alkenyl, alkynyl, aryl, heteroalkyl, heteroalkenyl, heteroalkynyl, heteroaryl, cycloalkyl, or heterocycloalkyl molecules used herein can be substituted or unsubstituted. As used herein, the term substituted includes the addition of an alkoxy, aryloxy, amino, alkyl, alkenyl, alkynyl, aryl, heteroalkyl, heteroalkenyl, heteroalkynyl, heteroaryl, cycloalkyl, or heterocycloalkyl group to a position attached to the main chain of the alkoxy, aryloxy, amino, alkyl, alkenyl, alkynyl, aryl, heteroalkyl, heteroalkenyl, heteroalkynyl, heteroaryl, cycloalkyl, or heterocycloalkyl, e.g., the replacement of a hydrogen by one of these molecules. Examples of substitution groups include, but are not limited to, hydroxyl, halogen (e.g., F, Br, Cl, or I), and carboxyl groups. Conversely, as used herein, the term unsubstituted indicates the alkoxy, aryloxy, amino, alkyl, alkenyl, alkynyl, aryl, heteroalkyl, heteroalkenyl, heteroalkynyl, heteroaryl, cycloalkyl, or heterocycloalkyl has a full complement of hydrogens, i.e., commensurate with its saturation level, with no substitutions, e.g., linear decane (—(CH$_2$)$_9$—CH$_3$).

In some examples, Formula I is represented by Structure I-A:

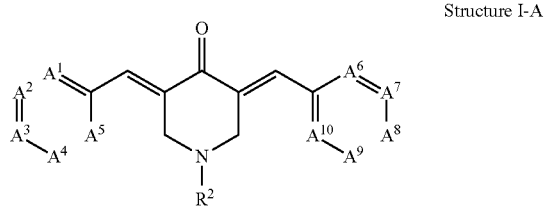

Structure I-A

In Structure I-A, A, A$^2$, A$^3$, A$^4$, A$^5$, A$^6$, A$^7$, A, A$^9$, A$^{10}$, and R$^2$ are as defined above for Formula I. In some examples of Structure I-A, each of A$^1$, A$^2$, A$^3$, A$^4$, A$^5$, A$^6$, A$^7$, A$^8$, A$^9$, and A$^{10}$ are CR$^1$, where each R is independently selected from a group as defined above for Formula I. For example, the compound of Structure I-A can be represented by Structure I-A1:

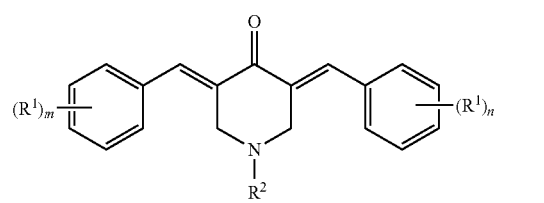

Structure I-A1

In Structure I-A1, m and n are each independently 1, 2, 3, 4, or 5. In other words, the phenyl rings of the molecule can include from one to five R groups. Each of the R groups can be independently selected from a group as defined above for Formula I.

In some examples of Structure I-A, one or more of A, A$^2$, A$^3$, A$^4$, A$^5$, A$^6$, A$^7$, A$^8$, A$^9$, and A$^{10}$ can be N. For example, the compound of Structure I-A can be represented by Structure I-A2 Structure I-A3, or Structure I-A4:

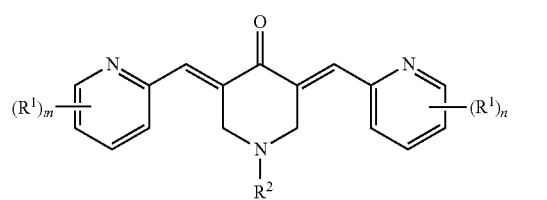

Structure I-A2

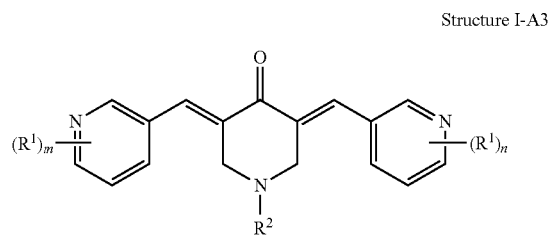

Structure I-A3

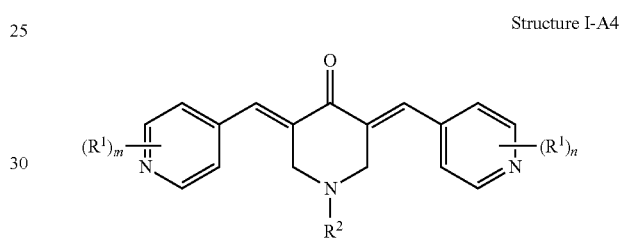

Structure I-A4

In Structure I-A2, Structure I-A3, and Structure I-A4, m and n are each independently 1, 2, 3, or 4. In other words, the phenyl rings of the molecule can include from one to four R$^1$ groups. Each of the R$^1$ groups can be independently selected from a group as defined above for Formula I.

Optionally, in Structure I-A1, Structure I-A2, Structure I-A3, and/or Structure I-A4, R$^2$ is substituted or unsubstituted cycloalkyl or substituted or unsubstituted heterocycloalkyl. In some examples, R$^2$ is selected from the group consisting of cyclopropyl, cyclobutyl, cyclopentyl, cyclohexyl, cycloheptyl, and cyclooctyl.

In some examples, Formula I is represented by Structure I-B:

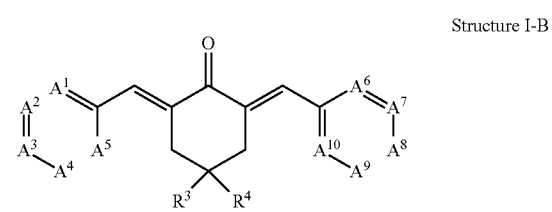

Structure I-B

In Structure I-B, A$^1$, A$^2$, A$^3$, A$^4$, A$^5$, A$^6$, A$^7$, A$^8$, A$^9$, A$^{10}$, R$^3$, and R$^4$ are as defined above for Formula I. In some examples of Structure I-B, each of A$^1$, A$^2$, A$^3$, A$^4$, A$^5$, A$^6$, A$^7$, A$^8$, A$^9$, and A$^{10}$ are CR$^1$, where each R$^1$ is independently selected from a group as defined above for Formula I. For example, the compound of Structure I-B can be represented by Structure I-B1:

Structure I-B1

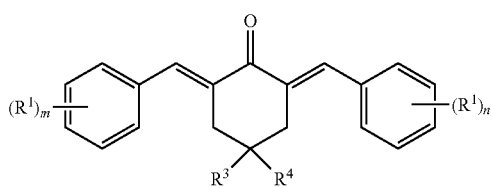

In Structure I-B1, m and n are each independently 1, 2, 3, 4, or 5. In other words, the phenyl rings of the molecule can each independently include from one to five $R^1$ groups. Each of the $R^1$ groups can be independently selected from a group as defined above for Formula I.

In some examples of Structure I-B, one or more of $A^1$, $A^2$, $A^3$, $A^4$, $A^5$, $A^6$, $A^7$, $A^8$, $A^9$, and $A^{10}$ can be N. For example, the compound of Structure I-B can be represented by Structure I-B2, Structure I-B3, or Structure I-B4:

Structure I-B2

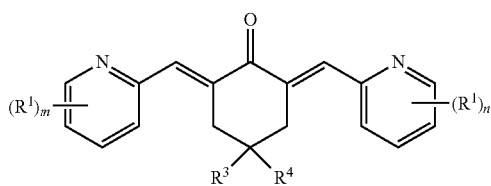

Structure I-B3

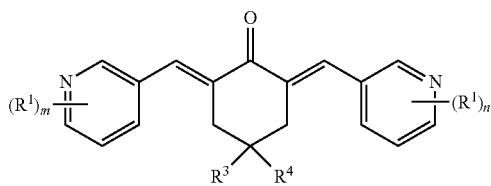

Structure I-B4

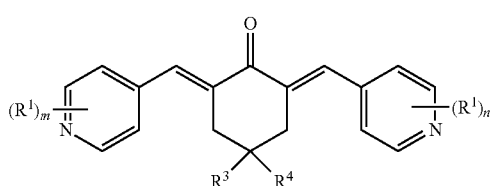

In Structure I-B2, Structure I-B3, and Structure I-B4, m and n are each independently 1, 2, 3, or 4. In other words, the phenyl rings of the molecule can each independently include from one to four $R^1$ groups. Each of the $R^1$ groups can be independently selected from a group as defined above for Formula I.

In some examples, Formula I is represented by Structure I-C:

Structure I-C

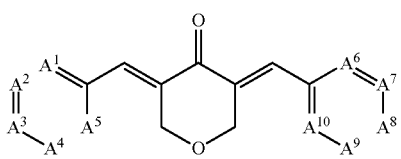

In Structure I-C, $A^1$, $A^2$, $A^3$, $A^4$, $A^5$, $A^6$, $A^7$, $A^8$, $A^9$, and $A^{10}$ are as defined above for Formula I. In some examples of Structure I-C, each of $A^1$, $A^2$, $A^3$, $A^4$, $A^5$, $A^6$, $A^7$, $A^8$, $A^9$, and $A^{10}$ are $CR^1$, where each $R^1$ is independently selected from a group as defined above for Formula I. For example, the compound of Structure I-C can be represented by Structure I-C1:

Structure I-C1

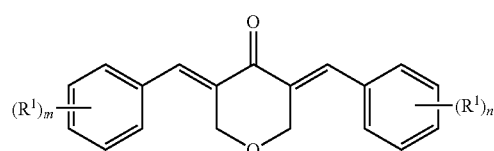

In Structure I-$C_1$, m and n are each independently 1, 2, 3, or 4. In other words, the phenyl rings of the molecule can each independently include from one to four $R^1$ groups. Each of the $R^1$ groups can be independently selected from a group as defined above for Formula I.

In some examples of Structure I-C, one or more of $A^1$, $A^2$, $A^3$, $A^4$, $A^5$, $A^6$, $A^7$, $A^8$, $A^9$, and $A^{10}$ can be N. For example, the compound of Structure I-C can be represented by Structure I-C2, Structure I-C3, or Structure I-C4:

Structure I-C2

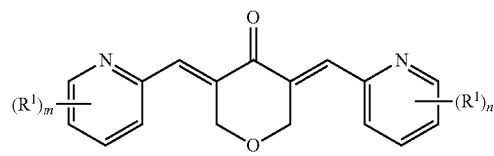

Structure I-C3

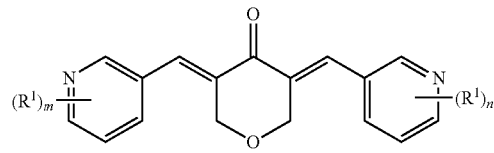

Structure I-C4

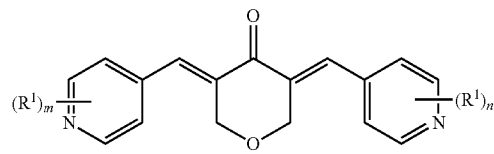

In Structure I-C2, Structure I-C3, and Structure I-C4, m and n are each independently 1, 2, 3, or 4. In other words, the phenyl rings of the molecule can each independently include from one to four $R^1$ groups. Each of the $R^1$ groups can be independently selected from a group as defined above for Formula I.

Examples of Formula I include the following compounds:
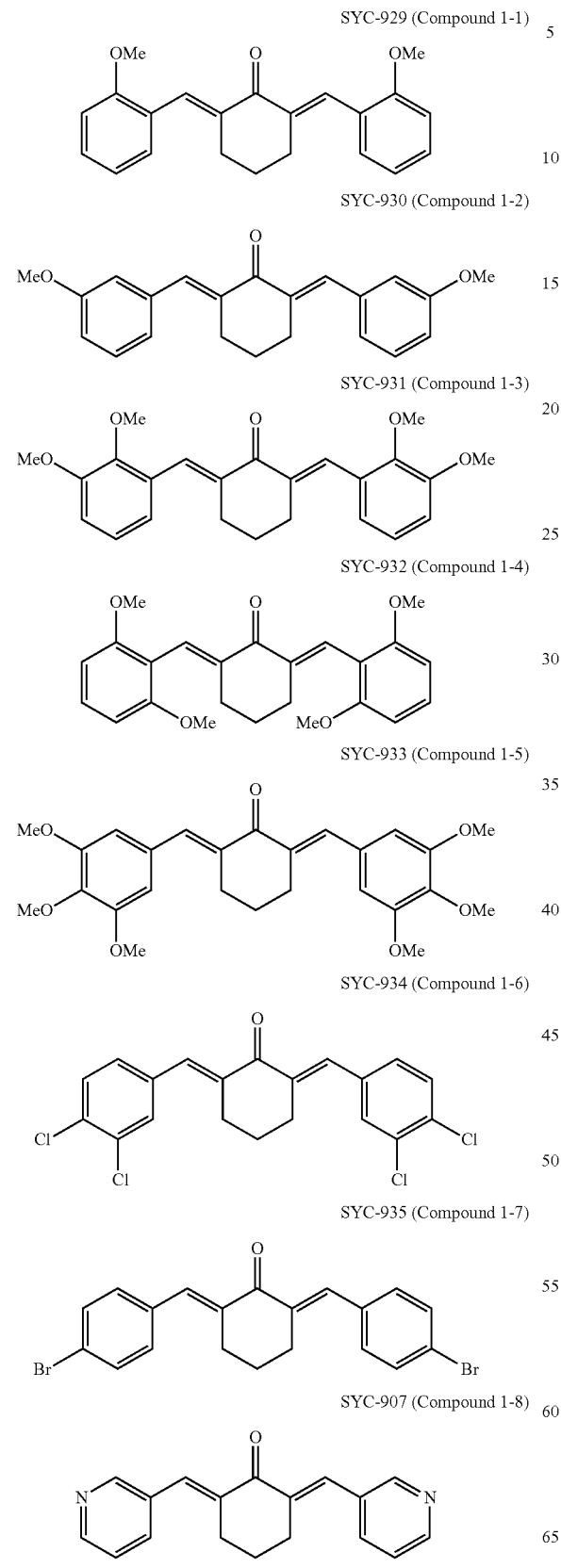

SYC-943 (Compound 2-7)
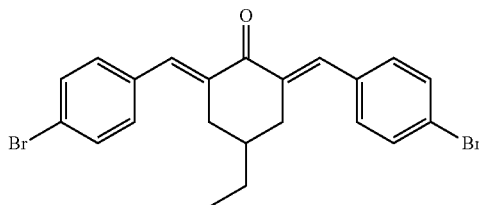
SYC-944 (Compound 2-8) (or MCB-613)
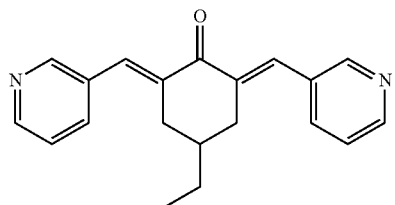
SYC-908 (Compound 2-9)
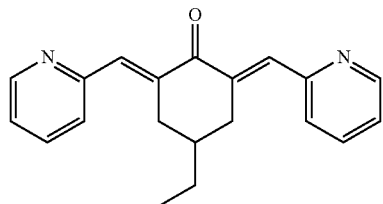
SYC-945 (Compound 3-1)
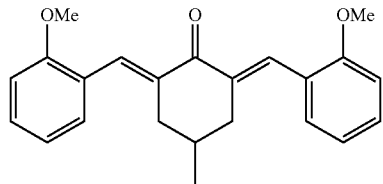
SYC-946 (Compound 3-2)
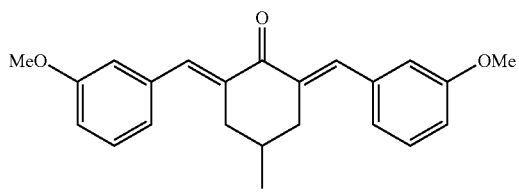
SYC-947 (Compound 3-3)
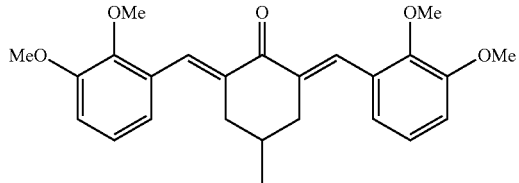
SYC-948 (Compound 3-4)
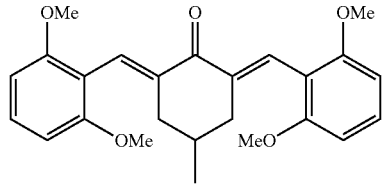
SYC-949 (Compound 3-5)
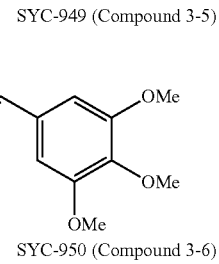
SYC-950 (Compound 3-6)
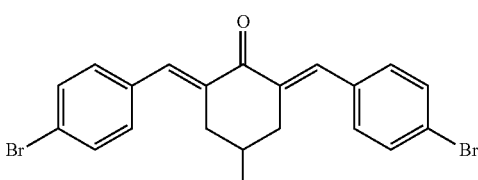
SYC-951 (Compound 3-7)
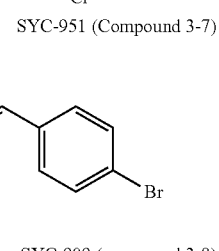
SYC-909 (compound 3-8)
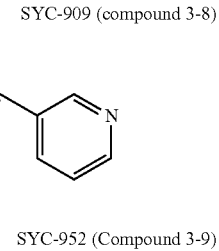
SYC-952 (Compound 3-9)
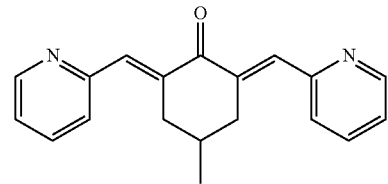
SYC-849 (Compound 4-1)
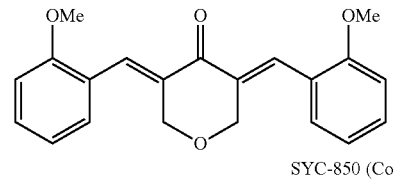
SYC-850 (Compound 4-2)
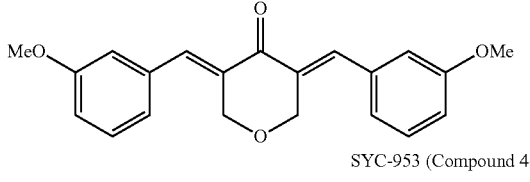
SYC-953 (Compound 4-3)
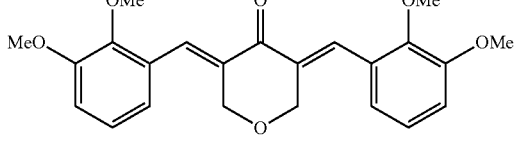

-continued
SYC-954 (Compound 4-4)
SYC-910 (Compound 4-5)
SYC-955 (Compound 4-6)
SYC-956 (Compound 4-7)
SYC-851 (Compound 4-8)
SYC-957 (Compound 4-9)
SYC-852 (Compound 5-1)
SYC-958 (Compound 5-2)
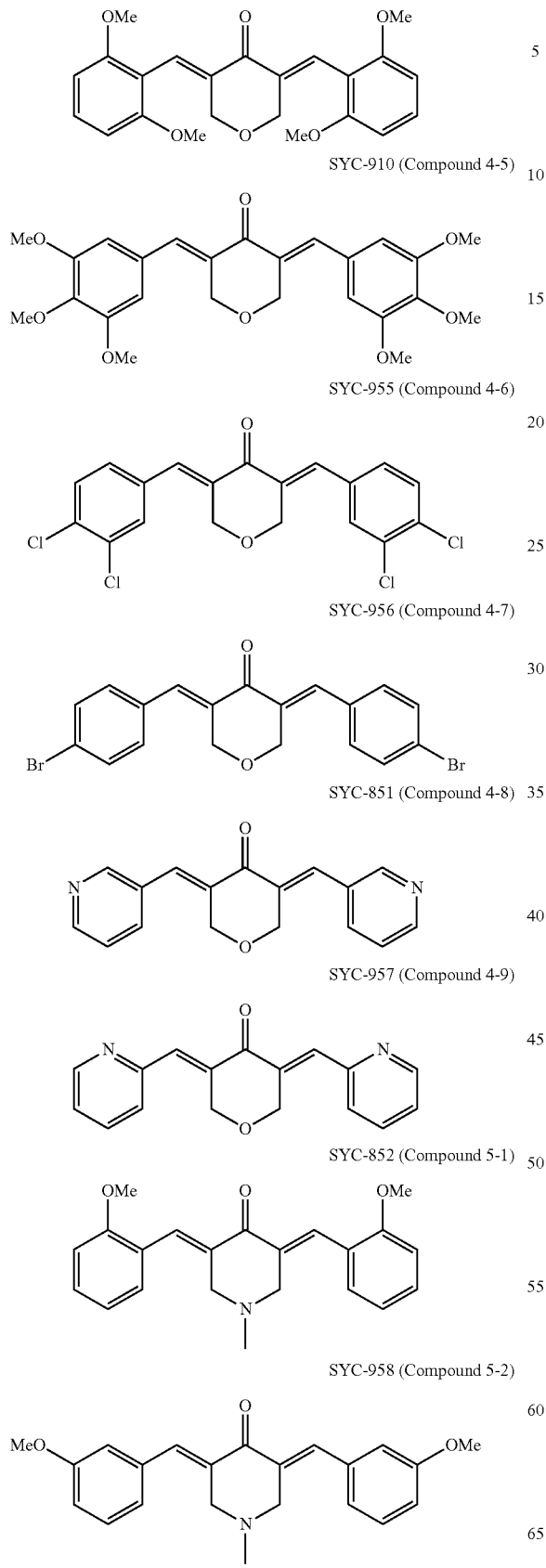
-continued
SYC-911 (Compound 5-3)
SYC-853 (Compound 5-4)
SYC-912 (Compound 5-5)
SYC-959 (Compound 5-6)
SYC-960 (Compound 5-7)
SYC-928 (Compound 5-8)
SYC-913 (Compound 5-9)
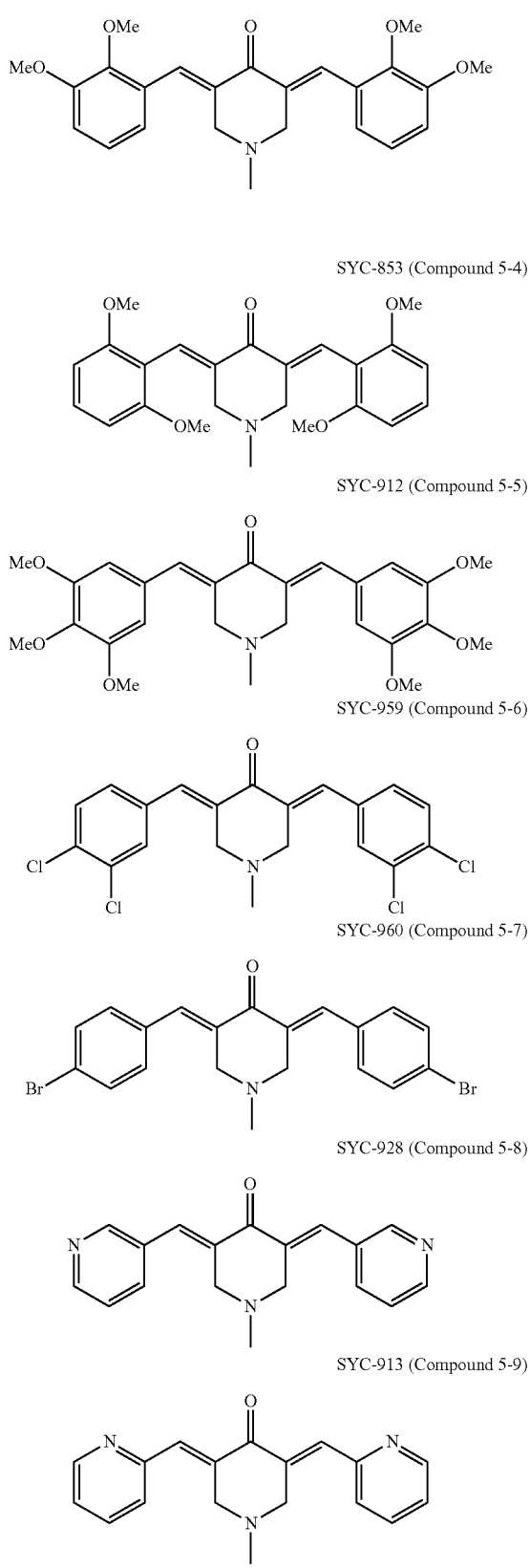

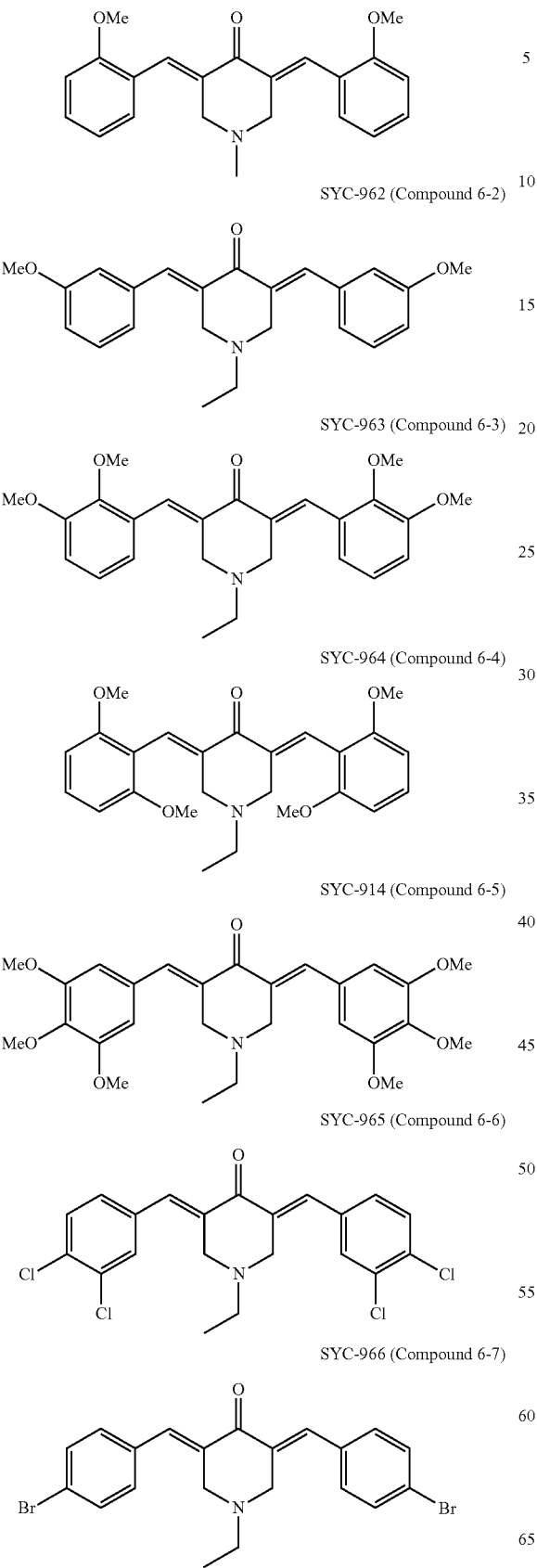
SYC-961 (Compound 6-1)
SYC-962 (Compound 6-2)
SYC-963 (Compound 6-3)
SYC-964 (Compound 6-4)
SYC-914 (Compound 6-5)
SYC-965 (Compound 6-6)
SYC-966 (Compound 6-7)
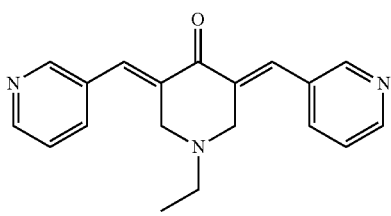
SYC-854 (Compound 6-8)
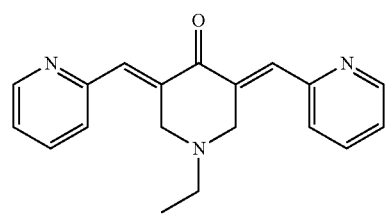
SYC-915 (Compound 6-9)
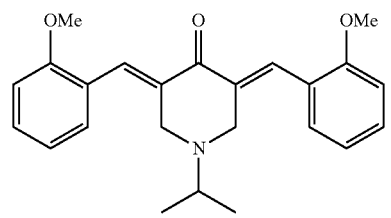
SYC-967 (Compound 7-1)
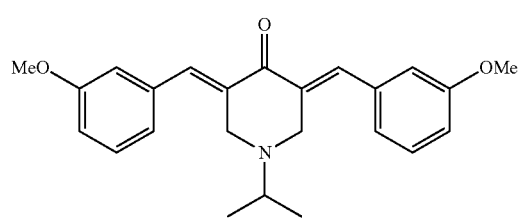
SYC-968 (Compound 7-2)
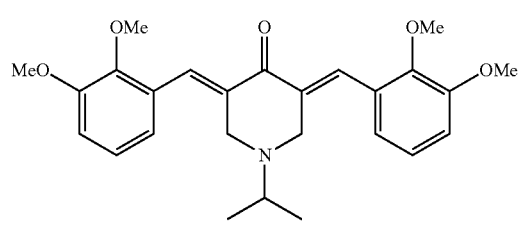
SYC-920 (Compound 7-3)
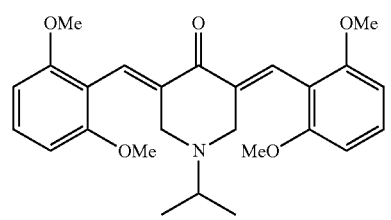
SYC-969 (Compound 7-4)

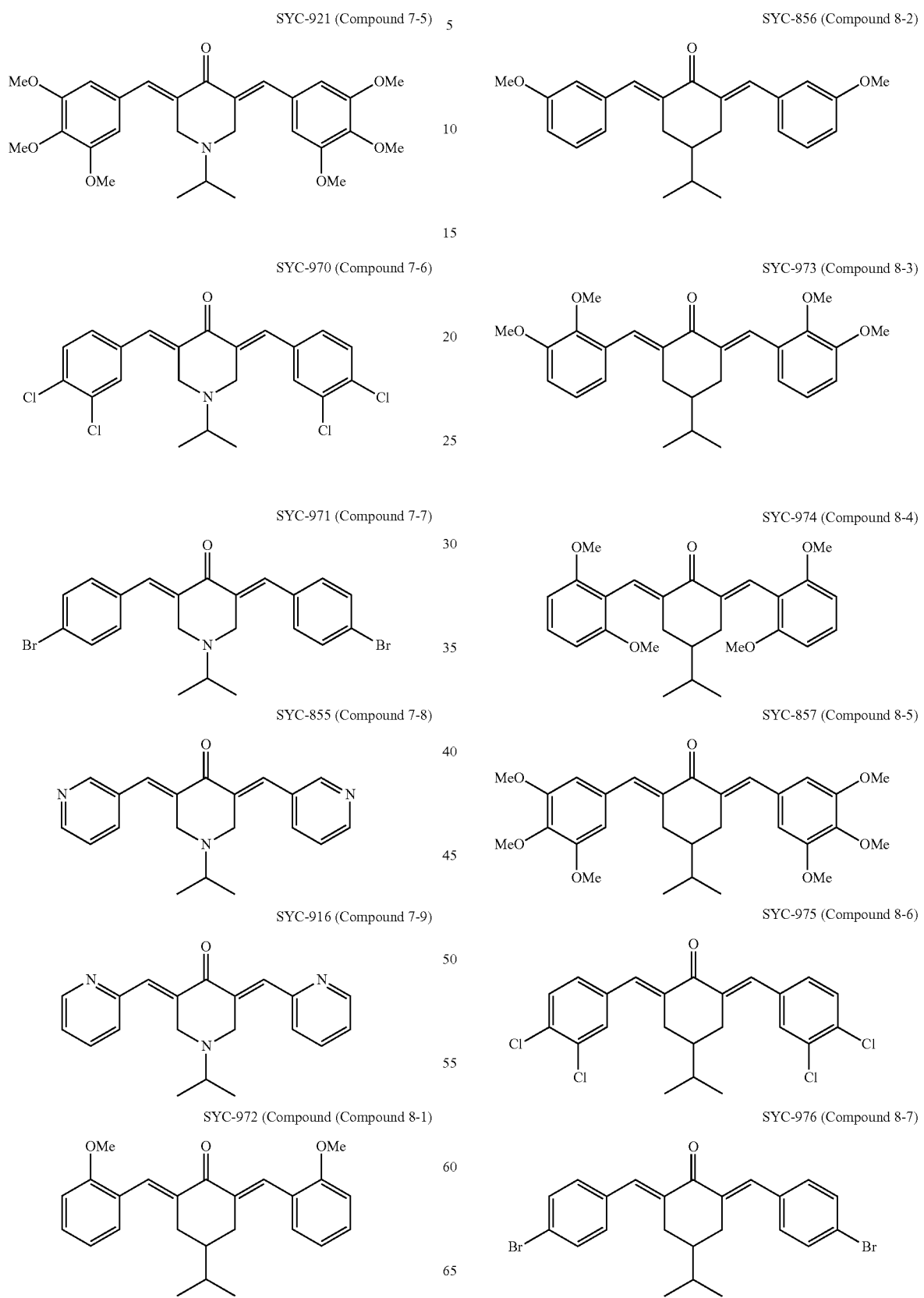

SYC-977 (Compound 8-8)
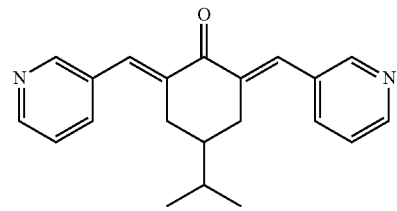
SYC-919 (Compound 8-9)
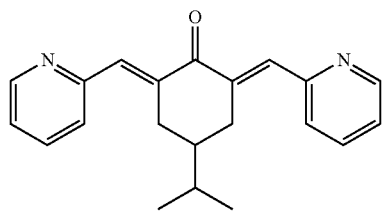
Compound S2
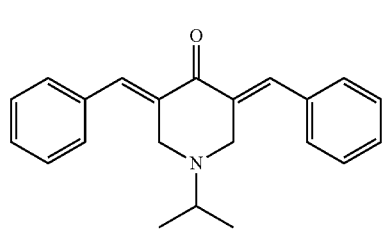
Compound S3
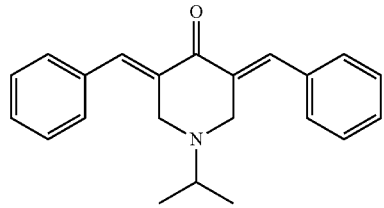
Compound S15
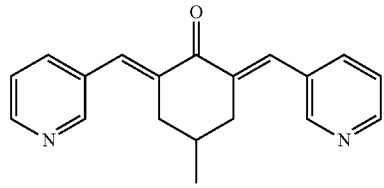
Compound S18
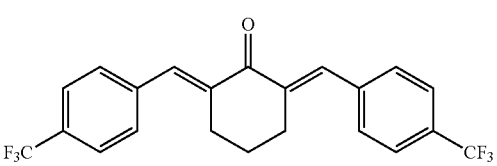
SYC-923 (Compound 1-8-2)
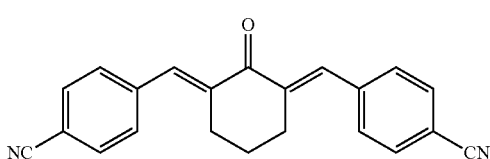
SYC-925 (Compound 4-8-2)
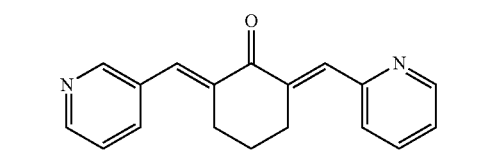
SYC-927 (Compound 7-8-2)
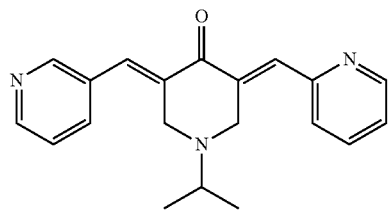
SYC-917 (Compound 7-18)
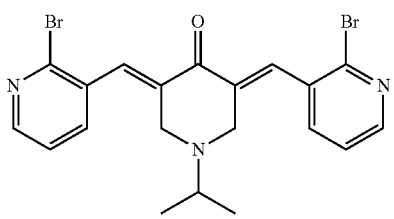
SYC-918 (Compound 7-19)
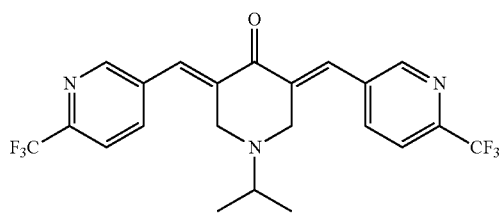
Compound 9-2
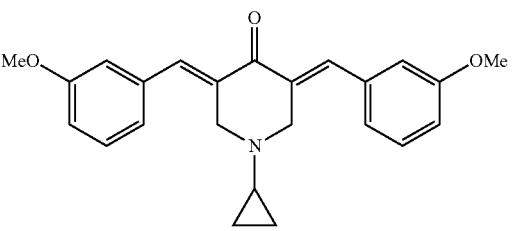
Compound 9-8
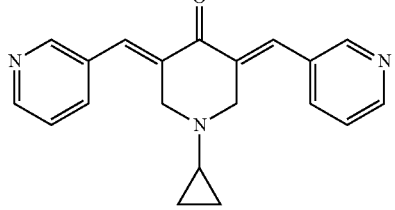
Compound 10-1
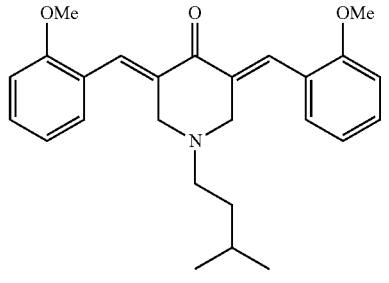

-continued

Compound 10-2

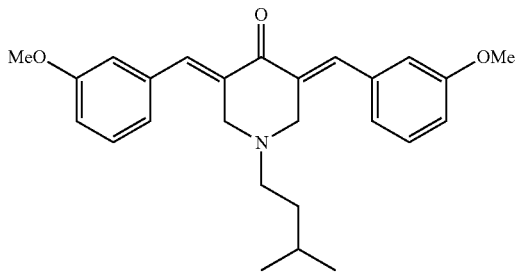

In some embodiments, the compound is SYC-944 (Compound 2-8) (also referred to herein as MCB-613). In some embodiments, the compound is not SYC-944 (Compound 2-8) (also referred to herein as MCB-613). In some embodiments, the compound is Compound 9-2, Compound 9-8, Compound 10-1, or Compound 10-2.

II. Methods of Making the Compounds

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H-NMR or $^{13}$C-NMR), infrared spectroscopy, spectrophotometry (e.g., UV-visible), or mass spectrometry, or by chromatography such as high performance liquid chromatography (HPLC) or thin layer chromatography.

Exemplary methods for synthesizing compounds as described herein are provided in Example 1 below and in International Patent Application Publication No. WO 2016/109470, which is incorporated herein by reference.

III. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., J. Pharm. Sci. (1977) 66, 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.01 to about 50 mg/kg of body weight of active compound per day, about 0.05 to about 25 mg/kg of body weight of active compound per day, about 0.1 to about 25 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, about 5 mg/kg of body weight of active compound per day, about 2.5 mg/kg of body weight of active compound per day, about 1.0 mg/kg of body weight of active compound per day, or about 0.5 mg/kg of body weight of active compound per day, or any range derivable therein. Optionally, the dosage amounts are from about 0.01 mg/kg to about 10 mg/kg of body weight of active compound per day. Optionally, the dosage amount is from about 0.01 mg/kg to about 5 mg/kg. Optionally, the dosage amount is from about 0.01 mg/kg to about 2.5 mg/kg.

Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. Further, depending on the route of administration, one of skill in the art would know how to determine doses that result in a plasma concentration for a desired level of response in the cells, tissues and/or organs of a subject.

IV. Methods of Use

Provided herein are methods to treat a myocardial infarction or other ischemic injury (e.g., a stroke) in a subject. The methods include administering to a subject an effective amount of one or more of the compounds or compositions described herein, or a pharmaceutically acceptable salt or prodrug thereof. Effective amount, when used to describe an amount of compound in a method, refers to the amount of a compound that achieves the desired pharmacological effect or other biological effect.

Also contemplated is a method that includes administering to the subject an amount of one or more compounds described herein such that an in vivo concentration at a target cell in the subject corresponding to the concentration administered in vitro is achieved.

Further described herein are methods for reducing a myocardial infarct size in a subject who has suffered a myocardial infarction. The methods include administering to the subject an effective amount of one or more compounds or a composition as described herein. The myocardial infarct size can be reduced by at least 5% as compared to a myocardial infarct size in an untreated subject who has suffered a myocardial infarction (e.g., a subject who has suffered a myocardial infarction and has not been administered any treatment for the myocardial infarction or a subject who has suffered a myocardial infarction and has been administered a therapeutic agent other than a compound or composition as described herein). Optionally, the myocardial infarct size can be reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% as compared to a myocardial infarct size in an untreated subject who has suffered a myocardial infarction. The compounds and compositions described herein are also useful in preventing or reducing cardiomyocyte loss in a subject who has suffered a myocardial infarction. The methods for preventing or reducing cardiomyocyte loss in a subject who has suffered a myocardial infarction include administering to the subject an effective amount of one or more compounds or a composition as described herein.

Further described herein are methods for improving cardiovascular function, improving cardiac vascular perfusion, improving central nervous system vascular function, improving central nervous system vascular perfusion, promoting wound healing, and/or preventing or treating hypertrophic cardiomyopathy in a subject. The methods include administering to the subject an effective amount of one or more compounds or a composition as described herein. Optionally, the subject has suffered an ischemic injury, such as a myocardial infarction or stroke. Optionally, the subject is an elderly individual, an obese individual, a diabetic individual, an individual suffering from a metabolic syndrome, an individual exposed to smoke (e.g., smokers and individuals exposed to second-hand smoke for an extended period), an individual suffering from elevated blood pressure, blood cholesterol, or triglyceride levels, or an individual suffering from an autoimmune condition.

The methods for treating a myocardial infarction, reducing a myocardial infarct size, preventing or reducing cardiomyocyte loss, improving cardiovascular function, improving cardiac vascular perfusion, improving central nervous system vascular function, improving central nervous system vascular perfusion, promoting wound healing, and/or preventing or treating hypertrophic cardiomyopathy in a subject can further comprise administering to the subject one or more additional agents. The one or more additional agents and the compounds described herein or pharmaceutically acceptable salts or prodrugs thereof can be administered in any order, including concomitant, simultaneous, or sequential administration. Sequential administration can be administration in a temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Additional therapeutic agents include, but are not limited to, antiplatelet agents, statins, beta blockers, and renin-angiotensin-aldosterone system (RAAS) blockers (e.g., angiotensin-converting enzyme (ACE) inhibitors and angiotensin receptor blockers (ARBs)). Illustrative, non-limiting examples of antiplatelet agents useful as an additional therapeutic agent as described herein include glycoprotein (GP) IIb/IIIa receptor antagonists (e.g., abciximab, eptifibatide, and tirofiban), dipyridamole, cylooxygenase inhibitors (e.g., acetylsalicylic acid, ibuprofen indomethacin, and sulfinpyrazone), adenosine diphosphate (ADP) receptor antagonists (e.g., clopidogrel and ticlopidine), and phosphodiesterase inhibitors (e.g., cilostazol).

Illustrative, non-limiting examples of statins useful as an additional therapeutic agent as described herein include atorvastatin, cerivastatin, pravastatin, lovastatin, mevastatin, simvastatin, rosuvastatin, fluvastatin, and pitavastatin.

Illustrative examples of beta blockers useful as an additional therapeutic agent as described herein include, but are not limited to, acebutolol, atenolol, betaxolol, bisoprolol fumarate, carteolol, carvedilol, esmolol, labetalol, metoprolol, nadolol, nebivolol, penbutolol, pindolol, propranolol, sotalol, and timolol.

Illustrative examples of renin-angiotensin-aldosterone system (RAAS) blockers (e.g., angiotensin-converting enzyme (ACE) inhibitors and angiotensin receptor blockers (ARBs)) useful as an additional therapeutic agent as described herein include, but are not limited to, aliskiren, enalkiren, remikirem, benazepril, benazeprilat, captopril, enalapril, lisinopril, perindopril, quinapril, ramipril, trandolapril, fosinopril, moexipril, perindopril, losartan, valsartan, irbesartan, candesartan, telmisartan, tasosartan, eprosartan, spironolactone, and eplerenone.

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

Optionally, a compound or therapeutic agent as described herein may be administered in combination with a surgery (e.g., a coronary artery bypass surgery), an angioplasty, a stenting, or another implantation procedure.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of a myocardial infarction), during early onset (e.g., upon initial signs and symptoms of a myocardial infarction), or after the occurrence of a myocardial infarction. Prophylactic administration can occur for several days to years prior to the manifestation of symptoms of a myocardial infarction. Therapeutic treatment involves administering to a subject a therapeutically effective amount of the compounds and compositions or pharmaceutically acceptable salts thereof as described herein after the occurrence of a myocardial infarction.

The methods herein for prophylactic and therapeutic treatment optionally comprise selecting a subject who has suffered or is at an elevated risk of suffering an ischemic injury such as a myocardial infarction or stroke (e.g., an obese individual, an elderly individual, or an individual who has previously suffered an ischemic injury such as a myocardial infarction or stroke). A skilled artisan can make such a determination using, for example, a variety of prognostic and diagnostic methods, including, for example, a personal or family history of the disease or condition, clinical tests (e.g., genetic tests), and the like. Optionally, the methods herein can be used for preventing a subject who has suffered a myocardial infarction from suffering a subsequent myocardial infarction.

The compounds and compositions described herein or pharmaceutically acceptable salts thereof are useful for treating a myocardial infarction, reducing a myocardial infarct size, preventing or reducing cardiomyocyte loss, improving cardiovascular function, promoting wound healing, and/or preventing or treating hypertrophic cardiomyopathy in humans, including, without limitation, pediatric and geriatric populations, and in animals, e.g., veterinary applications.

V. Kits

Also provided herein are kits for treating a myocardial infarction, reducing a myocardial infarct size, preventing or reducing cardiomyocyte loss, improving cardiovascular function, promoting wound healing, and/or preventing or treating hypertrophic cardiomyopathy in a subject. A kit can include any of the compounds or compositions described herein. For example, a kit can include one or more compounds of Formula I. A kit can further include one or more additional agents, such as antiplatelet agents, statins, beta blockers, renin-angiotensin-aldosterone system (RAAS) blockers (e.g., angiotensin-converting enzyme (ACE) inhibitors and angiotensin receptor blockers (ARBs)), and combinations of these.

A kit can include an oral formulation of any of the compounds or compositions described herein. A kit can include an intravenous or intraperitoneal formulation of any of the compounds or compositions described herein. A kit can additionally include directions for use of the kit (e.g., instructions for treating a subject), a container, a means for administering the compounds or compositions (e.g., a syringe), and/or a carrier.

As used herein the terms treatment, treat, or treating refer to a method of reducing one or more symptoms of a disease or condition. Thus in the disclosed method, treatment can refer to a 5%, 10%, 20%, 30%, 40%, 50%, 60%, 70%, 80%, 90%, or 100% reduction in the severity of one or more symptoms of the disease or condition. For example, a method for treating a disease is considered to be a treatment if there is a 5% reduction in one or more symptoms or signs (e.g., a size of a myocardial infarct) of the disease in a subject as compared to a control. As used herein, control refers to the untreated condition (e.g., a myocardial infarct size in an untreated subject who has suffered a myocardial infarction). Thus the reduction can be a 5%, 10%, 20%, 30%, 40%, 50%, 60%, 70%, 80%, 90%, 100%, or any percent reduction in between 5% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 5%, 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

Example 1: Synthesis of Compounds

All chemicals for synthesis were purchased from Alfa Aesar (Ward Hill, Mass.) or Aldrich (Milwaukee, Wis.). The compound identity was characterized by $^1$H NMR on a Varian (Palo Alto, Calif.) 400-MR spectrometer. The purities of synthesized compounds were determined by a Shimadzu Prominence HPLC with a Zorbax C18 (or C8) column (4.6×250 mm) monitored by UV at 254 nm. The purities of the reported compounds were found to be >95%.

Synthesis of 1-cyclopropylpiperidin-4-one

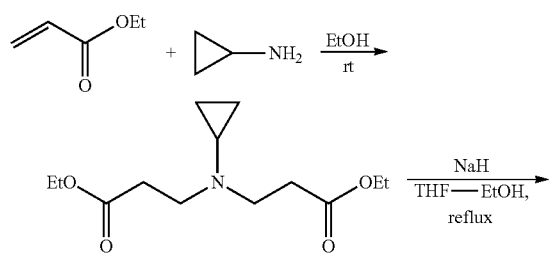

Cyclopropylamine (6.9 mL, 100 mmol) and ethyl acrylate (22.3 mL, 210 mmol, 2.1 equiv) were dissolved in absolute ethanol (50 mL). The mixture was stirred at room temperature (rt) for 4 days. The volatiles were removed in vacuo to afford a crude oil, which was purified by column chromatography (silica gel, n-hexanes:ethyl acetate from 10:1 to 1:1) to give diethyl 3,3'-(cyclopropylazanediyl)dipropanoate as a colorless liquid (15.68 g, 61%).

Sodium hydride (60% dispersion in oil, 3.0 g, 75 mmol, 1.5 equiv) and tetrahydrofuran (THF, 30 mL) were placed in an oven-dried flask, to which a solution of diethyl 3,3'-(cyclopropylazanediyl)dipropanoate (12.8 g, 50 mmol) in THF (20 mL) was added dropwise. Then absolute ethanol (2.9 mL, 50 mmol, 1.0 equiv) was added and the resulting mixture was stirred at reflux for 24 hours. The reaction was quenched with saturated ammonium chloride (50 mL). The mixture was extracted with diethyl ether (3×100 mL) and the combined organic layers were washed with water and brine, dried over Na$_2$SO$_4$. The volatiles were removed in vacuo to afford a crude oil, which was purified by column chromatography (silica gel, n-hexanes:ethyl acetate from 10:1 to 2:1) to give 1-cyclopropylpiperidin-4-one as a colorless liquid (4.52 g, 65% yield). $^1$H NMR (400 MHz, CDCl$_3$): δ 2.92 (t, J=6.2 Hz, 4H), 2.42 (t, J=6.2 Hz, 4H), 1.80-1.70 (m, 1H), and 0.55-0.47 (m, 4H).

Synthesis of 1-isopentylpiperidin-4-one

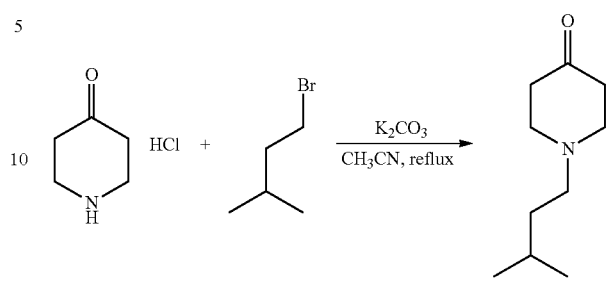

Piperidin-4-one hydrochloride (13.56 g, 100 mmol), 1-bromo-3-methylbutane (14.4 mL, 120 mmol, 1.2 equiv) and potassium carbonate (27.6 g, 200 mmol, 2.0 equiv) were dissolved in an acetonitrile/water (50/50 mL) mix solvent. The mixture was stirred at reflux for 12 hours. The mixture was cooled to rt and extracted with diethyl ether (3×100 mL) and the combined organic layers were washed with water and brine, and dried over Na$_2$SO$_4$. The volatiles were removed in vacuo to afford a crude oil, which was purified by column chromatography (silica gel, n-hexanes:ethyl acetate from 10:1 to 2:1) to give 1-isopentylpiperidin-4-one as a colorless liquid (10.32 g, 61% yield). $^1$H NMR (400 MHz, CDCl$_3$): δ 2.71 (t, J=5.9 Hz, 4H), 2.43 (t, J=5.9 Hz, 6H), 1.61 (septet, J=6.6 Hz, 1H), 1.40 (td, J=7.6, 6.6 Hz, 2H), and 0.90 (d, J=6.6 Hz, 6H).

General Method for Synthesis of α,β-Unsaturated Ketone

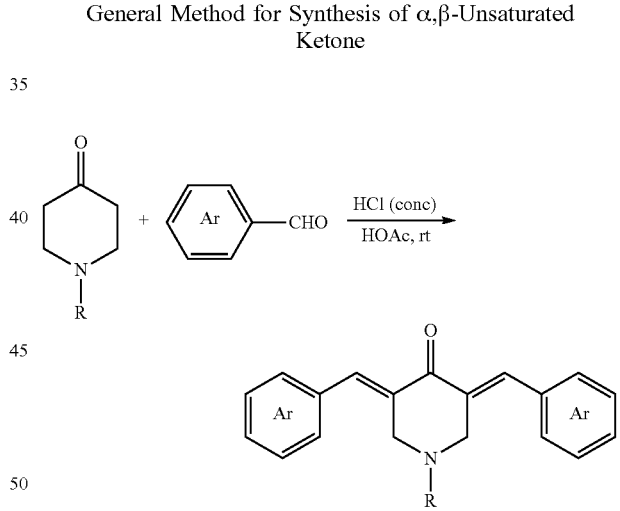

N-protected piperidin-4-one (5 mmol) and aldehyde (11 mmol, 2.2 equiv) were dissolved in acetic acid (10 mL) to which concentrated hydrochloric acid (3 mL) was added. The mixture was stirred at rt for 12 hours. The reaction was carefully quenched by saturated sodium bicarbonate. The mixture was extracted with ethyl acetate (3×30 mL) and the combined organic layers were washed with water and brine, and dried over Na$_2$SO$_4$. The volatiles were removed in vacuo to afford a crude oil, which was purified by column chromatography (silica gel, n-hexanes:ethyl acetate from 5:1 to 1:1) to give α,β-unsaturated ketone (60-76% yield). The compounds described herein were prepared according to the general method, including Compounds 9-2, 9-8, 10-1, and 10-2. The characterizations for each of these compounds is provided below.

(3E,5E)-1-Cyclopropyl-3,5-bis(3-methoxybenzylidene)piperidin-4-one (9-2)

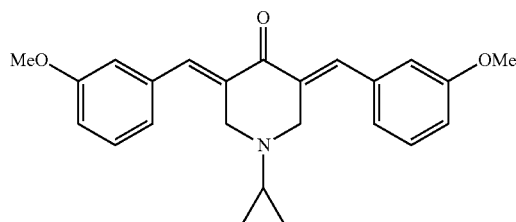

Yellow powder. $^1$H NMR (400 MHz, CDCl$_3$): δ 7.75 (s, 2H), 7.36 (t, J=8.0 Hz, 2H), 7.03 (d, J=8.0 Hz, 2H), 6.96 (s, 2H), 6.93 (d, J=8.0 Hz, 2H), 3.99 (s, 4H), 3.85 (s, 6H), 1.96-1.91 (m, 1H), 0.51-0.47 (m, 2H), and 0.41-0.38 (m, 2H); $^{13}$C NMR (100 MHz, CDCl$_3$): 187.6, 159.7, 136.7, 136.4, 133.8, 129.7, 123.0, 116.1, 114.7, 54.0, 51.3, 38.1, and 6.9; MS (ESI) [M+H]$^+$ 376.5.

(3E,5E)-1-cyclopropyl-3,5-bis(pyridin-3-ylmethylene)piperidin-4-one (9-8)

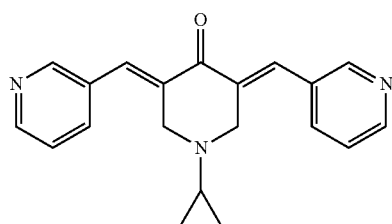

Orange powder. $^1$H NMR (400 MHz, CDCl$_3$): δ 8.67 (s, 2H), 8.59 (d, J=4.8 Hz, 2H), 7.73 (s, 2H), 7.70 (d, J=8.0 Hz, 2H), 7.37 (dd, J=8.0, 4.8 Hz, 2H), 3.99 (s, 4H), 1.99-1.94 (m, 1H), 0.58-0.51 (m, 2H), and 0.47-0.42 (m, 2H); $^{13}$C NMR (100 MHz, CDCl$_3$): 187.2, 151.2, 149.9, 137.3, 135.8, 132.4, 131.1, 123.6, 55.8, 40.1, and 6.9; MS (ESI) [M+H]$^+$ 318.5.

(3E,5E)-1-isopentyl-3,5-bis(2-methoxybenzylidene)piperidin-4-one (10-1)

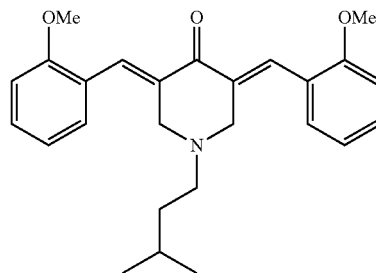

Compound 10-1 was prepared as a hydrochloric acid salt (yellow powder). $^1$H NMR (400 MHz, CDCl$_3$): δ 13.19 (br, 1H), 8.36 (s, 2H), 7.45 (t, J=7.3 Hz, 2H), 7.10 (d, J=6.6 Hz, 2H), 7.03 (t, J=7.3 Hz, 2H), 6.97 (d, J=8.3 Hz, 2H), 4.49 (d, J=15.6 Hz, 2H), 4.28 (d, J=15.6 Hz, 2H), 3.88 (s, 6H), 2.87-2.82 (m, 2H), 1.43 (septet, J=6.6 Hz, 1H), 1.30 (td, J=7.6, 6.6 Hz, 2H), and 0.70 (d, J=6.6 Hz, 6H); $^{13}$C NMR (100 MHz, CDCl$_3$): 182.2, 158.2, 141.4, 132.5, 130.5, 124.1, 122.2, 120.9, 111.3, 55.7, 50.8, 49.6, 32.8, 26.0, and 22.1; MS (ESI) [M+H]$^+$ 406.5.

(3E,5E)-1-isopentyl-3,5-bis(3-methoxybenzylidene)piperidin-4-one (10-2)

Compound 10-2 was prepared as a hydrochloric acid salt (yellow powder). $^1$H NMR (400 MHz, CDCl$_3$): δ 13.46 (br, 1H), 8.17 (s, 2H), 7.40 (t, J=8.0 Hz, 2H), 7.01 (dd, J=8.0, 2.3 Hz, 2H), 6.89 (d, J=8.0 Hz, 2H), 6.86 (d, J=2.3 Hz, 2H), 4.59 (d, J=15.6 Hz, 2H), 4.48 (d, J=15.6 Hz, 2H), 3.84 (s, 6H), 2.89-2.84 (m, 2H), 1.46 (septet, J=6.6 Hz, 1H), 1.37 (td, J=7.6, 6.6 Hz, 2H), and 0.72 (d, J=6.6 Hz, 6H); $^{13}$C NMR (100 MHz, CDCl$_3$): 181.8, 160.0, 144.8, 134.3, 130.4, 123.9, 122.2, 116.3, 116.1, 55.5, 50.5, 50.2, 32.7, 26.0, and 22.1; MS (ESI) [M+H]$^+$ 406.5.

Example 2: Cardiac Protection Promotion and Repair after Myocardial Infarction

The data herein show that administration of the compounds described herein following myocardial infarction promotes cardiac protection and repair. Among other functions, representative compounds prevented the increase of infarct size, cardiac hypertrophy, and collagen deposition. The compounds significantly improved cardiac post-infarction function. The compounds also increased angiogenesis, promoted cardiac β-oxidation, and significantly decreased the levels of methylglutaryl carnitine, a metabolite associated with dilated cardiomyopathy.

Methods

All animal studies and protocols were approved by the Institutional Animal Care and Use Committee at Baylor College of Medicine and conducted in strict accordance with the *National Institutes of Health Guide for the Care and Use of Laboratory Animals*. Adult (8-10 week old) ICR (CD1) mice were used for all studies.

Model of heart failure in adult mice. To induce myocardial infarction (MI) in 8- to 10-week-old mice, the left anterior descending (LAD) artery was permanently ligated. Briefly, mice were anesthetized with 2% isoflurane and then intubated. The heart was exposed by performing a thoracotomy through the fourth or fifth intercostal space and an 8-0 nylon suture was tied around the LAD artery. 10 uls of Adenoviral SRC-3 (Ad-SRC-3) or adenoviral GFP (Ad-GFP) at a titre of 9×10$^9$ pfu/ml was injected into the anterior free wall near left ventricular descending coronary artery. To assess cell cycle entry, the analog 5-ethynyl-2'-deoxyuridine (EdU; 0.2 g/L, Santa Cruz, SC-284628A) was added to the drinking water for the 9 day duration of the experiment. Cell proliferation was measured using Click-iT EdU kit (Invitrogen, C10339). The initial dose of MCB-613 was administered intraperitoneally at 20 mg/kg 2 hours after surgery. Subsequent injections of the same dose were given for 6 additional days, and then repeated doses were given for 3 days at week 9 and week 16. Mice were harvested at indicated time points for analyses.

Echocardiography. Cardiac function was determined by echocardiography (VisualSonics, Vevo 2100, 40 Mhz-550S probe). After alignment in the transverse B-mode with the papillary muscles, cardiac function was measured on M-mode images.

Histological analysis. Whole hearts were fixed with 10% formalin, embedded in paraffin, and sectioned at 7-µm intervals. Each slide had 3 or 10 sections, which started at the apex and ended at the suture ligation site (approximately 30-50 slides). Sections at the papillary level (slides 20-30) were stained with Picrosirius red to identify areas of fibrosis. Infarct size was determined using a length-based approach.

Immunostaining analysis. Immunohistochemistry and immunofluorescent staining experiments were performed on FFPE (formalin-fixed and paraffin-embedded sections). TUNEL staining to detect apoptotic cells was done using the DeadEnd™ Fluorometric TUNEL System manufacturer's protocol (Promega, GS3250).

Isolation of cardiac cells for single cell transcription profiling. Mice were placed under the surgical plane of anesthesia before cervical dislocation. The hearts were removed and cells were isolated by Langendorff retrograde perfusion of calcium-free pH 7.4 Tyrodes solution (130 mM NaCl, 74.55 mM KCl, 0.5 mM MgCl, 0.33 mM $NaH_2PO_4$, 0.25 mm HEPES, 22 mM glucose) with collagenase, 1 mg/mL for 15 minutes. The hearts were then removed from the apparatus, and finely minced in the same Tyrodes buffer with 15 mg/mL bovine serum albumin (BSA) before trituration with a glass pipette. Cardiomyocytes were then pelleted by differential centrifugation, 300 RPM for 3 minutes. The supernatant containing the noncardiomyocyte population of cells was then filtered through a 70 micron filter and pelleted at 750 G, and resuspended in 1.1 mL 2% fetal bovine serum (FBS) in phosphate buffered saline (PBS). 0.1 mL was removed for the "no stain control" for fluorescence-activated cell sorting (FACS). The other 1 mL was incubated with 4 ug/mL Calcein Blue and 10 microM DyeCycle Ruby and incubated at 37° C. for 10 minutes. The cells were then spun down at 600G, and resuspended in 0.5 mL 2% FBS/PBS containing Sytox Green (30 nM). Cells were then sorted for: Sytox Green−, Calcein+, DyeCycle Ruby+ into 0.4% FBS in PBS using a FACS Aria ii cell sorter. The cells were then pelleted and resuspended in 100 uL 0.4% FBS in PBS, counted, and then flowed through the 10× Genomics Chromium system for single cell transcriptomic profiling.

Metabolomic profiling. Hearts from 4 control and 4 MCB-613-treated mice were isolated 24 hours post-MI, perfused with 10 mM KCl, snap frozen in liquid nitrogen and stored at −80° C. 10 mgs of tissue was analyzed for fatty acids and carnitines normalized to 3 normal liver control samples. Fatty acids were normalized by Internal Standard L-Tryptophan and carnitines normalized by Internal Standard L-Zeatine.

RER, $VO_2$ and $VCO_2$ measurements. Respiratory exchange ratio (RER), oxygen consumption ($VO_2$) and carbon dioxide expiration ($VCO_2$) were measured by indirect calorimetry using a progressive maximal exercise test until mice reached exhaustion.

Results

SRC-3 activation has low toxicity. Nuclear receptor coactivator 3 (NCOA3) is expressed at low levels in human adult hearts, indicating that the activation of SRC-3 will have few side effects. In addition, MCB-613 has a low toxicity profile in vitro and in vivo. NCOA3 expression in normal human hearts was determined and compared to muscle tissues analyzed from the GTEx database from approximately 1,000 autopsied donors. FIG. 1 contains graphs showing the expression of NCOA3 in normal human hearts (left panel) and in muscle tissues (right panel). Fragments per kb gene length per million mapped reads (FPKM) are shown on the y-axis and the data points represent the samples. The data are sorted by level of expression of NCOA3.

Figure 2:
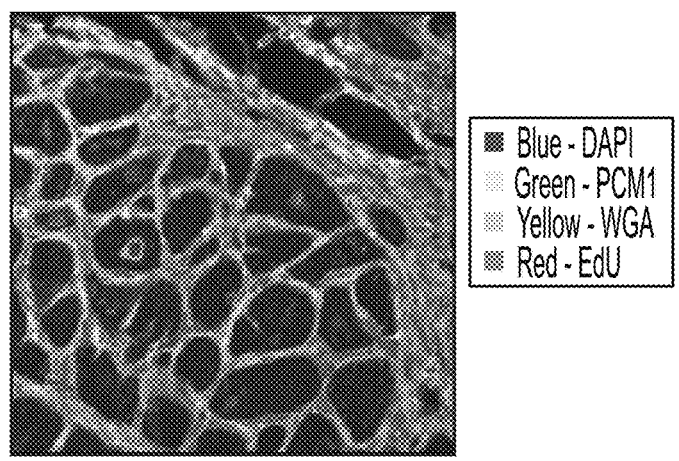
FIG. 2 is an image of a heart from a mouse injected with adeno-SRC3 before harvesting.

SRC-3 expression induces the proliferation of non-cardiomyocytes in hearts. Adenovirus derived SRC-3 (Adeno-SRC3) was injected into the left ventricular free wall of a wild type adult mouse heart. Mice were fed 5-ethynyl-2'-deoxyuridine-treated water (EdU water) as a cell proliferation marker. Hearts were harvested after nine days and stained with 4',6-diamidino-2-phenylindole (Dapi) to identify nuclei, the PCM1 cardiomyocyte marker, the cell surface marker wheat germ agglutinin (WGA), and the cell proliferation marker EdU. FIG. 2 is an image of the heart and shows that SRC-3 expression induces proliferation of non-cardiomyocytes in wild type adult mouse hearts.

Figure 3A:
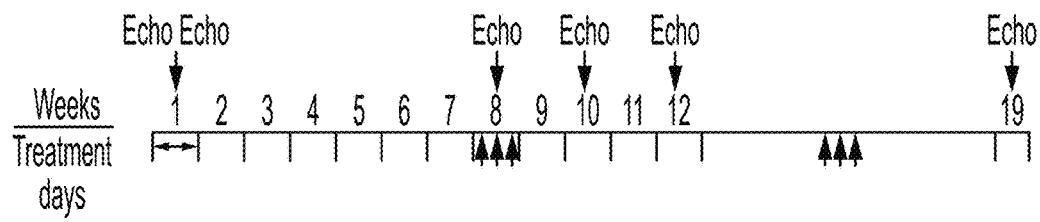
FIG. 3A depicts an experimental timeline for drug treatment and echocardiography measurements after myocardial infarction (MI).
Figure 3B:
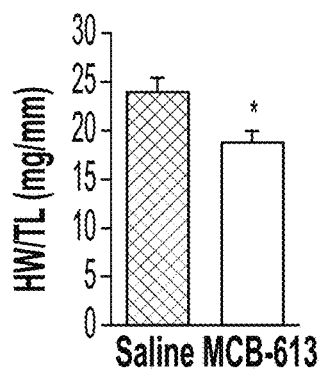
FIG. 3B is a graph showing the heart weight and tibia length ratios (HW/TL) of mice after a myocardial infarction.
Figure 3C:
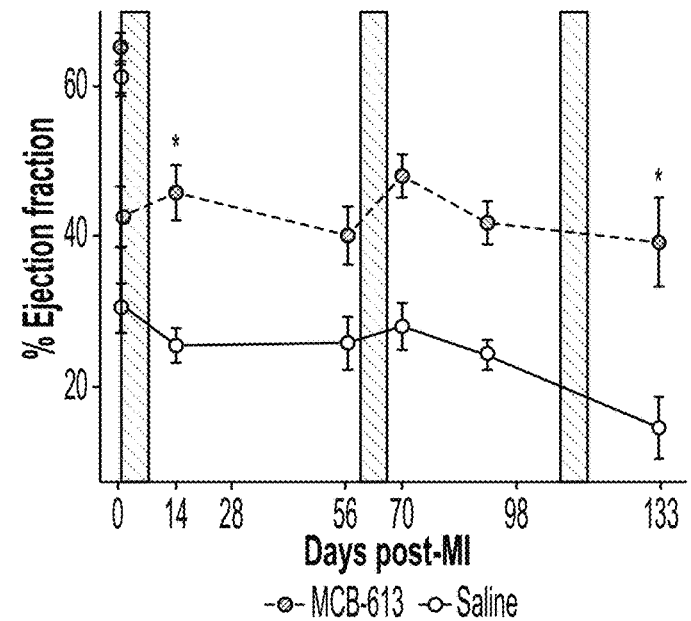
FIG. 3C is a graph showing the effects of MCB-613 treatment in mice after a myocardial infarction.
Figure 3D:
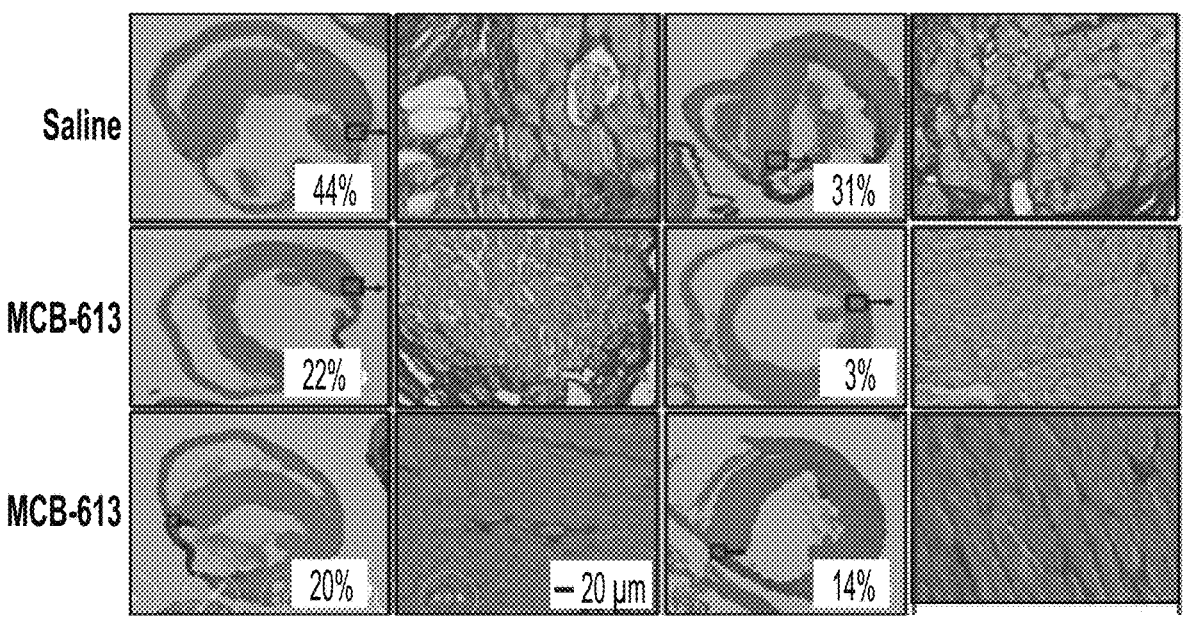
FIG. 3D contains images of mouse hearts harvested after a myocardial infarction and stained to visualize collagen fibers.
Figure 4:
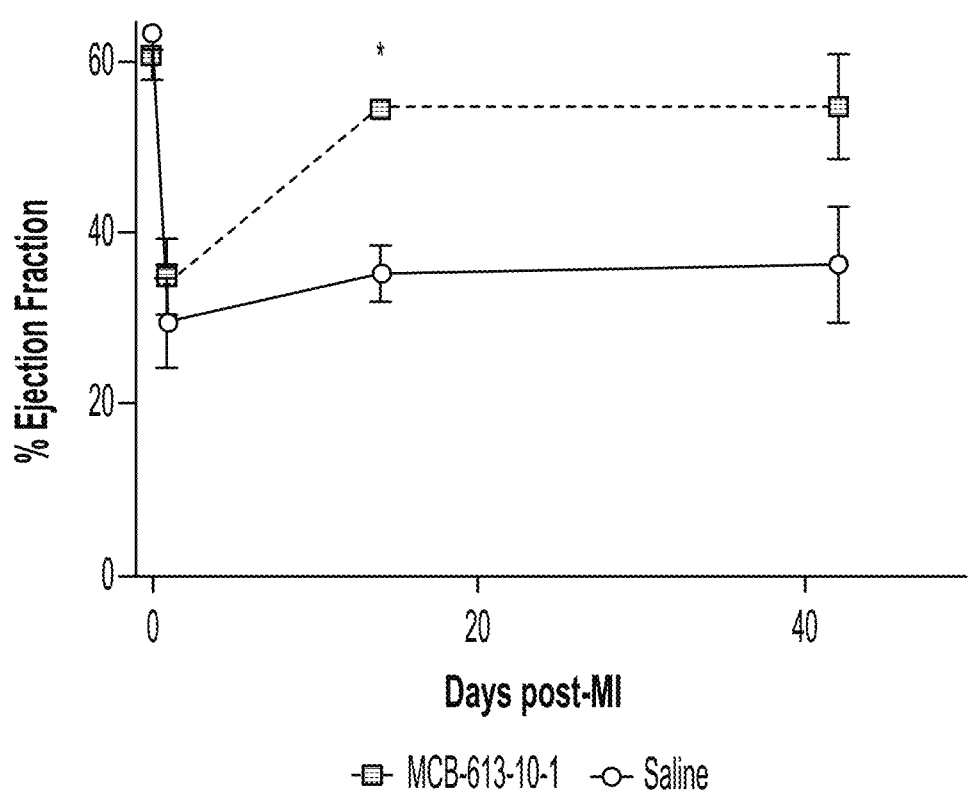
FIG. 4 is a graph showing the effects of Compound 10-1 treatment in mice after a myocardial infarction.
Figure 8:
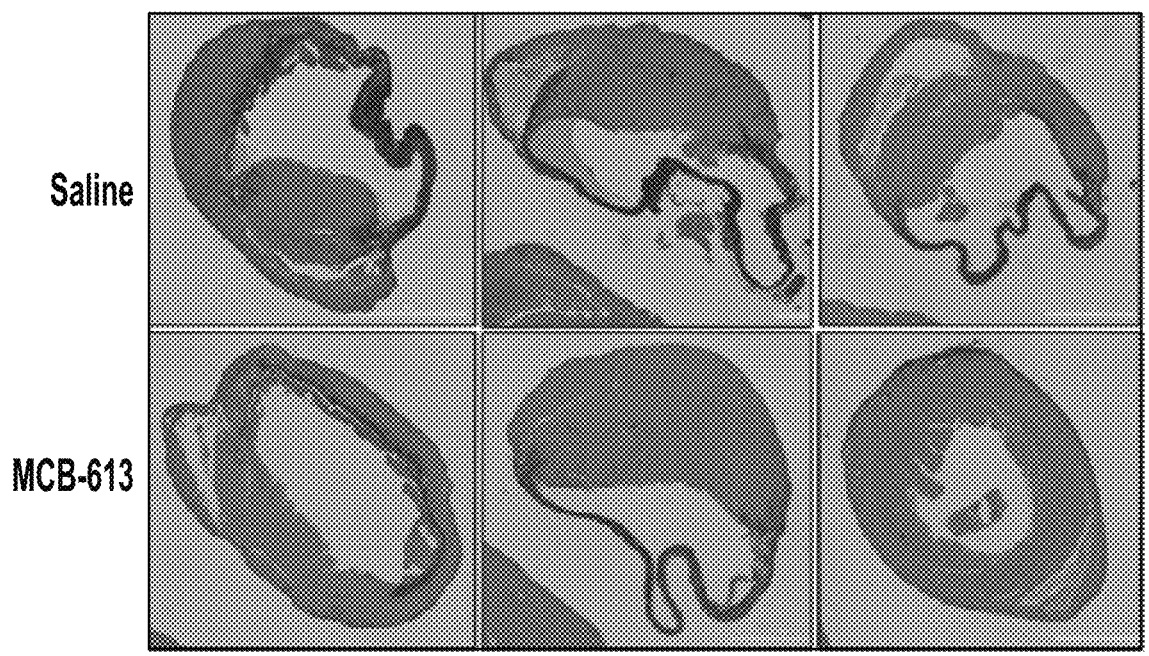
FIG. 8 contains pictures of heart cross sections at the level of the papillary muscle after myocardial infarction and after treatment with Compound 10-1.

The compounds described herein protect against early and progressive loss of cardiac function after myocardial infarction. Mice were treated with representative compounds described herein after myocardial infarction. FIG. 3A shows an experimental timeline for drug treatment and echocardiography measurements after myocardial infarction. MCB-613 or saline was administered two hours after ligation and for six additional days every 24 hours. Repeat injections were given three times per week at weeks 8 and 16. The heart weight and tibia length were measured at week 10, as shown in FIG. 3B. Six mice were administered saline and seven mice were administered MCB-613. P<0.03. Left ventricular ejection fraction was determined by echocardiography (n=14 up to 12 weeks; n=3 at 19 weeks) (FIG. 3C). Data were analyzed by ANOVA with repeated measures and presented as means+/− SEM. P<0.001. FIG. 3D contains images of mouse hearts harvested after a myocardial infarction and stained to visualize collagen fibers. Specifically, FIG. 3D shows picrosirius red stain of cross sections at the level of the papillary muscle at 4x and corresponding 20× magnification of the infarct border zone at 10 weeks post-myocardial infarction. Infarct size is presented as % length. The data demonstrate a decrease in infarct size for the MCB-613 treated mice as compared to the control mice that were administered saline. Left ventricular ejection fraction was determined by echocardiography for mice treated with Compound 10-1 after a myocardial infarction (see FIG. 4). FIG. 8 shows picrosirius red stain of cross sections at the level of the papillary muscle at six weeks post-myocardial infarction. Infarct size is presented as % length. The data demonstrate a decrease in infarct size for the Compound 10-1 treated mice as compared to the control mice that were administered saline.

Figure 5A:
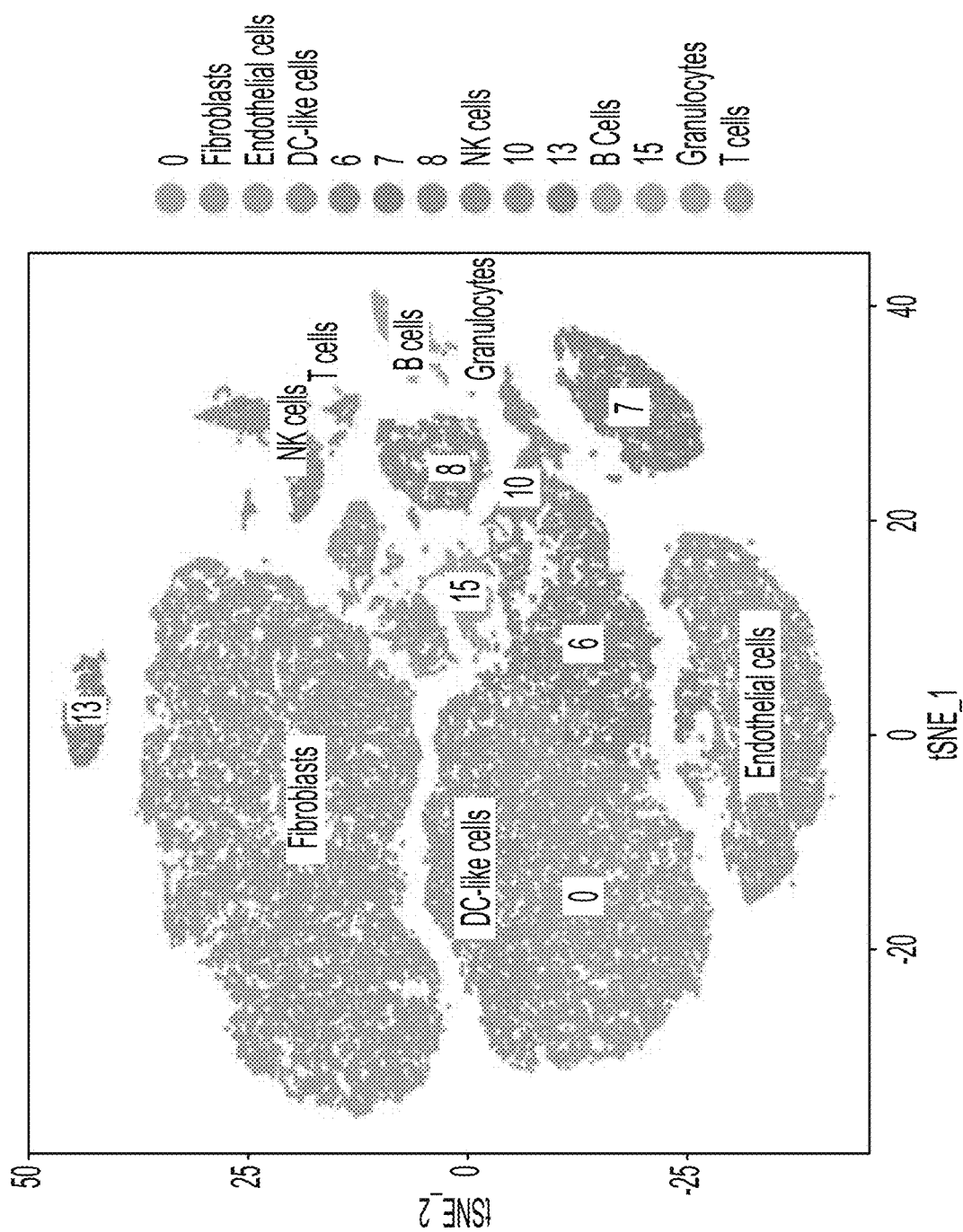
FIG. 5A is a plot depicting a comprehensive single cell transcriptional profiling of non-myocyte cells in an adult mouse heart.
Figure 5C:
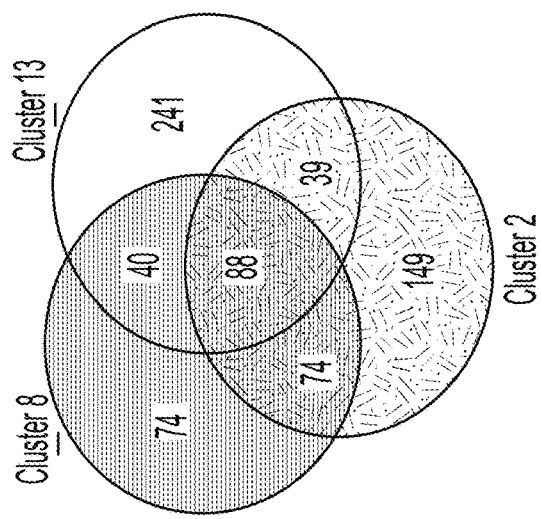
FIG. 5C is a Venn analysis of three cell clusters with endothelial signature.
Figure 5B:
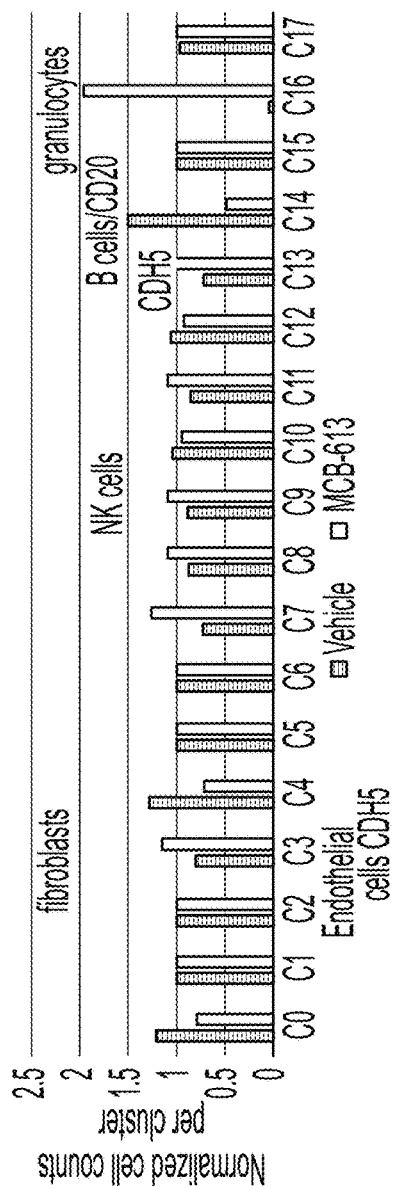
FIG. 5B is a graph showing the different cell types present in an MCB-613 treated heart after myocardial infarction.

MCB-613 induces changes in major and minor non-cardiomyocyte cell types in the heart post-myocardial infarction. Comprehensive single cell transcriptional profiling was performed of non-myocyte cells in the adult mouse heart. Single cell sequencing was performed on non-cardiomyocytes in hearts at 10 weeks post-myocardial infarction. Cell clusters were generated by tSNE analysis and identified by gene expression signatures. See FIG. 5A for a plot depicting a comprehensive single cell transcriptional profiling of non-myocyte cells in an adult mouse heart. FIG. 5B shows the different cell types present in an MCB-613 treated heart after myocardial infarction. FIG. 5C is a Venn analysis of three cell clusters with endothelial signature, indicating that MCB-613 stimulates endothelial cell growth of two distinct endothelial cell populations in hearts at 10 weeks after myocardial-infarction.

Figure 6A:
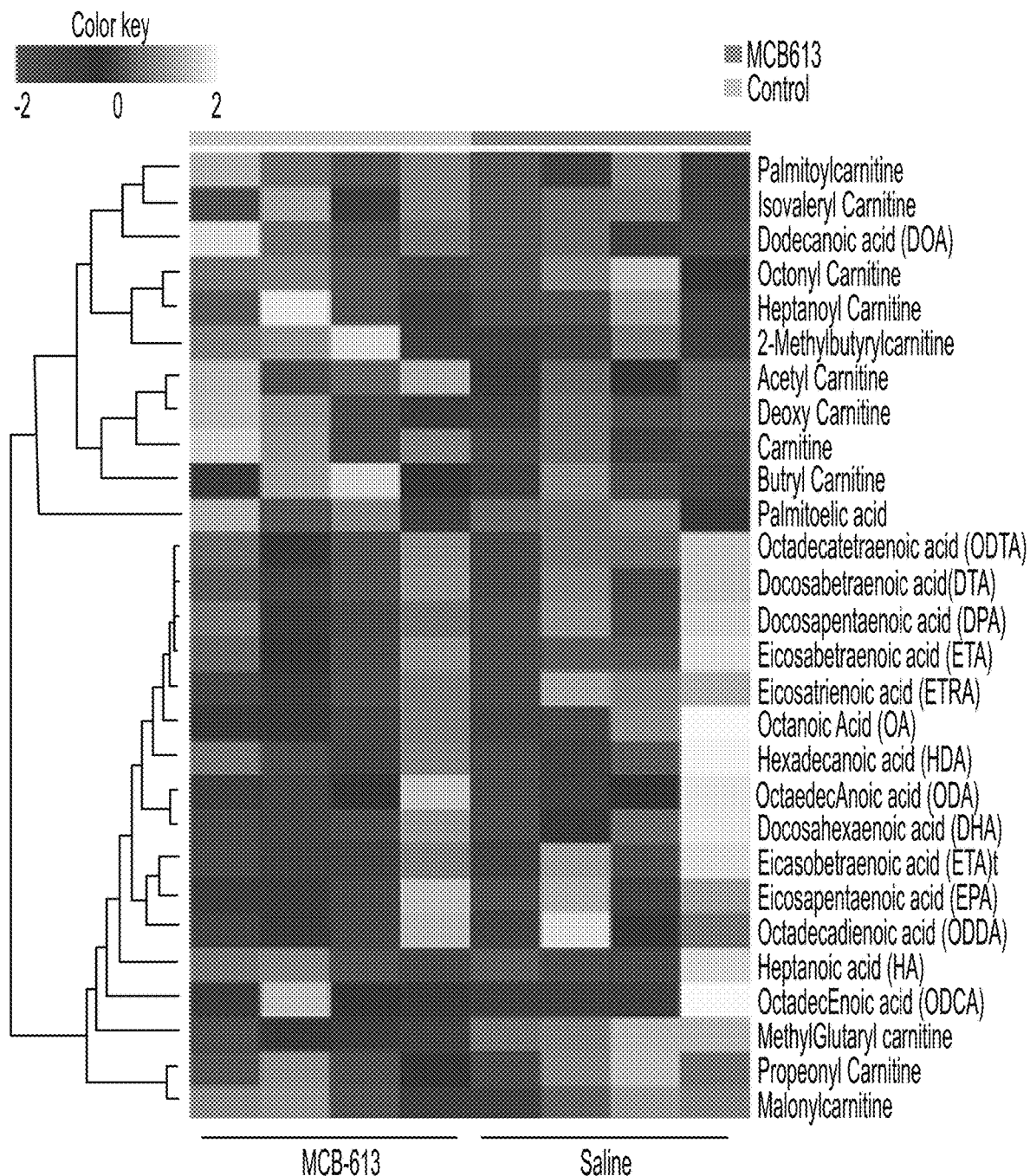
FIG. 6A is a heat map showing the metabolomics for long-chain fatty acids in mouse hearts after a myocardial infarction.
Figure 6B:
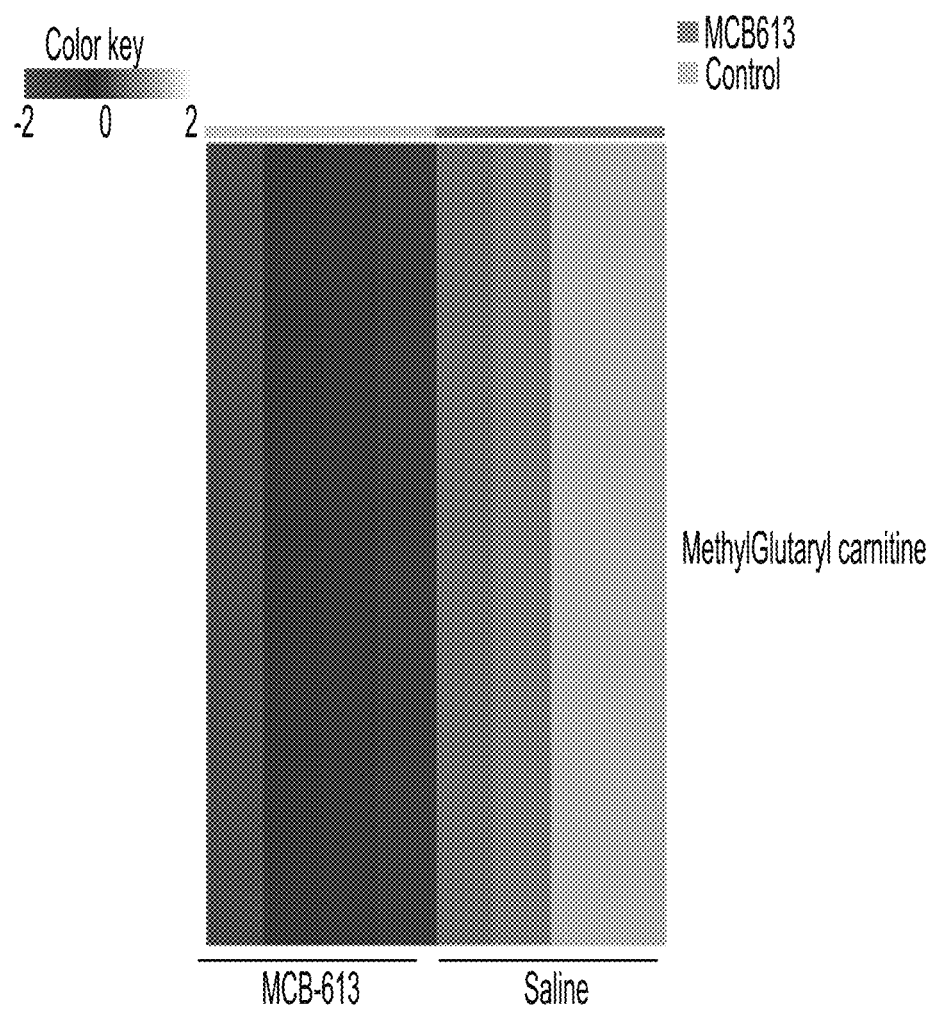
FIG. 6B is a heat map showing the metabolomics for methylglutaryl carnitine in mouse hearts after myocardial infarction.

MCB-613 increases cardioprotective carnitine metabolites. FIG. 6A is a heat map showing the metabolomics for long-chain fatty acids in mouse hearts 24 hours after a myocardial infarction. FIG. 6B is a heat map showing the metabolomics for methylglutaryl carnitine in mouse hearts after myocardial infarction (complete set FDR=1). The heat maps show that MCB-613 increases cardioprotective carnitine metabolites, increases β-oxidation of long-chain fatty acids, and decreases methylglutaryl carnitine.

Figure 7:
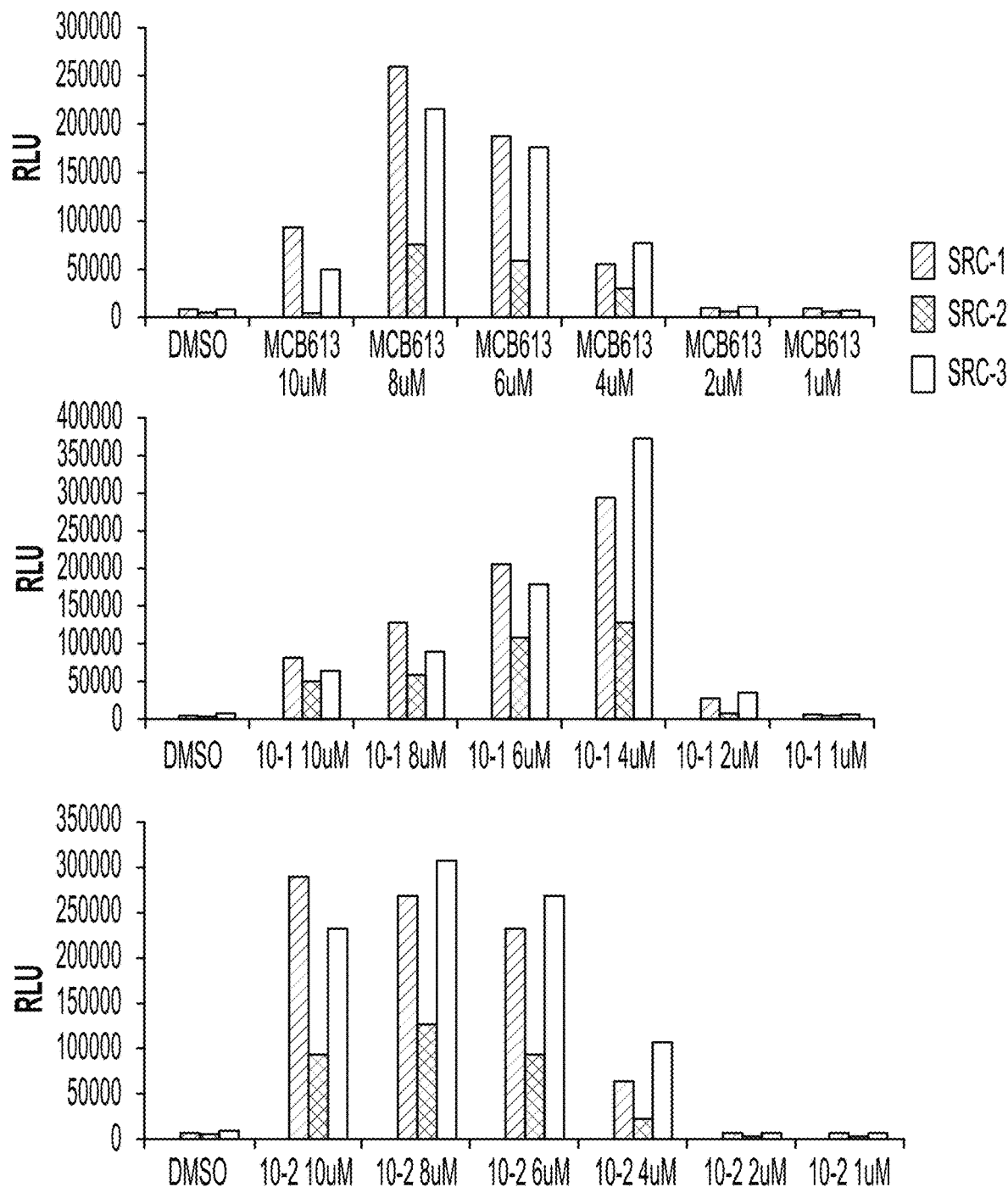
FIG. 7, upper panel shows that MCB-613 selectively stimulates the intrinsic transcriptional activity of SRCs.

The compounds described herein stimulate SRC intrinsic transcriptional activity. HeLa cells transfected with a Gal4 responsive luciferase reporter (pG5-luc) and a construct encoding SRC-1, SRC-2 or SRC-3 fused with the DNA binding domain of Gal4 (pBIND-SRC-1, pBIND-SRC-2 or pBIND-SRC-3) were exposed to treatments with compounds as described herein, including MCB-613, Compound 10-1, and Compound 10-2. FIG. 7, upper panel shows that MCB-613 selectively stimulates the intrinsic transcriptional activity of SRCs. FIG. 7, middle panel shows that Compound 10-1 selectively stimulates the intrinsic transcriptional activity of SRCs. FIG. 7, bottom panel shows that Compound 10-2 selectively stimulates the intrinsic transcriptional activity of SRCs.

Figure 9:
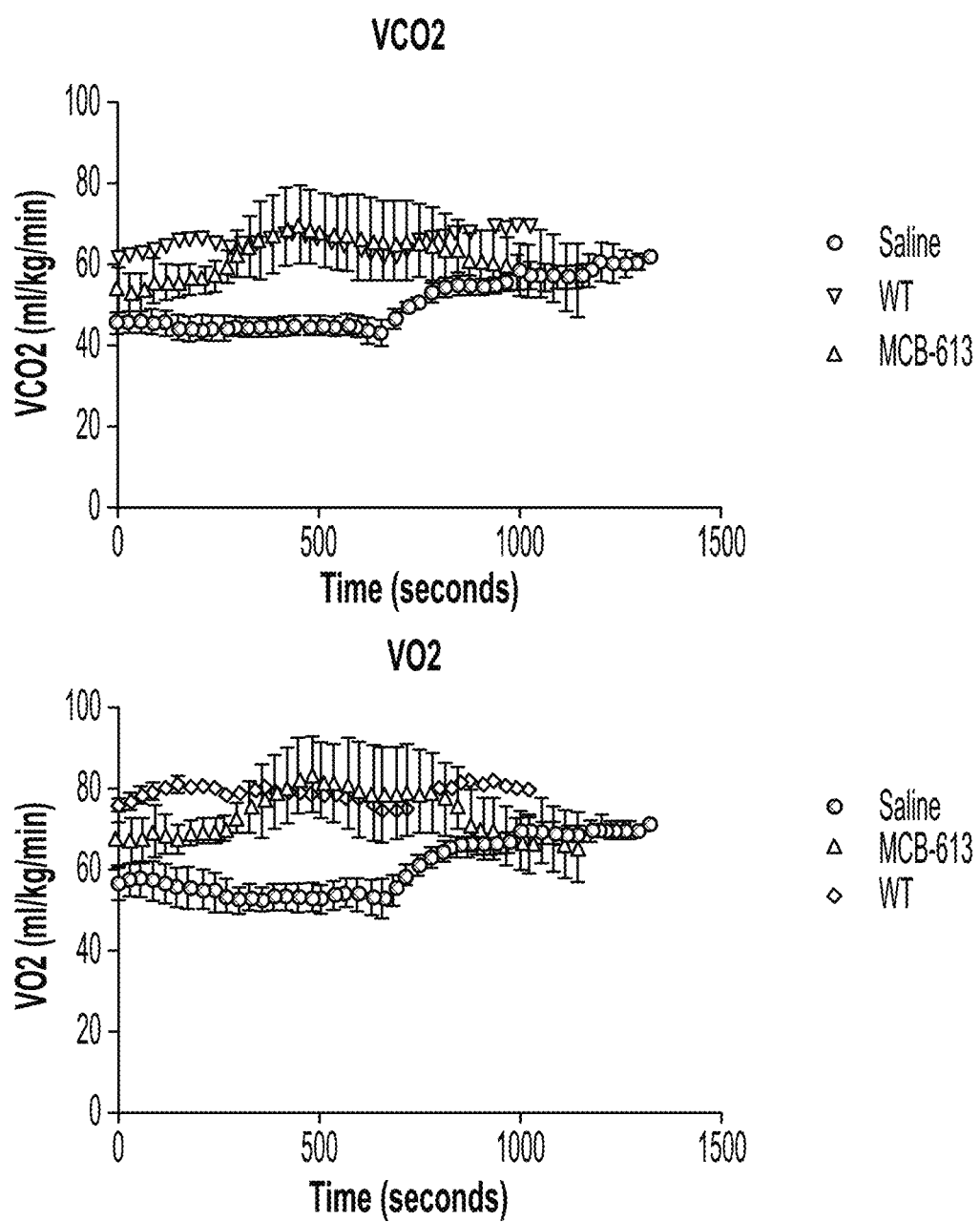
FIG. 9 contains graphs showing the results of a progressive maximal exercise test in mice treated with saline ("saline"), mice treated with MCB-613 ("MCB-613), and non-infarcted wild-type mice ("WT"). The upper panel shows the carbon dioxide expiration and the lower panel shows the oxygen consumption.

Compound 10-1 improves cardiovascular fitness after myocardial infarction. FIG. 9 contains graphs showing the results of a progressive maximal exercise test in mice treated with saline ("saline"; n=3), mice treated with MCB-613 ("MCB-613"; n=3), and non-infarcted wild-type mice ("WT"; n=2). The upper panel shows the carbon dioxide expiration ($VCO_2$) and the lower panel shows the oxygen consumption ($VO_2$). As shown in FIG. 9 through representative Compound 10-1, the compounds described herein improves cardiovascular and peripheral vascular fitness after myocardial infarction.

Summary

As shown by the data presented herein, the compounds described herein stimulate angiogenesis in vivo and improve the function of injured myocardium. Thus, the compounds described herein are exceptional therapeutic agents that are useful in repairing and preventing chronic wounds, promoting angiogenesis, restoring blood flow in vascular diseases, and constraining detrimental structural remodeling of vulnerable myocardium by preventing metabolic remodeling. The compounds are useful for cardiac repair after coronary insufficiency.

Example 3: Cardiac Protection Promotion and Repair after Myocardial Infarction Using Steroid Receptor Coactivator Stimulator Progressive remodeling of cardiac tissue with loss of myocytes, inflammation, fibrosis and decrease in cardiac ejection fraction are hallmarks of myocardial infarction (MI)-induced heart failure. A key therapeutic goal after MI is to protect the myocardium, minimize infarct size, prevent progression to heart failure, and to support functional recovery. The data herein show that the small molecule stimulators of steroid receptor coactivators described herein promote new vessel growth and improve cardiac function following MI. As shown through a representative compound, administration of small molecule receptor coactivator stimulators decreases infarct size, apoptosis, cardiac hypertrophy, collagen deposition, and activates cardiomyocyte energetic pathways. Single-cell transcriptional profiling identified distinct interstitial cell types and transcriptional responses associated with improved cardiac function. The compounds described herein represent novel therapeutic option for preventing early and progressive loss of cardiac function after MI.

Methods

Animals. All animal studies and protocols were approved by the Institutional Animal Care and Use Committee at Baylor College of Medicine and conducted in strict accordance with the *National Institutes of Health Guide for the Care and Use of Laboratory Animals*. Adult (8-10 week old) ICR (CD1) mice were used for all studies.

Angiogenesis assay for small molecule stimulator treatments. Five to seven day old specific-pathogen-free (SPF) certified fertilized chicken eggs (white leghorn) were used to access the chorioallantoic membrane (CAM). The total vessel area on the CAM was measured using images obtained prior to application of the drug. MCB-613 (100 µL) at a concentration of 0.6 µM was topically applied onto the surface of the CAM. The vessel area on the CAM was monitored on a daily basis following daily application of the drug. Vehicle controls were maintained throughout the experiment. Treatments were continued for four days at the end of which an image thresholding method (ImageJ) was used to quantify total vessel area on the CAM. Percent growth in vessel area was compared for control and treated eggs. n=6 eggs per condition. This experiment was repeated three times.

Angiogenesis Assay with drug treated mouse embryonic fibroblasts (MEFs). Five to seven day old SPF certified fertilized chicken eggs (white leghorn) were used to access the chorioallantoic membrane (CAM). Mouse embryonic fibroblasts (MEFs) were treated with 0.6 µM MCB-613 for 24 hours. Post treatment, two million MEFs were suspended in 60 µL of PBS containing magnesium and calcium and 40 µL of Matrigel (2M/egg) (Corning Inc.; Corning, N.Y.). The MEFs were then mixed well by pipetting and transferred to the surface of the CAM. The vessel area on the CAM was monitored on a daily basis. Vehicle controls were maintained throughout the experiment. MEFs were allowed to grow on the CAM surface for four days at the end of which an image thresholding method (ImageJ) was used to quantify total vessel area on the CAM. Percent growth in vessel area was then compared across control and treated eggs (MEF treated versus untreated). n=6 eggs per condition.

Reporter assay. Cardiac fibroblasts were plated in six well plates and transfected with a GAL4 responsive luciferase reporter (pG5-luc) and expression vectors for a GAL4 DNA binding domain (GAL4-DBD) full length SRC-1, -2 or -3 fusion construct (pBIND-SRC-1, pBIND-SRC-2 or pBIND-SRC-3) or pBIND control using Lipofectamine 3000 (Invitrogen; Carlsbad, Calif.). Twenty-four (24) hours post transfection, cells were treated with 6 M MCB-613 or dimethyl sulfoxide (DMSO) and incubated overnight. Post treatment cells were lysed and total protein was isolated using the Promega luciferase assay system (Promega Life Sciences; Madison, Wis.). Protein concentration was measured using a Bradford assay (Bio-Rad Laboratories; Hercules, Calif.). Relative light units were measured and normalized to total protein concentration.

Model of heart failure in adult mice. To induce MI in eight- to ten-week-old mice, the left anterior descending (LAD) artery was permanently ligated. Briefly, mice were anesthetized with 2% isoflurane and then intubated. The heart was exposed by performing a thoracotomy through the fourth or fifth intercostal space and an 8-0 nylon suture was tied around the LAD. The initial dose of MCB-613 was administered intraperitoneally at 20 mg/kg, two hours after surgery. Subsequent injection at the same time of the day and same dose were given for six additional days, and then repeated doses were given for three days at week nine and week 16. Mice were harvested at the indicated time points for analyses.

Echocardiography. Cardiac function was determined by echocardiography (VisualSonics, Vevo 2100, 40 Mhz-550S probe). After alignment in the transverse B-mode with the papillary muscles, cardiac function was measured on M-mode images. Animal numbers for cardiac function in FIG. 11A are Day 0 control (17); MCB-613 (15), Day 1 control (10); MCB-613 (12), Day 14 vehicle (19); control (19), Day 56 control (12); MCB-613 (15), Day 70 control (8); MCB-613 (10), Day 80 control (8); MCB-613 (11), Day 133 control (3); and MCB-613 (3).

Histological analysis. Whole hearts were fixed with 10% formalin, embedded in paraffin, and sectioned at 7 m intervals. Each slide had three (3) to ten (10) sections, which started at the apex and ended at the suture ligation site (approximately 30-50 slides). Sections at the papillary level (slides 20-30) were stained with Picrosirius red to identify areas of fibrosis. Infarct size was determined using a length-based approach. TUNEL staining to detect apoptotic cells was performed using the DeadEnd™ Fluorometric TUNEL System (Promega, GS3250).

Electron Microscopy. Animals were sacrificed and hearts were quickly removed and placed directly into cold primary fix (2% paraformaldehyde+2.5% glutaraldehyde+2 mM $CaCl_2$) in 0.1 M cacodylate buffer, pH 7.4) where they were sliced in cross-section then held in cold primary fix for four days. After fixation, tissues were stained with 0.1% tannic acid in 0.1 M cacodylate buffer, rinsed and osmicated for one hour, after which the tissue was rinsed in $dH_2O$ and counter-stained in aqueous uranyl acetate. Once again, the tissues were rinsed in $dH_2O$ and then dehydrated in a gradient series of ethanol (50, 70, 80, 90, 95, and 100%). Tissues were slowly infiltrated over a period of four days with increasing dilutions of plastic resins to ethanol, respectively, until 100% plastic was reached. After a full day of infiltration in three changes of 100% plastic, the tissues were embedded in freshly made Spurr's Low Viscosity resin and polymerized at 60° C. overnight. Ultra-thin sections of 55-65 nm were cut with a Diatome Ultra 45 diamond knife, using a Leica UC7 ultramicrotome. Sections were collected on 150 hex-mesh copper grids and viewed on a Hitachi H7500 transmission electron microscope. Images were captured using an AMT XR-16 digital camera and AMT Image Capture, v602.600.51 software.

Isolation of cardiac cells. Mice were placed under the surgical plane of anesthesia before cervical dislocation. The hearts were removed and cells were isolated by Langendorff retrograde perfusion of calcium-free pH 7.4 Tyrodes solution (130 mM NaCl, 74.55 mM KCl, 0.5 mM MgCl, 0.33 mM $NaH_2PO_4$, 0.25 mm HEPES, 22 mM glucose) with collagenase, 1 mg/mL for 15 minutes. The hearts were then removed from the apparatus, and finely minced in the same Tyrodes buffer with 15 mg/mL BSA before trituration with a glass pipette. Cardiomyocytes were then pelleted by differential centrifugation, 300 RPM for 3 minutes. The supernatant containing the noncardiomyocyte population of cells was then filtered through a 70 micron filter and pelleted at 750 g, and resuspended in 1.1 mL 2% fetal bovine serum (FBS) in phosphate buffered saline (PBS). Then, 0.1 mL of the mixture was removed for the "no stain control" for fluorescence-activated cell sorting (FACS). The other 1 mL of the mixture was incubated with 4 µg/mL Calcein Blue and 10 µM DyeCycle Ruby and incubated at 37° C. for 10 minutes. The cells were then spun down at 600 g, and resuspended in 0.5 mL 2% FBS/PBS containing Sytox Green (30 nM). Cells were then sorted for: Sytox Green-, Calcein+, DyeCycle Ruby+ into 0.4% FBS in PBS using a FACS Aria ii cell sorter. The cells were then pelleted and resuspended in 100 µL 0.4% FBS in PBS, counted, and passed through the 10× Genomics Chromium system.

Single-cell RNA-sequencing. Raw fastq files were imported into Cell Ranger 2.1.1 (10× Genomics) for alignment with STAR, filtering, barcode counting, and UMI counting. To identify cell clusters and differentially expressed genes, the Cell Ranger results were analyzed with Seurat suite version 3.0.0 implemented in R (version 3.4.3). Cells with <200 or >5,000 unique genes expressed or >25% of reads mapping to mitochondria were removed as quality control measure. Filtered data was normalized and scaled within each sample and both wild type and treated samples were aligned with Seurat's alignment procedure for integrated analysis. Wilcoxon rank sum test incorporated within Seurat was used to identify differentially expressed genes across cell types or treatment. Gene ontology analysis was performed with a custom code developed in python that utilizes hyper-geometric distribution to identify enriched pathways (P-value <0.05).

To study the effect of treatment on cell-to-cell communication in infarcted heart, curated and putative ligand-receptor pairs in human were obtained. For each cell type, a signature for drug treatment was obtained by applying a filter of P-value<0.05 & log 2FC>0.25 or <−0.25. Cell-to-cell communication was built by linking cell types A and B, where ligand was differentially expressed in cell type A while receptor is differentially expressed in cell type B. The network was plotted using the igraph R package.

Total RNA-Seq analysis. Sequencing reads were trimmed using the trimGalore software. Next, the reads were mapped using HISAT against the human genome build UCSC mm10, and quantified using StringTie against the Gencode gene model. Gene expression (FPKM) was quantile normalized using the R statistical system. Differentially expressed genes between tumor and normal samples were determined using a parametric t-test with p-value <0.05 and fold change of 1.25. Pathway enrichment analysis was carried out using the GSEA software package; significance was achieved for adjusted q-values (q<0.25). Heatmaps were generated using the using Matplotlib, NumPy and SciPy libraries under python.

RNA isolation and qPCR. Total RNA was isolated from cells using the Qiagen RNA isolation kit. cDNA was prepared with the VILO master mix reagent. qPCR analysis was carried out using the Taqman kit with primers for Tlr7, Lcn2 and 18s.

Granulocyte isolation. Bone marrow cells were isolated from the rear legs of mice treated with control or MCB-613 for 24 hours. Rear legs were removed and placed in ice-cold Hanks balanced salt solution (HBSS) (without Ca/Mg) plus 2% FBS. Both ends of the bone were cut and the bone marrow was flushed with ice cold HBSS with 2% FBS using a 26G needle. Clumps were broken up with an 18G needle and filtered through a 70 µm filter and centrifuged at 400 g for 10 min at 4° C. The pellet was suspended in RBC lysis buffer (BD Biosciences Pharmigen; San Diego, Calif.) and incubated at room temperature for two minutes. HBSS buffer (8 mL) was added and spun at 400 g for 10 mins at 4° C. Viable cells were counted by trypan blue exclusion and bone marrow granulocytes were isolated using a mouse Neutrophil Isolation Kit from Miltenyi Biotec (Bergisch Gladbach, Germany).

Flow Cytometry and Cardiac Immune Phenotyping. Hearts and spleens isolated from control and MCB-613 treated mice 24 hours post-MI or post-sham surgery were digested in digestion buffer: 500 µL of DNAse I (10 mg/ml), 500 µl Collagenase II (50 mg/ml) into 4 ml (enough for approx. 12 spleens @ 1×) RPMI 1640. Cells were placed on a GentleMacs dissociator and run on "IMPC_step2" twice and incubated at 25° C. for 15 minutes. The "IMPC_step2" program was repeated and the samples were incubated at 25° C. an additional 15 minutes followed by another round of the "IMPC_step2" program. Then, 400 µL of 4° C. Stopping Buffer (1× PBS, 0.1M EDTA) was added to each sample and centrifuged at ~100 g for one second to collect liquid at the bottom of tube. Samples were filtered through mesh filter caps into 50 mL conical tubes. The tubes were then washed with 1 mL FACs buffer which was also then passed through the filter. Heart preps were more viscous and were washed with 20 mL cold filtered saline. Samples were centrifuged at 500 g for 6 minutes. Supernatant was discarded and the pellet suspended in 1 mL 4° C. FACS buffer. Following red blood cell (RBC) lysis and blocking, single cell suspensions were stained with an immune cell panel and quantified using an LSR II flow cytometer. Then, 500,000 live events were counted for spleen controls and the entire tube of heart cells was recorded and analyzed.

Western blots. Frozen whole hearts were pulverized using a mortar and pestle apparatus. Approximately 20 mg of powdered tissue was added to 300 µL of radioimmunoprecipitation assay (RIPA) buffer and homogenized using a tissue homogenizer. Samples were then incubated on a rotator platform at 4° C. for one hour followed by centrifugation at 12,000 g for 10 minutes to clear debris. Supernatants were collected and stored at −80° C. for future use. Protein concentration was determined using the bicinchoninic acid assay (BCA) reagent system. For cell lysates, NETN buffer with 10% glycerol was used to lyse cells and isolate total protein. All lysis buffers were supplemented with protease and phosphatase inhibitors. Tissue lysate protein (30-50 µg) or cell lysate protein (50-70 µg) was loaded onto a 4-15% gradient gel (Bio-Rad) and transferred onto a polyvinylidene difluoride (PVDF) membrane. Immunoblotting was carried out using antibodies for SRC-1, SRC-2, SRC-3, actin and Hsp90. HRP conjugated anti-rabbit and anti-mouse secondary antibodies were used at dilutions of 1:2,500. Pierce ECL was used for chemiluminescent detection.

Tube formation assay. Cardiac fibroblasts were treated with either DMSO or 6 µM MCB-613. Twenty four hours post treatment, drug was washed off by rinsing the cells twice with PBS. The cells were then conditioned with endothelial cell growth media for 24 hours. Post conditioning, cells were plated on growth factor reduced matrigel (10 mg/ml) to allow for tube formation overnight. The next day tubes were stained with Calcein AM and imaged using the Cytation imaging system.

Immunostaining. Hearts were perfused with cardioplegic 20 mM KCL-PBS and then with 10% neutral buffered formalin before drop fixing and then processing into paraffin wax. Sections (7 microns) were then cut and placed onto slides. Immunofluorescence was performed by first removing the paraffin and then rehydrating the sections. After that, antigen retrieval was performed (Antigen unmasking solution, Tris-based, Vector Labs cat #H-3301; Vector Labs, Burlingame, Calif.). Sections were permeabilized with 0.1% tween20-PBS, blocked with 10% donkey serum in 1% tween20-PBS, and then incubated with primary antibody in blocking solution (1:200 Rabbit anti-Lysozyme, abcam cat #AB108508; Abcam, Cambridge, United Kingdom), followed by secondary (1:200 Donkey anti-Rabbit, Alexa 647, Thermo Fisher Scientific cat #A-31573; Thermo Fisher Scientific, Waltham, Mass.), and then Rhodamine-conjugated WGA (1:250 Vector Labs Cat #RL-1022) and DAPI (1:500 Thermo Fisher Scientific Cat #62248). Images were taken on a Zeiss LSM780 confocal microscope. LYZ+ cells were counted manually from random images spanning the entire myocardium of the left ventricle below the left anterior descending coronary artery occlusion surgery. n=3 hearts/group, >10 mm$^2$ imaged/heart, 24 hours after MI surgery.

RER, VO$_2$ and VCO$_2$ measurements. RER, V02 and VCO$_2$ were measured by indirect calorimetry using a progressive maximal exercise test until mice reached exhaustion.

Results

Figure 10C:
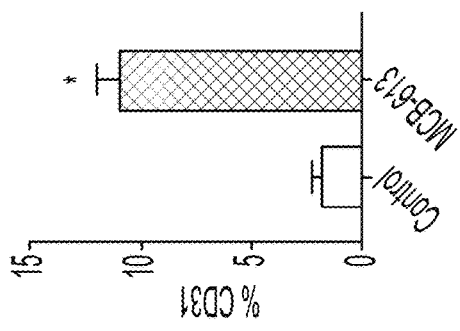
FIGS. 10A-10E show that MCB-613 stimulates angiogenesis in chicken eggs and in mouse hearts three days post-MI. For FIG. 10A, cardiac fibroblasts were treated with DMSO or MCB-613 for 24 hours. Total protein was then isolated and immunoblotted for SRC-1, -2 and -3. Hsp90 was used a loading control. For FIG. 10B, cardiac fibroblasts were transfected with a GAL4 DNA binding site-luciferase reporter (pG5-luc) and GAL4-DNA binding domain-full length SRC-1, -2 or -3 fusion (pBIND-SRC) or control pBIND expression vectors. Post transfection, cells were treated with DMSO or MCB-613 for 24 hours. Total protein was isolated and measured for luciferase activity. Relative light units (RLU) were calculated by normalizing the luciferase activity to total protein concentration (n=3) (*P<0.05). For FIG. 10C, cardiac fibroblasts were treated with DMSO or MCB-613 for 24 hours and then conditioned with endothelial growth media without drug for an additional 24 hours. Conditioned cells were then plated in matrigel to allow tube formation overnight and tubes were then stained with Calcein AM dye and imaged. For FIG. 10D, chicken eggs were treated with DMSO or MCB-613 and vessel area was measured at days one and three. Mouse embryonic fibroblasts (MEFs) were treated with dimethyl sulfoxide (DMSO) or MCB-613 for 24 hours then placed on a membrane in chicken eggs. Vessel area was measured at days one and three. Data are presented as percent increase over control for each condition. Six eggs were used for each condition *P<0.05. For FIG. 10E, mice were treated with MCB-613 or control two hours post-MI. Hearts were fixed and immunostained for endothelial-cell-specific CD31.
Figure 10E:
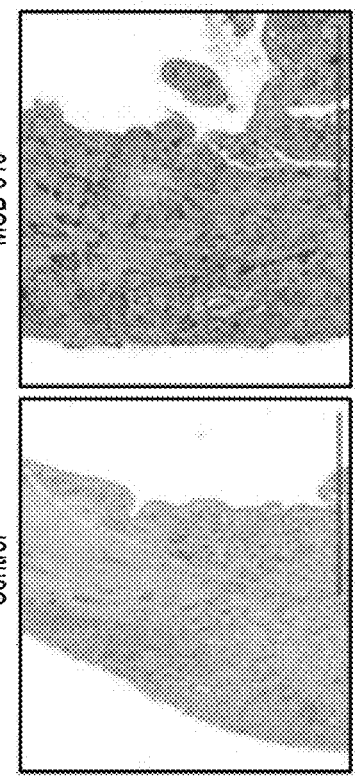
Figure 10B:
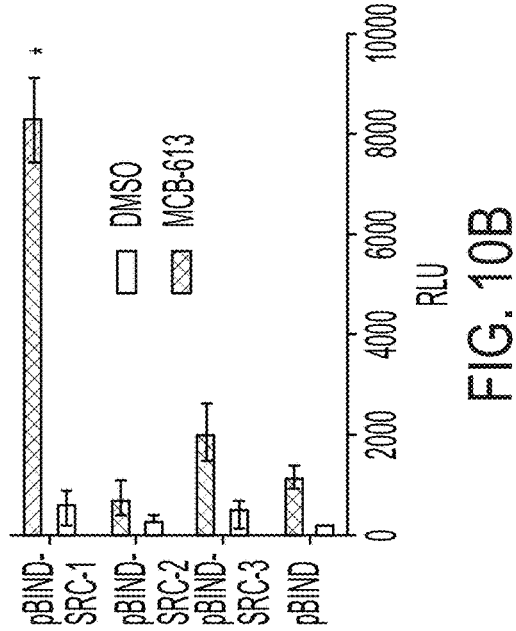
Figure 10A:
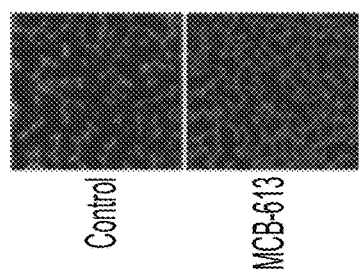
Figure 10D:
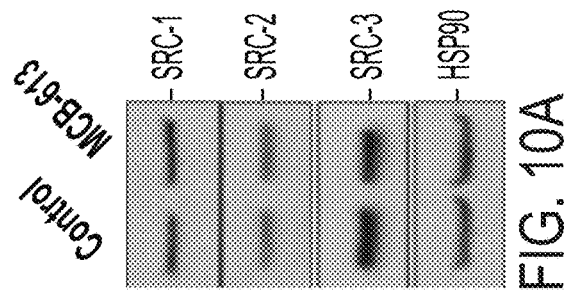

MCB-613 stimulates angiogenesis. The effects of MCB-613 on angiogenesis and stromal response, specifically in adult cardiac fibroblasts, was studied. SRC-1, 2, and 3 proteins were expressed in adult cardiac fibroblasts isolated from 10 week old mice (FIG. 10A). Cardiac fibroblasts were transfected with expression vectors for GAL4 DNA binding domain-SRC-1, 2, and 3 fusion proteins and a GAL4-responsive luciferase reporter to measure SRC activation following MCB-613 treatment (FIG. 10B). SRC-3 activity was induced in response to MCB-613 to a greater extent than for SRC-1 and SRC-2, indicating MCB-613 preferentially stimulates SRC-3 activity in cardiac fibroblasts. Functionally, MCB-613 stimulated tube formation in adult cardiac fibroblasts in vitro (FIG. 10C). To investigate MCB-613's stimulation of angiogenesis in vivo, a chick-egg angiogenesis assay was performed (FIG. 10D). Administration of MCB-613 directly to chick eggs stimulated angiogenesis in vivo. Additionally, introduction of mouse embryonic fibroblasts pre-stimulated with MCB-613 promoted robust angiogenesis likely in a cell non-autonomous manner. Not to be bound by theory, these findings indicate that MCB-613 stimulation of angiogenesis may occur through multiple mechanisms.

To determine whether MCB-613 ameliorates recovery after ischemia-induced myocardial injury, MCB-613 or vehicle control was administered to mice two hours following myocardial injury induced by permanent surgical ligation of the left anterior descending coronary artery. Increased angiogenesis was observed in the infarct border zone three days post-MI indicating that MCB-613 promotes angiogenesis in injured tissues and restores blood flow in the setting of vascular diseases (FIG. 10E).

Figure 11E:
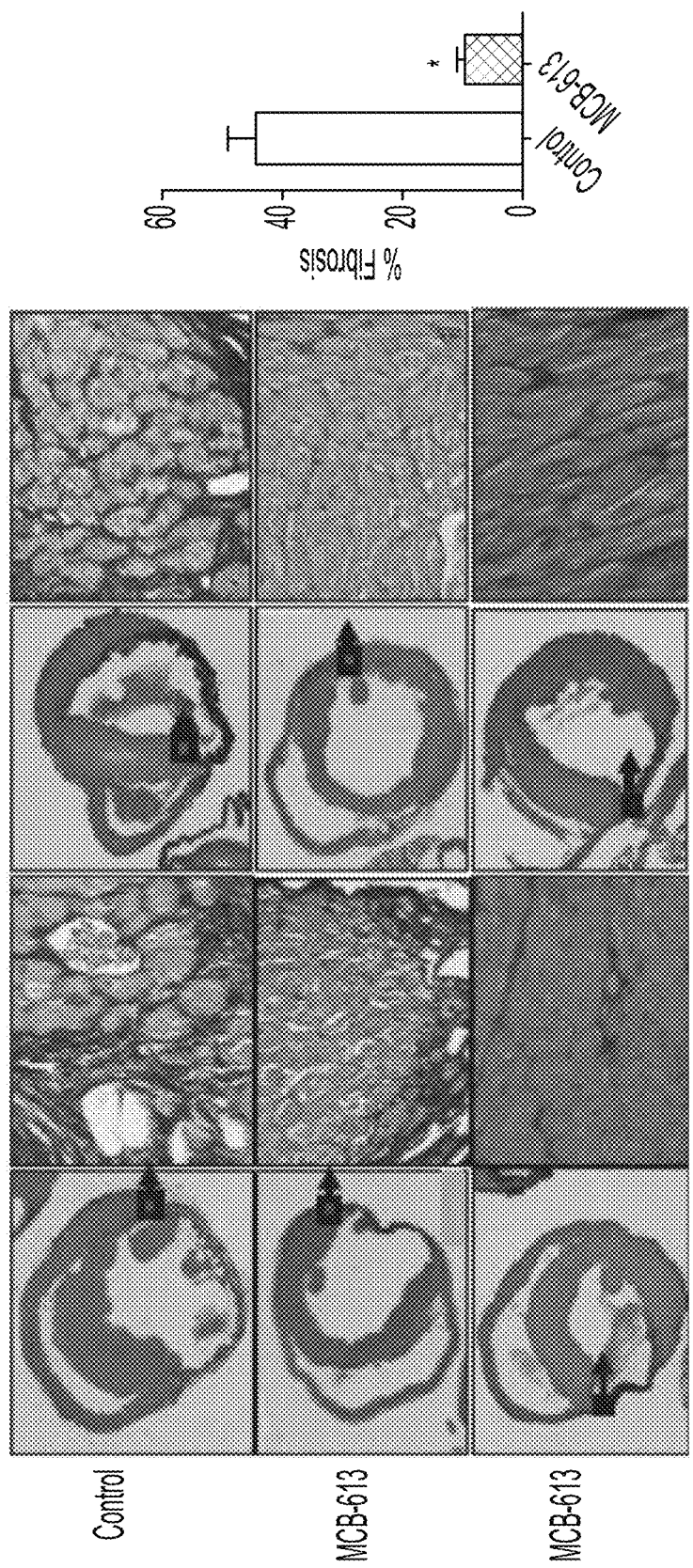
Figure 11G:
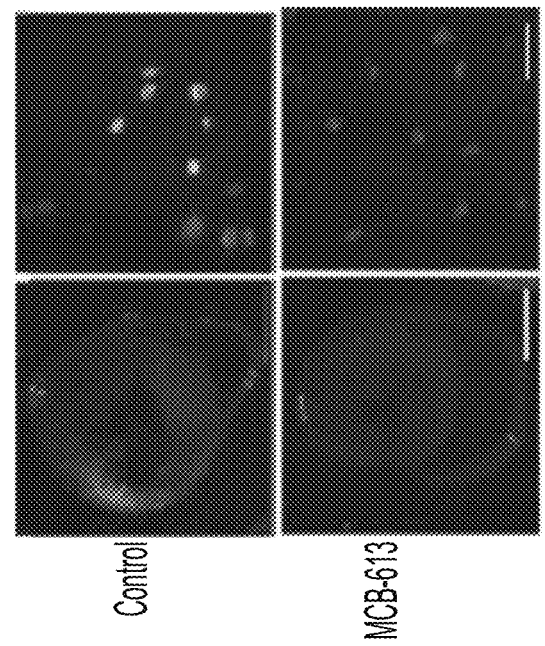
Figure 11F:
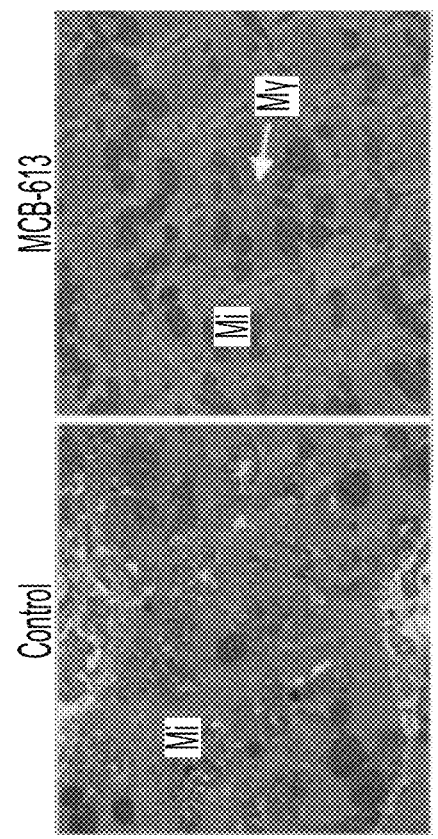
Figure 12:
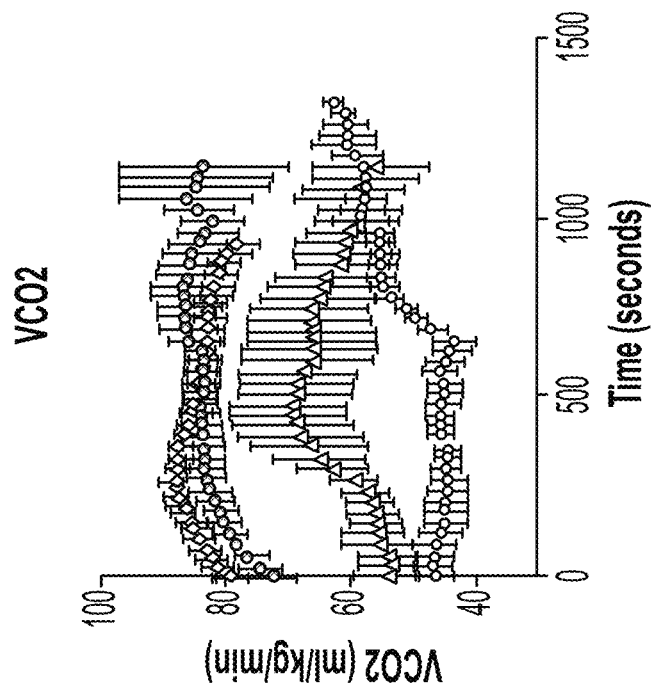
FIG. 12 contains graphs showing the results of a progressive maximal exercise test in non-infarcted wild-type mice treated with saline ("WT saline"), non-infarcted wild-type mice treated with MCB-613 ("WT MCB-613"), mice treated with saline post-MI ("MI saline"), and mice treated with MCB-613 post-MI ("MI MCB-613"). The left panel shows the oxygen consumption and the right panel shows the carbon dioxide expiration.
Figure 12:
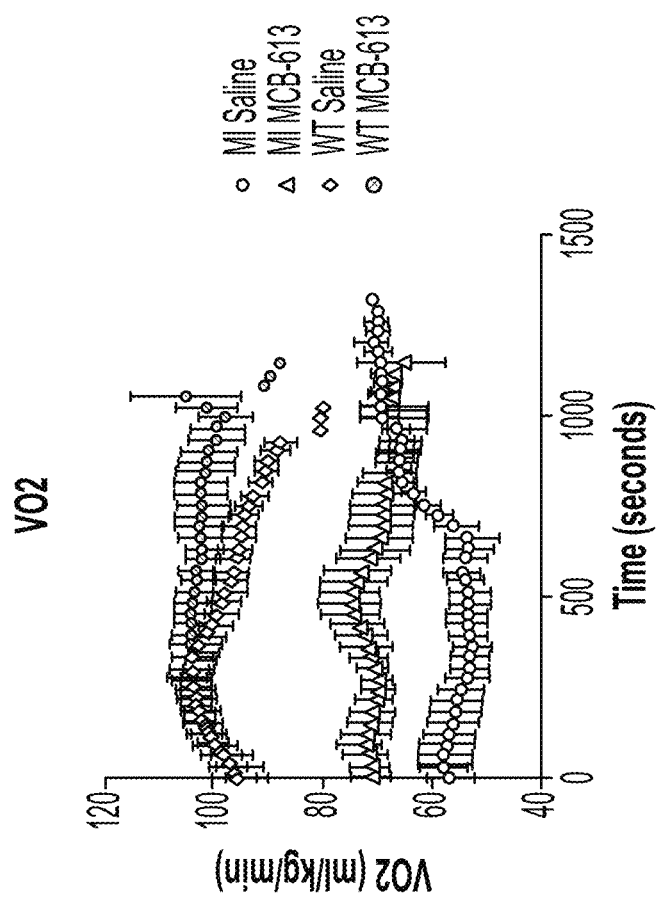

MCB-613 prevents loss of cardiac function after MI. Surgical ligation of the mouse left anterior carotid artery is a commonly used pre-clinical MI model for testing cardiovascular therapeutic interventions. To explore the role of SRC stimulation on early and late post-infarction cardiac function and remodeling, mice that received MIs were treated with MCB-613 or vehicle control. Mice were given 20 mg/kg MCB-613 or control vehicle by intraperitoneal injection two hours after MI surgery and every 24 hours for six additional days (FIG. 11A). Early and progressive loss of cardiac function after MI was measured by echocardiography prior to surgery, at 24 hours and at 2, 8, 12, and 19 weeks post-surgery. Ejection fraction decreased to an average of 30% in control-treated animals 24 hours post-MI. In contrast, mice treated with MCB-613 two hours post-MI had an average ejection fraction of 43%, indicating MCB-613 prevented the early decrease in ejection fraction and provided early protection to vulnerable myocardium (FIG. 11B). Ejection fractions in control-treated mice decreased further after 24 hours and was at its lowest 19 weeks post-MI, indicating progressive loss of cardiac function overtime. In contrast, ejection fractions were maintained above 40% from 24 hours post-MI until 19 weeks post-MI following administration of MCB-613, indicating that the early myocardial protective effects of MCB-613 prevents progressive loss of cardiac function. Repeat injections given for three days at weeks 8 and 16 did not alter ejection fractions, indicating MCB-613 had no further impact on cardiac function at later time points. Maintenance of cardiac function up to 19 weeks post-MI indicates that short-term early intervention may be effective in preventing congestive heart failure after MI. Analysis of heart weights reveals that MCB-613 attenuated the MI-induced cardiomegaly compensatory response 12 weeks post-MI (FIG. 11C), indicating that the preservation of cardiac function is correlated with prevention of another key feature of heart failure. Cardiac positron emission tomography (PET) imaging was then used to make a spatial assessment of myocardial viability. Improved $^{18}$F-FDG uptake in the infarct zone shows that MCB-613 preserves healthy myocardium 2 weeks post-MI (FIG. 11D). Heart tissue sections were stained with Picrosirius red to evaluate infarct size and degree of fibrosis (FIG. 11E). Infarct sizes measured 12 weeks post-MI were larger in control-treated hearts (31% and 44%) compared to hearts from MCB-613-treated mice (3%, 14%, 20% and 22%). In addition, cardiomyocytes were smaller and associated with less fibrosis in the infarct border zone, demonstrating that MCB-613 prevents two additional key molecular features of progressive heart failure (FIG. 11E). Cardiac metabolic dysfunction is a common feature of heart failure. SRCs coordinate diverse metabolic requirements in tissues including in skeletal and heart muscle. Indirect calorimetry with exercise was performed to determine the impact of MCB-613 on energy expenditure three weeks post-MI compared with age-matched mice without MI as a control (FIG. 12). $VCO_2$ and V02 are elevated in MCB-613 treated animals three weeks post-MI, indicating that MCB-613 can improve energy utilization during exercise in mice after MI. Thus, improved cardiac function is associated with improved energy expenditure. Electron micrographs of hearts 72 hours post-MI shows that MCB-613 can prevent disorganization of myofibrillar structure and abnormal mitochondrial cristal architecture, indicating that MCB-613 protects cardiac muscle and mitochondria from MI induced damage (FIG. 11F). In support of early myocardial protection, MCB-613 prevents apoptosis 24 hours post-MI (FIG. 11G). These findings indicate MCB-613 acts to directly preserve functional myocardium and prevent detrimental remodeling of cardiac tissue.

Figure 13A:
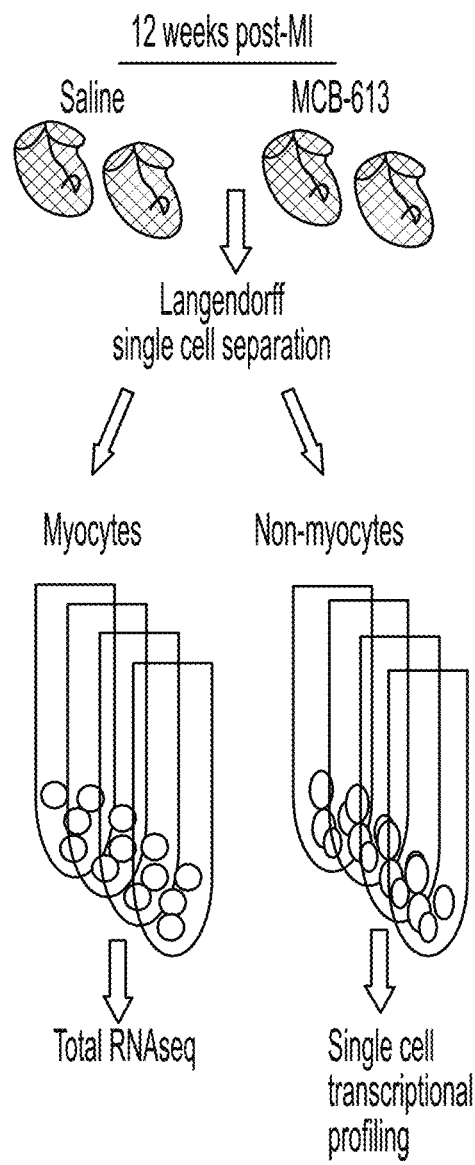
FIGS. 13A-13F shows RNA transcriptional profiling of cardiomyocytes and single cell analysis of interstitial cells 12 weeks post-MI that reveals that the MCB-613 protective response is associated with improved oxidative phosphorylation, decreased inflammation, and decreased immune cells.
Figure 13B:
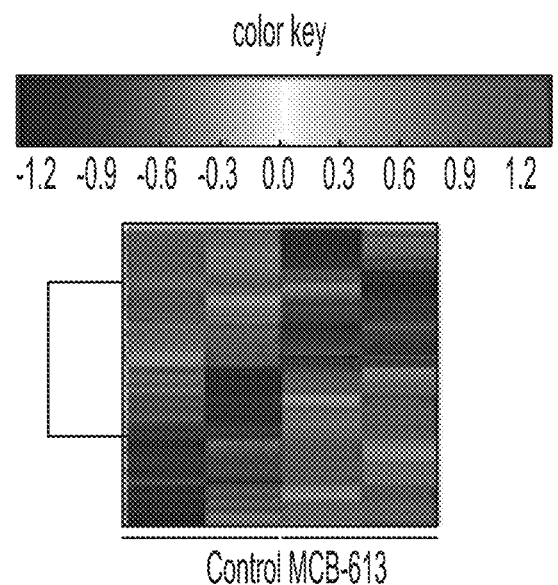
Figure 13C:
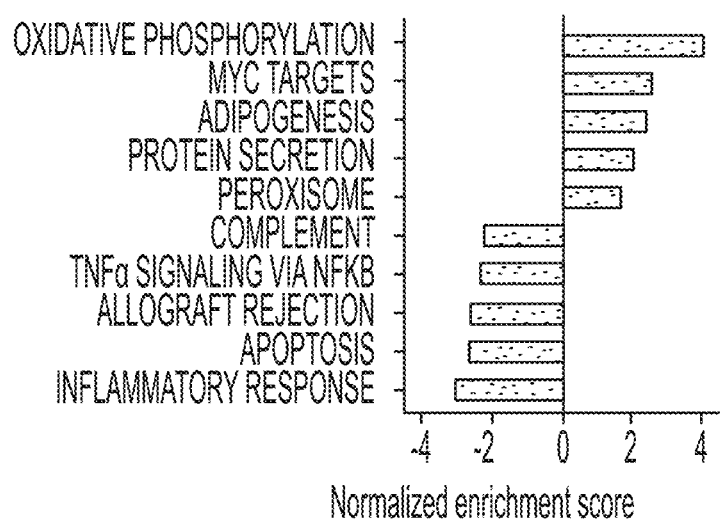

MCB-613 prevents cardiomyocyte damage response. To gain insight into cardiomyocyte- and non-cardiomyocyte-specific MCB-613 transcriptional functions associated with mitigation of myocardial remodeling and improved cardiac function, transcriptomic profiling was performed on cardiac cells purified from control-treated and MCB-613-treated mice 12 weeks post-MI (FIG. 13A). Differential gene expression analysis of cardiomyocytes indicates 122 upregulated genes and 107 downregulated genes are associated with improved cardiac function 12 weeks post-MI (FIG. 13B). Gene set enrichment analysis of differentially expressed genes displayed a strong enrichment for gene onogeny categories representing oxidative phosphorylation and adipogenesis and suppression of apoptotic and inflammatory response (FIG. 13C), providing further support that MCB-613 improves cardiac energy utilization in addition to preventing cardiomyocyte damage-associated signaling.

Figure 13D:
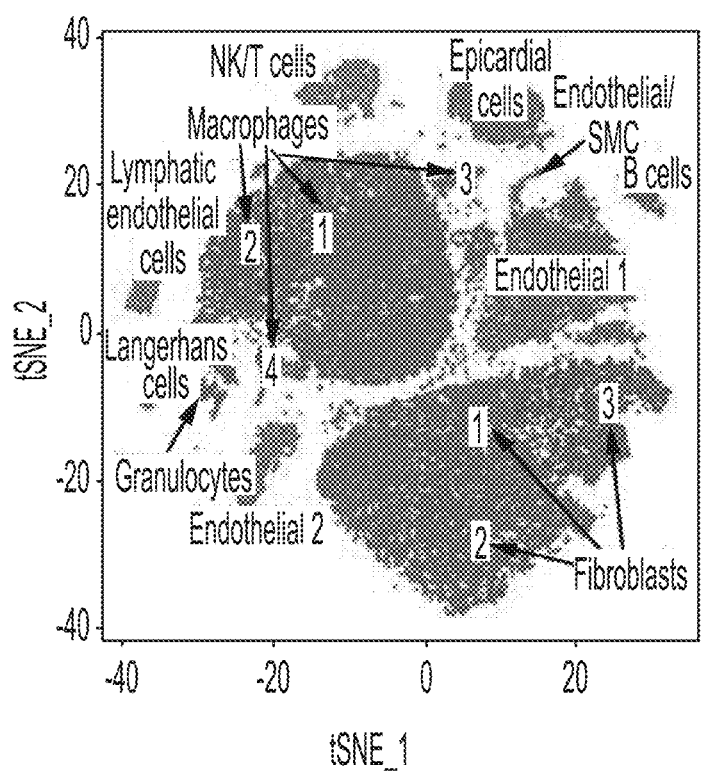
Figure 13E:
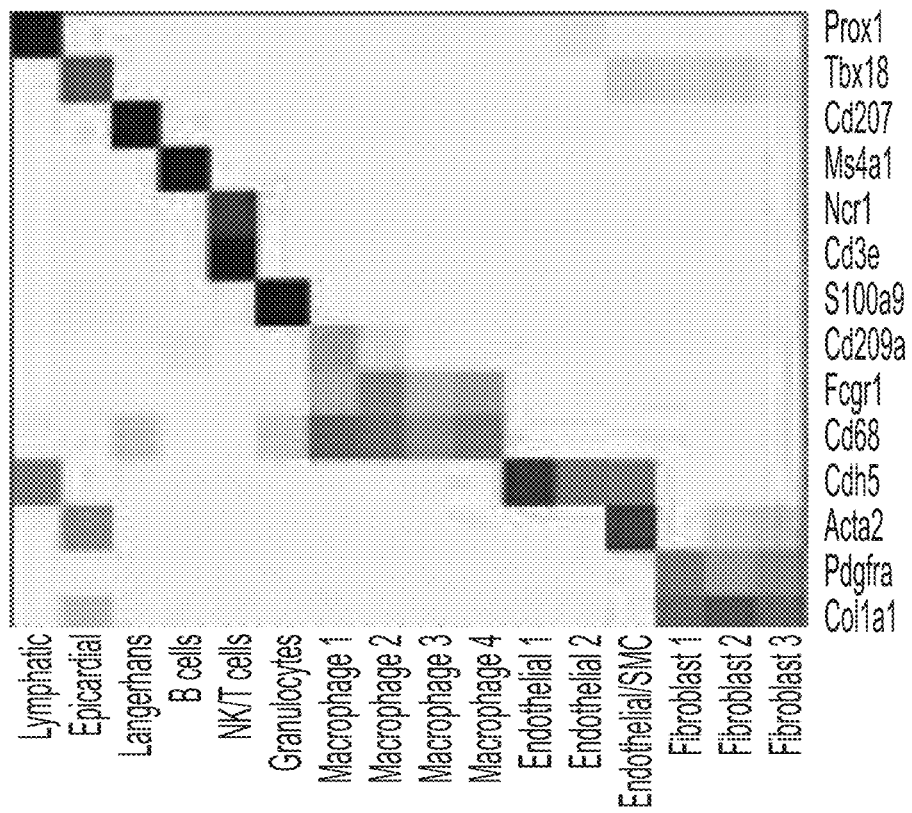
Figure 13F:
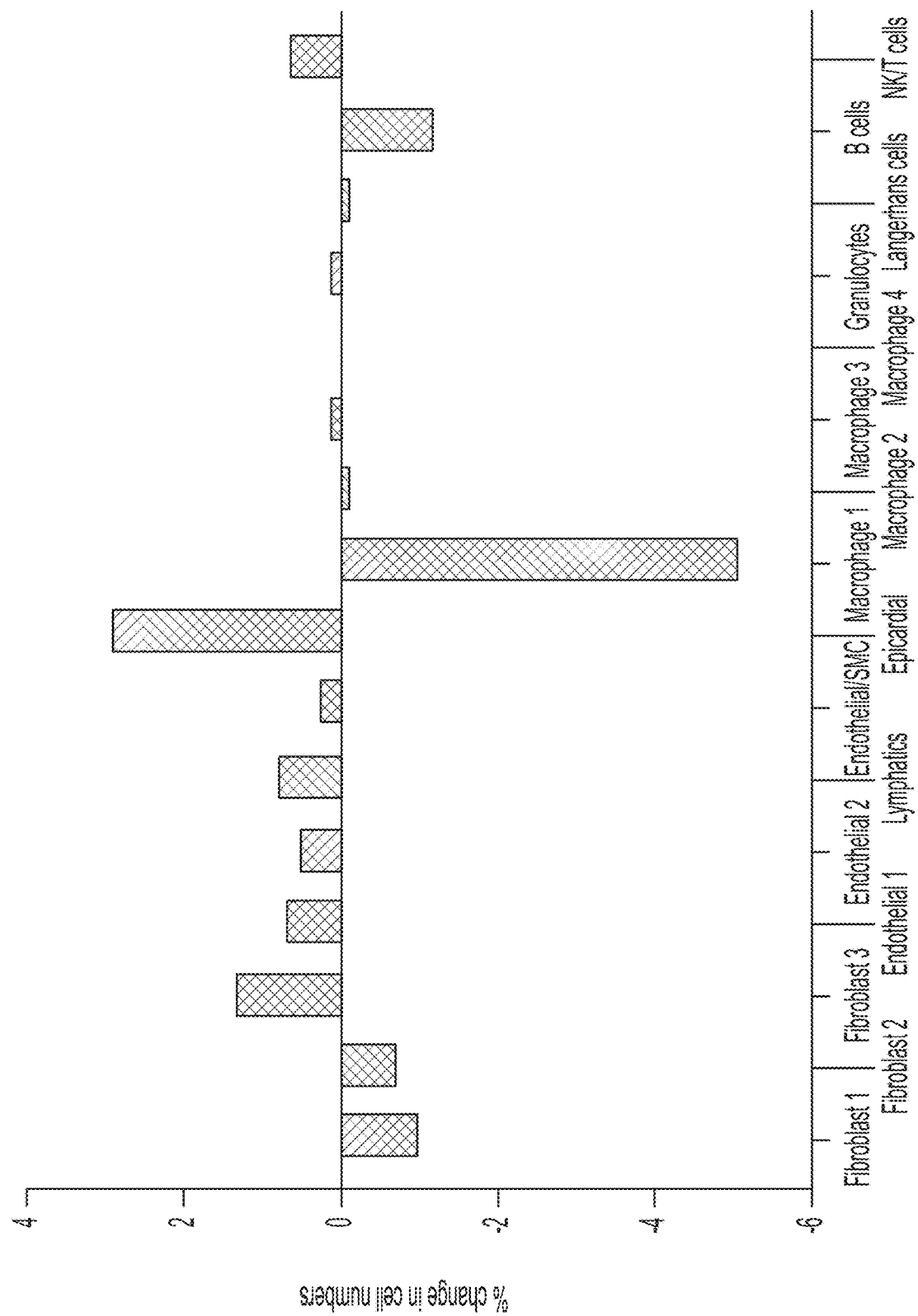

MCB-613 decreases inflammatory macrophages. Single cell transcriptomic profiling was performed to identify cell types and cell-type-specific signaling responses associated with improved cardiac function in MCB-613 treated mice 12 weeks post-MI. Metabolically active, viable, single cell suspensions of non-cardiomyocytes were prepared from whole hearts following Langendorff perfusion (FIG. 13A). Minimal procedural manipulations were performed to prevent loss of cell types and to minimize the impact on transcriptional activity. Transcriptional profiles of 21,894 cells from two saline-treated mice and 21,474 cells from two MCB-613 treated mice that passed RNA quality controls were analyzed using the 10× Chromium platform by Seurat analysis. Fifteen distinct cell clusters were identified based on cell expression patterns, unsupervised clustering and dimensional reduction analysis using Seurat software analysis (FIG. 13D). Cluster sizes ranged from 101 to 6,085 cells. Cell populations were identified based on known mouse cardiac cell type markers (FIG. 13E). At 42% of total cells analyzed, macrophages are the major non-cardiomyocyte cell population 12 weeks post-MI, unlike in normal adult mouse hearts where non-cardiomyocyte cells are comprised of only 10% hematopoietic-derived cells. Evaluation of the largest changes in cell number indicate macrophage cluster 1 and B lymphocytes decreased in number while epicardial cells, NK/T lymphocytes, fibroblasts, and endothelial cells, including lymphatic cells, were increased in cell number in hearts from MCB-613 treated mice (FIG. 13F). Cardiac macrophages, fibroblasts, and endothelial cell populations display transcriptional heterogeneity and consist of four, three, and two sub-clusters, respectively. Evaluation of unique gene signatures in cardiac fibroblasts reveal the presence of an injury-reactive fibroblast population expressing Postn (fibroblast cluster 2) and, in support of recently reported 'homeostatic fibroblasts' in remodeled hearts, fibroblasts in cluster 3 uniquely express Comp (FIG. 14A). Genes uniquely enriched in fibroblast cluster 1 indicate the presence of a fibroblast subpopulation involved in secretory functions that promote angiogenesis (Bmp4, Ecm1, Ccl11, Pgf) and extracellular matrix organization (Ecm2 and Pdgfra). Endothelial cell transcriptional signatures indicate the presence of 3 sub-populations. Endothelial cluster 2 and lymphatic endothelial cells exhibit increased transcriptional activation of 218 and 308 unique genes respectively, compared to endothelial cluster 1, indicating divergent roles in cardiac maintenance 12 weeks post-MI (FIG. 14B). The lymphatic endothelial cluster is defined by unique expression of lymphatic endothelial genes Prox 1 and Lyve 1. Concurrent expression of pro-angiogenic regulators Hif1a and Lrg1 and lymphangiogenic regulator Ccl121a, in addition to increased cell numbers, indicates MCB-613 stimulates lymphangiogenesis 12 weeks post-MI. The gene expression signature in endothelial cluster 2, defined by unique expression of early cardiac genes Mkl2, Tek and Hand2 indicates a transcriptional reversion to a more primitive cell state, likely due to an injury stress response. Not to be bound by theory, the largest endothelial cluster, endothelial cluster 1, represents endogenous homeostatic endothelial cells characterized by a small number of unique genes and the absence of any associated GO-terms or signaling pathways. Transcriptional signatures for four macrophage subclusters were clearly separable (FIG. 14C). Macrophage cluster 1, the largest subpopulation of macrophages, is defined by expression of an inflammatory gene signature including Ccl8, Cc24, and Ly96 compatible with these genes' role in the resolution of myocardial inflammation. Cluster 2 represents a population of Ccr2+ monocyte-derived macrophages that expresses inflammatory genes Cxcl1, Ccr2, Ccr5 and Tlr2 that are known to be short-lived infiltrating macrophages derived from bone marrow in response to injury. In contrast, macrophages in cluster 3 uniquely express 110 cell cycle proliferation genes indicating the presence of a small population of proliferating Ccr2-macrophages known to be maintained by local proliferation that play a role in tissue repair and myogenesis. Macrophages in cluster 4 are identified by the expression of genes involved in activation of phagocytosis including Cd209 and Coro1a, indicating the presence of a small population of phagocytic macrophages 12 weeks post-MI. Surprisingly, the rather small changes in cell population numbers associated with improved cardiac function maintenance indicates that MCB-613 cardioprotection is likely the result of cell functional changes instead.

Figure 15A:
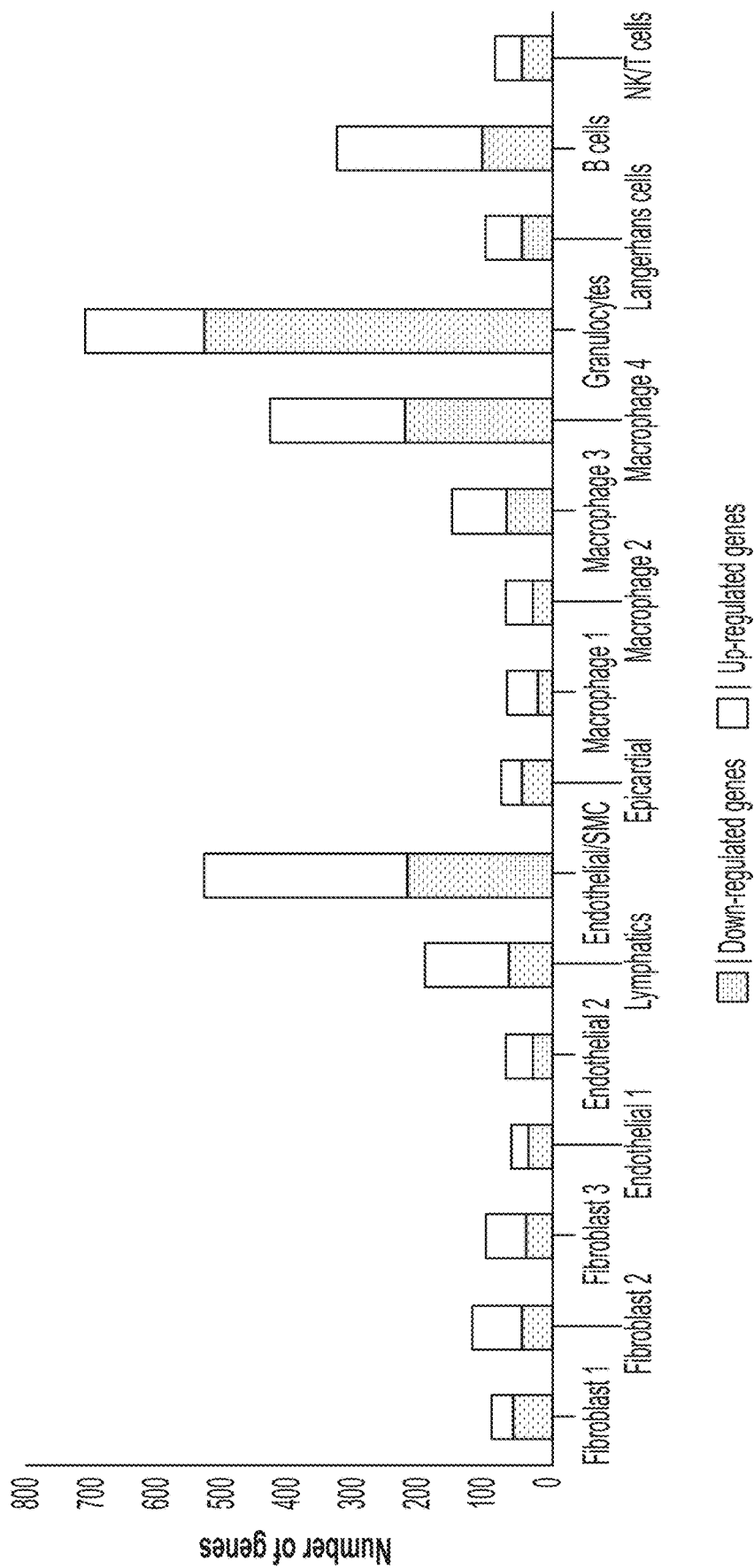
FIGS. 15A-15D show that MCB-613 regulates sustained immune and endothelial cell responses 12 weeks post-MI.
Figure 15B:
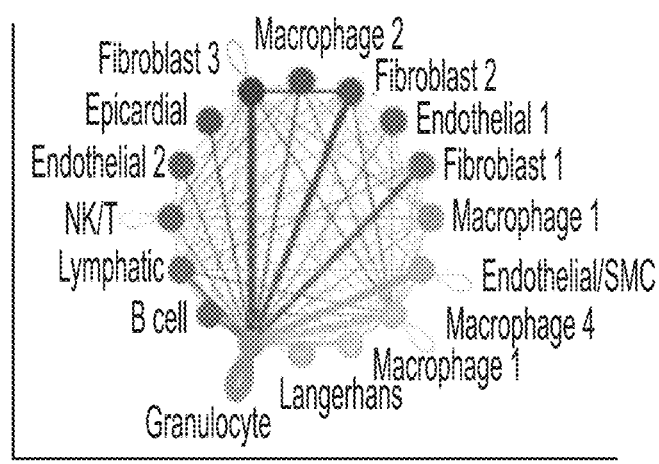
Figure 15D:
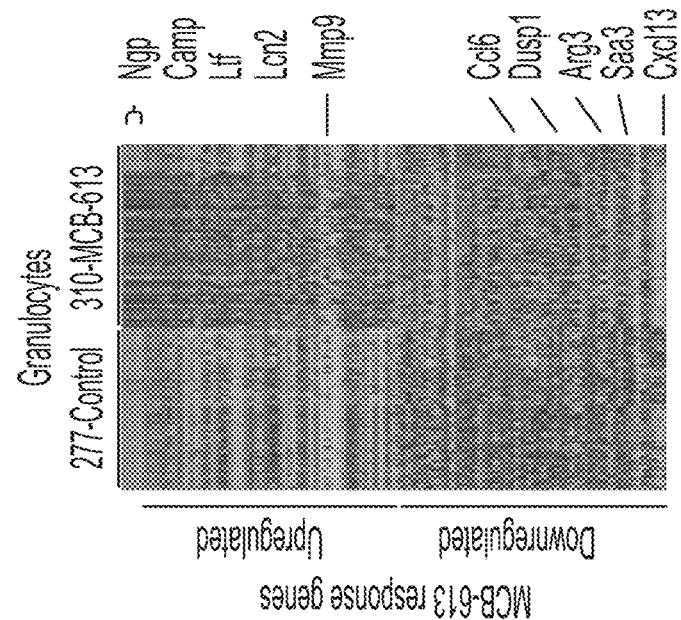
Figure 15C:
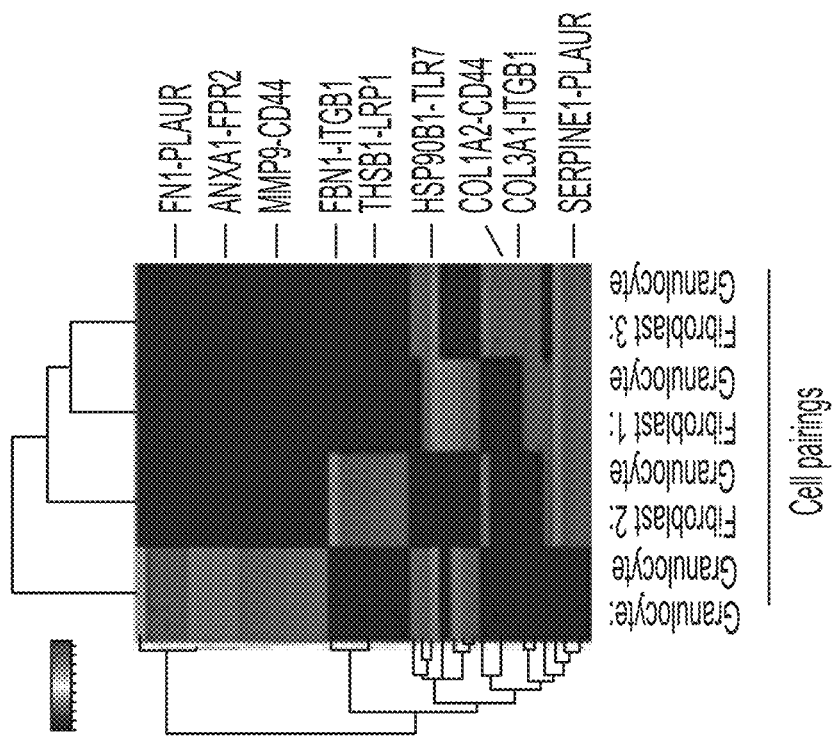

MCB-613 promotes salutary paracrine signaling. To determine interstitial cell-type functional responses associated with MCB-613 mediated improved cardiac function 12 weeks post-MI, transcriptomic profiles were compared in non-cardiomyocyte cells from control-treated and MCB-613-treated mice (FIG. 15A). Large variations in cell population transcriptional responses indicate MCB-613-selective cellular responses contribute to improved cardiac function. Smaller populations of cells consisting of lymphatic and immune cell populations experienced the largest drug-induced transcriptomic changes. To identify potential interstitial cell signaling interactions contributing to improved cardiac function, the number of interactions between ligands and receptors for each cell in control hearts compared to hearts from MCB-613 treated mice (FIG. 15B) was calculated. The highest frequency of interactions occurred between ligands from each fibroblast population, one macrophage subtype and the endothelial/SMC population broadcasting to granulocyte receptors. This pattern of interstitial cell signaling to granulocytes implicates extensive paracrine regulation of granulocyte functions in the MCB-613 cardioprotective response 12 weeks post-MI. Ligand-receptor pairings suggest coordinated regulation of tissue architecture and anti-inflammatory signaling pathways including MMP9-LRP1, HSP90B1-TLR7 and SERPINE1-TAUR (FIG. 15C). In support of this, gene set enrichment analysis of up and downregulated gene signatures in granulocytes indicates MCB-613 suppresses inflammatory granulocyte functions (FIG. 14D). The top up and down-regulated genes in cardiac granulocytes from MCB-613-treated mice compared to control reveals increased expression of granules involved in innate defense and decreased cytokines, enzymes and chemokines involved in inflammatory signaling (FIG. 15D). These findings indicate the myocardial response to MCB-613 is characterized by a sustained paracrine anti-inflammatory signaling landscape that underlies improved cardiac function.

Figure 16A:
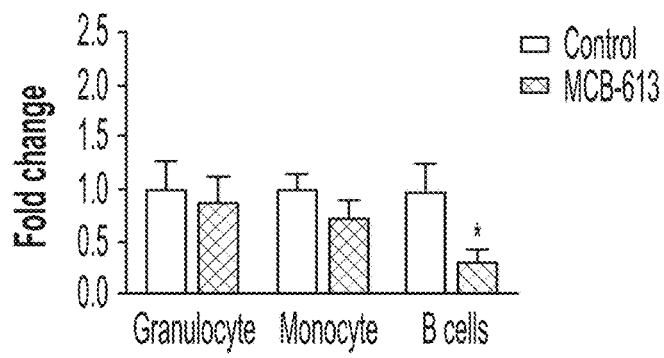
FIGS. 16A-16C show that MCB-613 decreases B lymphocytes and monocytes and upregulates granulocyte genes and lysozyme as early as 24 hours post-MI.
Figure 16B:
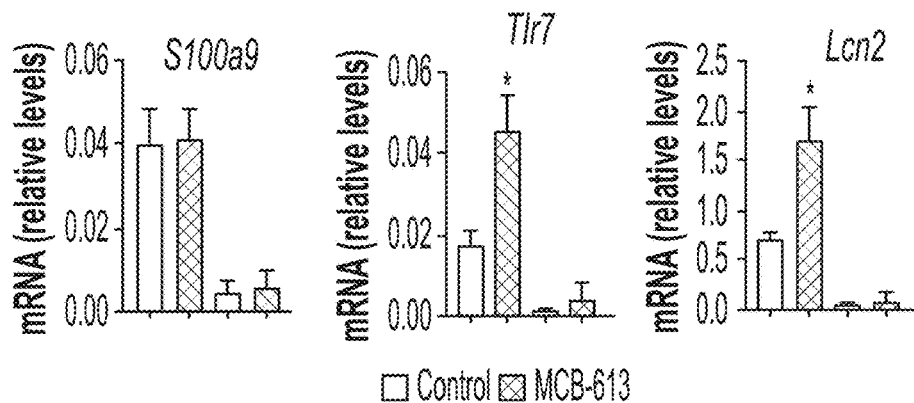
Figure 16C:
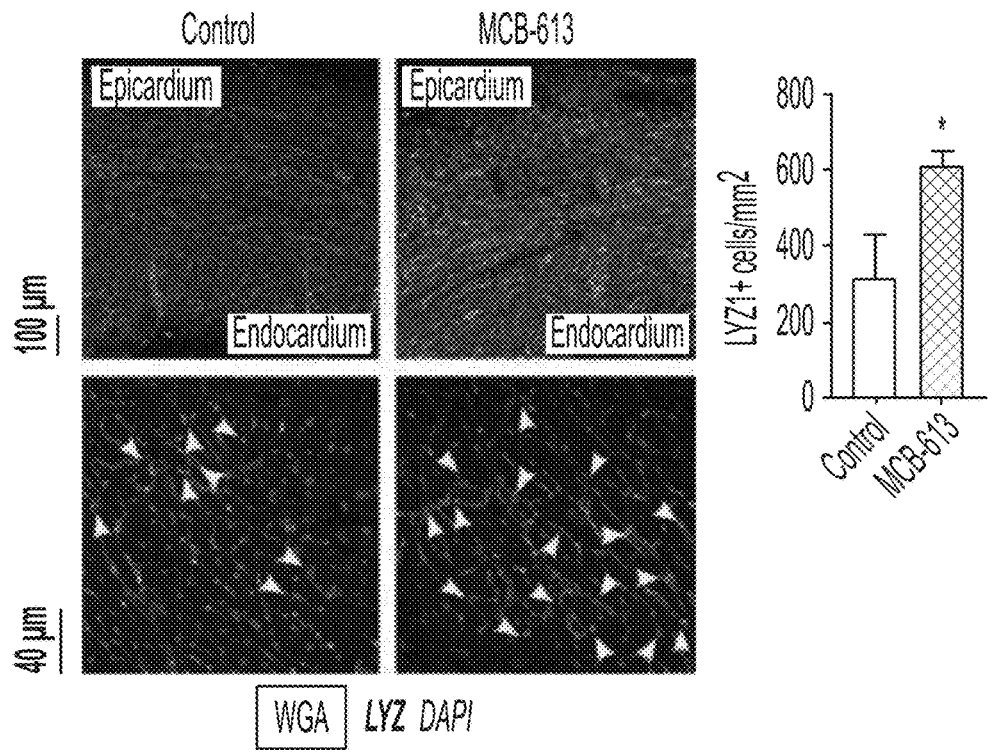

Since administration of MCB-613 at the time of injury resulted in an immediate response at 24 hours (FIG. 11B and FIG. 1E), the effect of MCB-613 on immune cells 24 hours post-MI was measured. Immune-phenotyping by FACS analysis of single cells isolated from whole hearts 24 hours post-MI was used to quantify the composition of immune cells. Similar to that seen at 12 weeks post-MI, there was a significant decrease in B cells, a trend for decreased monocytes and no change in the fraction of granulocytes in hearts from MCB-613 treated mice compared to controls (FIG. 16A). The acute granulocyte transcriptional response to MCB-613 due to the presence of paracrine signaling and the robust transcriptional response in granulocytes 12 weeks post-MI was then measured. Granulocytes are the first innate immune cells to reach the myocardium after acute ischemic injury and are critical mediators of the extent of the inflammatory reaction triggered by an acute heart attack and of the resulting damage to the heart muscle. Due to the difficulty of isolating sufficient quantities of undamaged granulocytes from mouse hearts, to investigate granulocyte responses bone marrow granulocytes were isolated, which reflect the myocardial granulocyte response 24 hours post-MI. Elevated mRNA expression of the granulocyte marker S100A9 in granulocytes compared to granulocyte-depleted bone marrow indicates successful isolation of granulocytes (FIG. 16B). Increased expression of Tlr7 and Lcn2 in granulocytes from mice treated with MCB-613 supports the single cell transcriptomic analysis and reveals that modulation of granulocyte function may contribute to the acute myocardial response to MCB-613. To control for the possibility that MCB-613 regulates Tlr7 or Lcn2 in bone marrow granulocytes as a result of tissue trauma from the surgical procedure in the absence of an MI, granulocytes were isolated from mice 24 hours following sham surgeries with administration of control vehicle or MCB-613. No changes in cell numbers or gene expression were observed, indicating that granulocyte gene expression changes are a consequence of MCB-613 mediated myocardial injury response. MCB-613 induction of a strong transcriptome response in granulocytes indicates that neutrophil granules can modulate the compound's post-MI inflammatory effects. In support of this, LYZ1 granule expression was significantly increased in the myocardium of MCB-613 treated mice compared to control animals 24 hours post-MI (FIG. 16C).

Example 4: Pharmacokinetic (PK) Studies of MCB-613, Compound 10-1, and Compound 10-2

The pharmacokinetics of MCB-613, Compound 10-1, and Compound 10-2 were tested in CD-1 mice. Each of the three compounds was dissolved in DMSO (20 mg/mL), mixed with 30% hydroxypropyl-β-cyclodextrin at a 1:9 ratio, and administered to the CD-1 mice intraperitoneally (ip) or orally (po) through a gavage. After compound administration, blood samples (3 mice per compound) were collected at nine time points, i.e., at 5 minutes, 0.25 hours, 0.5 hours, 1 hour, 2 hours, 4 hours, 8 hours, 12 hours, and 24 hours, through the tail vein. Plasma was isolated from these blood samples and the compound plasma concentrations were determined by HPLC-MS/MS. Pharmacokinetic parameters were calculated using the program PKSolver, an add-in program for use in analyzing pharmacokinetic and pharmacodynamics data analysis, as described in Zhang et al., Computer Methods and Programs in Biomedicine, 99: 306-314 (2010). The results are summarized in Tables 1 and 2, and include the half-life (t/2), the terminal phase half-life (terminal phase t/2), the time after administration of the compound at which the maximum concentration is reached ($t_{max}$), the maximum concentration of the compound observed ($C_{max}$), the area under the curve up to the last measurable concentration ($AUC_{0-t}$), the area under the curve to infinite time ($AUC_{0-inf}$), and the clearance rate of the compound ($C_l$).

Table 1 contains pharmacokinetic data from the above-described studies in which MCB-613, Compound 10-1, and Compound 10-2 were intraperitoneally administered to CD-1 mice.

TABLE 1

|  | MCB-613 | 10-1 | 10-2 |
|---|---|---|---|
| $t_{1/2}$ (h) | 0.86 | 0.64 | 0.25 |
| Terminal phase $t_{1/2}$ (h) | 6.5 | 18.1 | 15.9 |
| $t_{max}$ (h) | 0.08 | 0.25 | 0.08 |
| $C_{max}$ (ng/mL) | 49.2 | 356.7 | 463.3 |
| $AUC_{0-t}$ (ng/mL * h) | 122.2 | 622.6 | 333.8 |
| $AUC_{0-inf}$ (ng/mL * h) | 129.6 | 851.1 | 481.5 |
| Cl (mg)/(ng/mL)/h | 6.4 | 0.97 | 1.7 |

Table 2 contains pharmacokinetic data from the above-described studies in which MCB-613, Compound 10-1, and Compound 10-2 were orally administered to CD-1 mice.

TABLE 2

|  | MCB-613 | 10-1 | 10-2 |
|---|---|---|---|
| $t_{1/2}$ (h) | 0.94 | 1.2 | 0.78 |
| Terminal phase $t_{1/2}$ (h) | 16.1 | 10.2 | 27.1 |
| $t_{max}$ (h) | 0.25 | 0.5 | 0.25 |
| $C_{max}$ (ng/mL) | 5.6 | 53.2 | 181.9 |
| $AUC_{0-t}$ (ng/mL * h) | 15.7 | 98.4 | 131.1 |
| $AUC_{0-inf}$ (ng/mL * h) | 24.3 | 112.6 | 134.6 |
| Cl (mg)/(ng/mL)/h | 34 | 7.3 | 6.1 |

Figure 17:
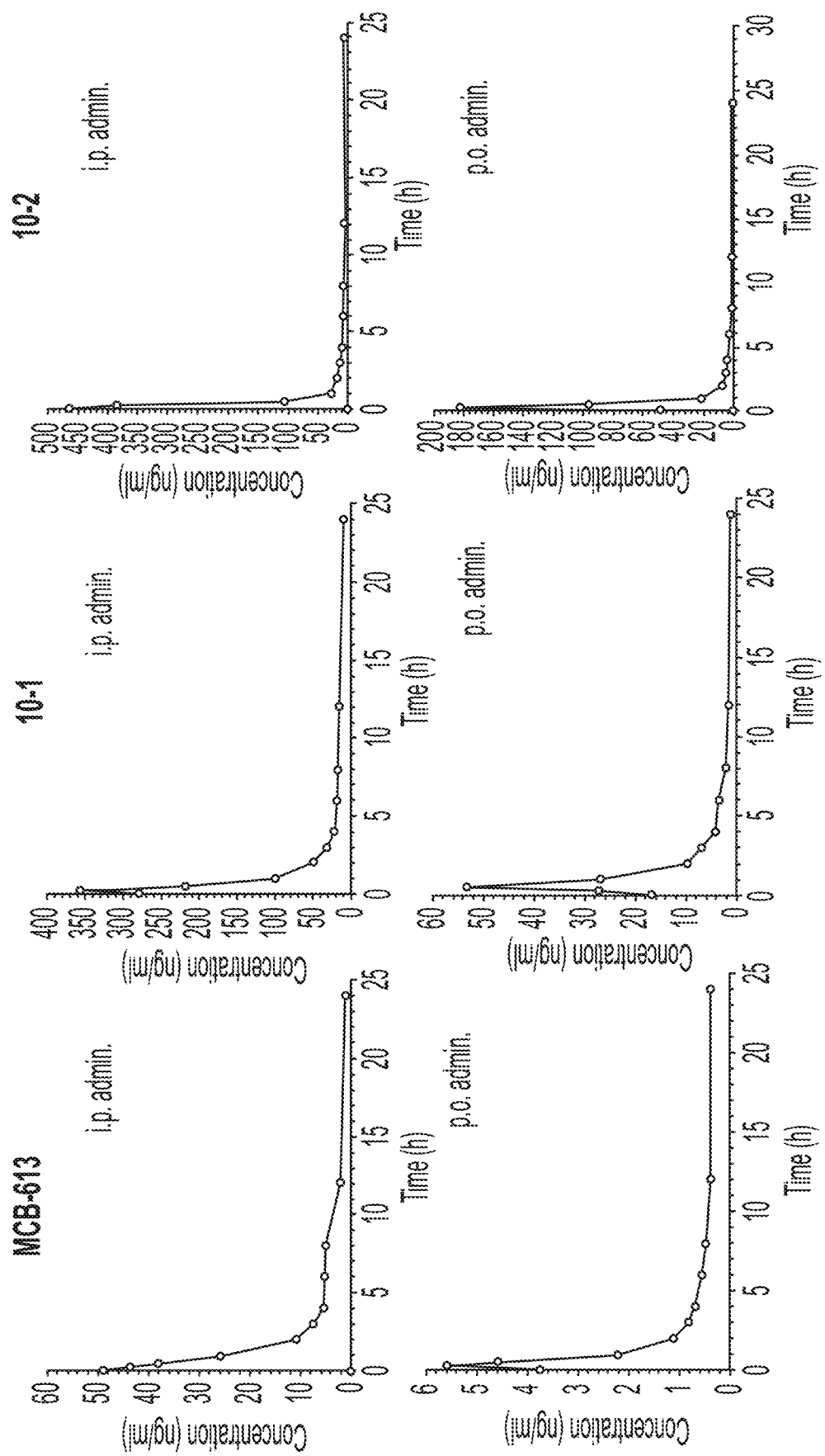
FIG. 17 contains graphical representations of pharmacokinetics data obtained for MCB-613, Compound 1, and Compound 2 in CD-1 mice.

The pharmacokinetic data are also illustrated in FIG. 17. The graphs in FIG. 17 show the average plasma concentration measured over time. The top row of graphs shows the pharmacokinetic data from the above-described studies in which MCB-613 (top left graph), Compound 10-1 (top middle graph), and Compound 10-2 (top right graph) were intraperitoneally administered to CD-1 mice. The bottom row of graphs shows the pharmacokinetic data from the above-described studies in which MCB-613 (bottom left graph), Compound 10-1 (bottom middle graph), and Compound 10-2 (bottom right graph) were orally administered to CD-1 mice.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:

1. A compound of the following formula:

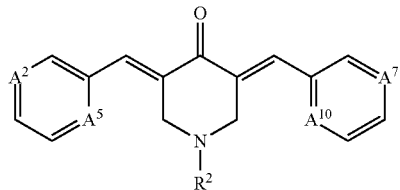

or a pharmaceutically acceptable salt or prodrug thereof, wherein:
$A^2$ and $A^7$ are each independently selected from $CR^1$, wherein each $R^1$ is halogen, alkoxy, cyano, trifluoromethyl, or substituted or unsubstituted $C_{1-6}$ alkyl;
$A^5$ and $A^{10}$ are each independently selected from $CR^1$, wherein $R^1$ is hydrogen, cyano, or substituted or unsubstituted $C_{1-6}$ alkyl; and
$R^2$ is substituted or unsubstituted cycloalkyl or substituted or unsubstituted heterocycloalkyl, wherein $R^2$ is not cyclohexyl.

2. The compound of claim 1, wherein the compound has the following formula:

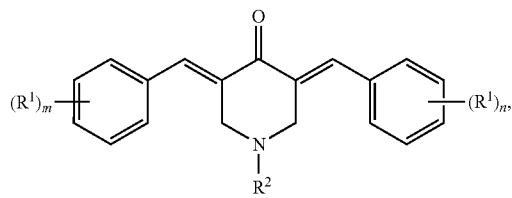

wherein:
m and n are each independently 1, 2, 3, 4, or 5.

3. The compound of claim 1, wherein $R^2$ is selected from the group consisting of cyclopropyl, cyclobutyl, cyclopentyl, cycloheptyl, and cyclooctyl.

4. The compound of claim 1, wherein the compound is:

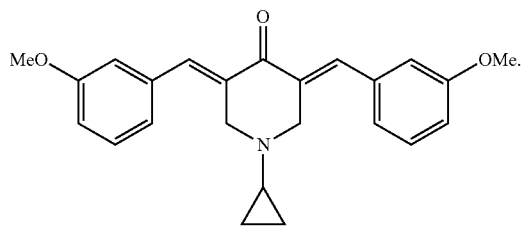 [SMILES: COc1cccc(/C=C2\CN(C3CC3)C/C(=C\c3cccc(OC)c3)C2=O)c1]

5. A method for treating an ischemic injury in a subject, comprising:
administering to the subject an effective amount of a compound of the following formula:

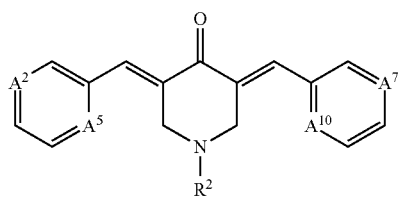

or a pharmaceutically acceptable salt or prodrug thereof, wherein:
- $A^2$ and $A^7$ are each independently selected from $CR^1$, wherein each $R^1$ is halogen, alkoxy, cyano, trifluoromethyl, or substituted or unsubstituted $C_{1-6}$ alkyl;
- $A^5$ and $A^{10}$ are each independently selected from $CR^1$, wherein $R^1$ is hydrogen, cyano, or substituted or unsubstituted $C_{1-6}$ alkyl; and
- $R^2$ is substituted or unsubstituted cycloalkyl or substituted or unsubstituted heterocycloalkyl, wherein $R^2$ is not cyclohexyl.

6. The method of claim 5, wherein the compound is selected from the group consisting of:

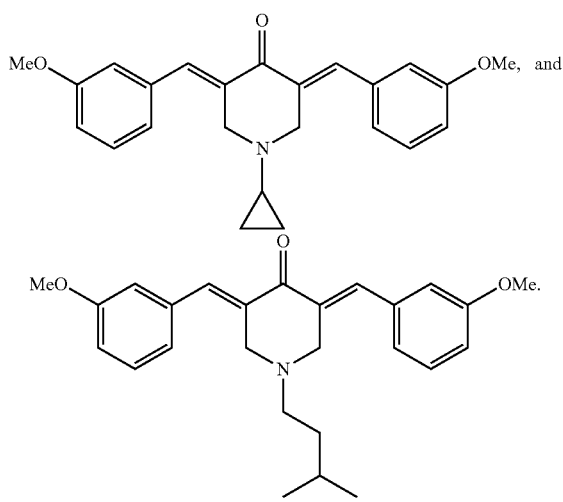

7. The method of claim 5, wherein the ischemic injury comprises a myocardial infarction or a stroke.

8. The method of claim 5, further comprising selecting a subject who has suffered an ischemic injury, wherein the ischemic injury comprises a myocardial infarction or a stroke.

9. A method of reducing a myocardial infarct size, reducing cardiomyocyte loss, improving cardiac vascular perfusion, and/or improving central nervous system vascular perfusion in a subject who has suffered a myocardial infarction or stroke, comprising:
administering to the subject an effective amount of a compound of the following formula:

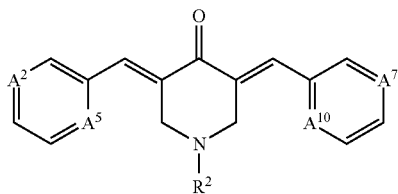

or a pharmaceutically acceptable salt or prodrug thereof, wherein:
- $A^2$ and $A^7$ are each independently selected from $CR^1$, wherein each $R^1$ is halogen, alkoxy, cyano, trifluoromethyl, or substituted or unsubstituted $C_{1-6}$ alkyl;
- $A^5$ and $A^{10}$ are each independently selected from $CR^1$, wherein $R^1$ is hydrogen, cyano, or substituted or unsubstituted $C_{1-6}$ alkyl; and
- $R^2$ is substituted or unsubstituted cycloalkyl or substituted or unsubstituted heterocycloalkyl, wherein $R^2$ is not cyclohexyl.

10. The method of claim 9, wherein the compound is selected from the group consisting of:

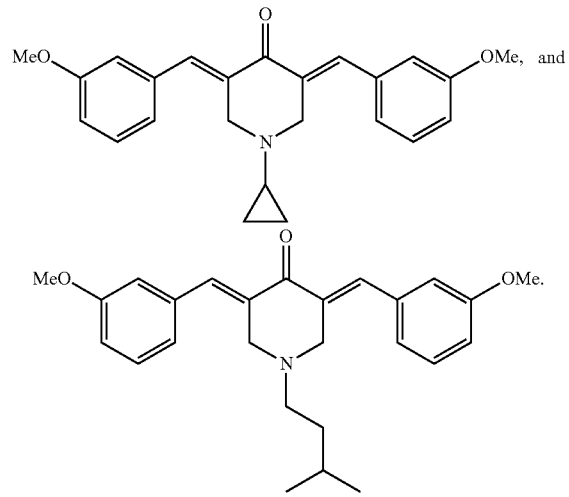

11. A method of improving cardiovascular function and/or central nervous system vascular function in a subject, promoting wound healing in a subject, or treating hypertrophic cardiomyopathy in a subject, comprising administering to the subject an effective amount of a compound of the following formula:

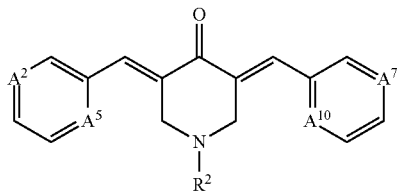

or a pharmaceutically acceptable salt or prodrug thereof, wherein:
- $A^2$ and $A^7$ are each independently selected from $CR^1$, wherein each $R^1$ is halogen, alkoxy, cyano, trifluoromethyl, or substituted or unsubstituted $C_{1-6}$ alkyl;
- $A^5$ and $A^{10}$ are each independently selected from $CR^1$, wherein $R^1$ is hydrogen, cyano, or substituted or unsubstituted $C_{1-6}$ alkyl; and
- $R^2$ is substituted or unsubstituted cycloalkyl or substituted or unsubstituted heterocycloalkyl, wherein $R^2$ is not cyclohexyl.

12. The method of claim 11, wherein the compound is selected from the group consisting of:

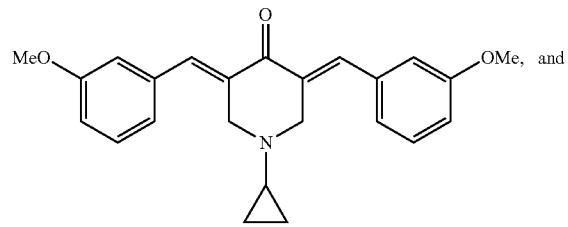

-continued
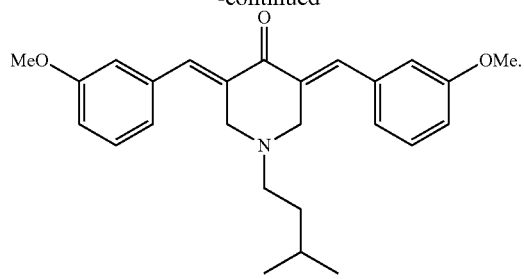
13. The method of claim 11, wherein the subject has suffered an ischemic injury.
14. The method of claim 13, wherein the ischemic injury is a myocardial infarction or a stroke.
15. The method of claim 11, wherein the subject is an elderly subject.
* * * * *